US012778747B2

(12) United States Patent
Chau

(10) Patent No.: US 12,778,747 B2
(45) Date of Patent: Nov. 3, 2026

(54) PROSTHETIC VALVE DOCKING DEVICE

(71) Applicant: EDWARDS LIFESCIENCES CORPORATION, Irvine, CA (US)

(72) Inventor: Jocelyn Chau, Buena Park, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 377 days.

(21) Appl. No.: 18/432,653

(22) Filed: Feb. 5, 2024

(65) Prior Publication Data

US 2024/0173121 A1 May 30, 2024

Related U.S. Application Data

(63) Continuation of application No. PCT/US2022/045376, filed on Sep. 30, 2022.

(60) Provisional application No. 63/253,995, filed on Oct. 8, 2021.

(51) Int. Cl.
*A61F 2/24* (2006.01)
*A61F 2/88* (2006.01)

(52) U.S. Cl.
CPC .............. *A61F 2/2409* (2013.01); *A61F 2/88* (2013.01); *A61F 2210/0014* (2013.01); *A61F 2220/0008* (2013.01); *A61F 2230/0091* (2013.01); *A61F 2240/001* (2013.01); *A61F 2250/0063* (2013.01)

(58) Field of Classification Search
CPC ........ A61F 2/2409; A61F 2/2445; A61F 2/88; A61F 2230/0091; A61F 2210/0076; A61F 2250/0069; A61F 2250/0063; A61F 2250/001; A61F 2220/0008; A61F 2/2418
See application file for complete search history.

(56) References Cited

U.S. PATENT DOCUMENTS

| | | | |
|---|---|---|---|
| 4,035,849 | A | 7/1977 | Angell et al. |
| 4,164,046 | A | 8/1979 | Cooley |
| 4,790,843 | A | 12/1988 | Carpentier et al. |
| 5,059,177 | A | 10/1991 | Towne et al. |
| 5,411,552 | A | 5/1995 | Andersen et al. |
| 5,554,185 | A | 9/1996 | Block et al. |
| 5,840,081 | A | 11/1998 | Andersen et al. |

(Continued)

FOREIGN PATENT DOCUMENTS

| | | | |
|---|---|---|---|
| DE | 19532846 | A1 | 3/1997 |
| DE | 19907646 | A1 | 8/2000 |

(Continued)

OTHER PUBLICATIONS

Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

*Primary Examiner* — Javier G Blanco
(74) *Attorney, Agent, or Firm* — Klarquist Sparkman LLP

(57) ABSTRACT

Certain examples of the disclosure concern a method for assembling a cover assembly for a docking device configured to receive a prosthetic valve. The method includes braiding a first layer over a mandrel, braiding a second layer over the first layer to form a multi-layer structure, shape-setting the multi-layer structure so that the multi-layer structure conforms to a shape of the mandrel, and laser cutting the multi-layer structure to form a proximal end and a distal end. The laser cutting can fuse the second layer to the first layer at the proximal end and the distal end.

8 Claims, 26 Drawing Sheets

(56) References Cited

U.S. PATENT DOCUMENTS 6,168,614 B1 1/2001 Andersen et al.
6,217,610 B1 4/2001 Carpentier et al.
6,368,348 B1 4/2002 Gabbay
6,419,696 B1 7/2002 Ortiz et al.
6,425,916 B1 7/2002 Garrison et al.
6,432,134 B1 8/2002 Anson et al.
6,458,153 B1 10/2002 Bailey et al.
6,527,979 B2 3/2003 Constantz et al.
6,582,462 B1 6/2003 Andersen et al.
6,652,578 B2 11/2003 Bailey et al.
6,730,121 B2 5/2004 Ortiz et al.
6,797,002 B2 9/2004 Spence et al.
6,908,481 B2 6/2005 Cribier
6,964,684 B2 11/2005 Ortiz et al.
7,018,408 B2 3/2006 Bailey et al.
7,037,334 B1 5/2006 Hlavka et al.
7,077,861 B2 7/2006 Spence
7,101,395 B2 9/2006 Tremulis et al.
7,125,421 B2 10/2006 Tremulis et al.
7,445,632 B2 11/2008 McGuckin, Jr. et al.
7,585,321 B2 9/2009 Cribier
7,618,446 B2 11/2009 Andersen et al.
7,637,946 B2 12/2009 Solem et al.
7,708,775 B2 5/2010 Rowe et al.
7,737,060 B2 6/2010 Strickler et al.
7,785,366 B2 8/2010 Maurer et al.
7,951,195 B2 5/2011 Antonsson et al.
8,128,691 B2 3/2012 Keranen
8,142,492 B2 3/2012 Forster et al.
8,236,049 B2 8/2012 Rowe et al.
8,323,335 B2 12/2012 Rowe et al.
8,377,115 B2 2/2013 Thompson
8,398,708 B2 3/2013 Meiri et al.
8,449,599 B2 5/2013 Chau et al.
8,449,605 B2 5/2013 Lichtenstein et al.
8,449,606 B2 5/2013 Eliasen et al.
8,657,872 B2 2/2014 Seguin
8,663,322 B2 3/2014 Keranen
8,672,998 B2 3/2014 Lichtenstein et al.
8,685,086 B2 4/2014 Navia et al.
8,801,776 B2 8/2014 House et al.
8,840,664 B2 9/2014 Karapetian et al.
9,078,747 B2 7/2015 Conklin
9,095,434 B2 8/2015 Rowe
9,119,718 B2 9/2015 Keranen
9,192,471 B2 11/2015 Bolling
9,237,886 B2 1/2016 Seguin et al.
9,314,335 B2 4/2016 Konno
9,326,853 B2 5/2016 Olson et al.
9,463,268 B2 10/2016 Spence
9,474,599 B2 10/2016 Keranen
9,526,572 B2 12/2016 Kunis
9,597,205 B2 3/2017 Tuval
9,622,863 B2 4/2017 Karapetian et al.
9,867,702 B2 1/2018 Keränen et al.
10,016,272 B2 7/2018 Spence et al.
10,016,276 B2 7/2018 Brunnett et al.
10,034,749 B2 7/2018 Spence et al.
10,039,637 B2 8/2018 Maimon et al.
10,052,198 B2 8/2018 Chau et al.
10,195,028 B2 2/2019 Hosmer et al.
10,195,033 B2 2/2019 Tuval et al.
10,226,339 B2 3/2019 Spence et al.
10,357,361 B2 7/2019 Rafi et al.
10,463,479 B2 11/2019 Manash et al.
10,828,150 B2 11/2020 Tamir
11,020,225 B2 6/2021 Keränen et al.
11,039,924 B2 6/2021 Yaron
11,065,111 B2 7/2021 Manash et al.
11,141,273 B2 10/2021 Dakin et al.
11,185,406 B2 11/2021 Haivatov et al.
11,364,114 B2 6/2022 Gorman, III et al.
11,382,748 B2 7/2022 Keränen et al.
11,471,282 B2 10/2022 Argento et al.
11,547,563 B2 1/2023 Keränen et al.
11,654,025 B2 5/2023 O'Carroll et al.
11,666,441 B2 6/2023 McDaniel et al.
2002/0032481 A1 3/2002 Gabbay
2002/0107535 A1 8/2002 Wei et al.
2002/0151970 A1 10/2002 Garrison et al.
2002/0173841 A1 11/2002 Ortiz et al.
2003/0225420 A1 12/2003 Wardle
2004/0111006 A1 6/2004 Alferness et al.
2004/0260389 A1 12/2004 Case et al.
2005/0043791 A1 2/2005 McCarthy et al.
2005/0096736 A1 5/2005 Osse et al.
2005/0119682 A1 6/2005 Nguyen et al.
2005/0119735 A1 6/2005 Spence et al.
2005/0137691 A1 6/2005 Salahieh et al.
2005/0182486 A1 8/2005 Gabbay
2005/0203614 A1 9/2005 Forster et al.
2005/0203617 A1 9/2005 Forster et al.
2005/0256567 A1 11/2005 Lim et al.
2006/0025857 A1 2/2006 Bergheim et al.
2006/0025858 A1 2/2006 Alameddine
2006/0195134 A1 8/2006 Crittenden
2006/0195185 A1 8/2006 Lane et al.
2006/0271172 A1 11/2006 Tehrani
2007/0179604 A1 8/2007 Lane
2007/0203575 A1 8/2007 Forster et al.
2007/0265700 A1 11/2007 Eliasen et al.
2007/0293808 A1 12/2007 Williams et al.
2008/0033542 A1 2/2008 Antonsson et al.
2008/0077235 A1 3/2008 Kirson
2008/0125853 A1 5/2008 Bailey et al.
2008/0140190 A1 6/2008 Macoviak et al.
2008/0208327 A1 8/2008 Rowe
2008/0208330 A1 8/2008 Keranen
2009/0192601 A1 7/2009 Rafiee et al.
2009/0276038 A1 11/2009 Tremulis et al.
2009/0319037 A1 12/2009 Rowe et al.
2010/0036484 A1 2/2010 Hariton et al.
2010/0145440 A1 6/2010 Keranen
2010/0280604 A1 11/2010 Zipory et al.
2010/0312333 A1 12/2010 Navia et al.
2010/0318184 A1 12/2010 Spence
2011/0034999 A1 2/2011 Carpentier et al.
2011/0276130 A1 11/2011 Alameddine
2012/0059458 A1 3/2012 Buchbinder et al.
2012/0123529 A1 5/2012 Levi et al.
2012/0283820 A1 11/2012 Tseng et al.
2013/0190865 A1 7/2013 Anderson
2013/0204311 A1 8/2013 Kunis
2014/0074299 A1 3/2014 Endou et al.
2014/0081394 A1 3/2014 Keranen et al.
2014/0163669 A1 6/2014 Ben-Zvi et al.
2014/0172070 A1 6/2014 Seguin
2014/0358222 A1 12/2014 Gorman, III et al.
2014/0379074 A1 12/2014 Spence et al.
2015/0025623 A1 1/2015 Granada et al.
2015/0190227 A1 7/2015 Johnson et al.
2015/0230921 A1 8/2015 Chau et al.
2015/0245910 A1 9/2015 Righini et al.
2015/0282931 A1 10/2015 Brunnett et al.
2015/0335428 A1 11/2015 Keranen
2015/0335430 A1 11/2015 Loulmet et al.
2015/0374493 A1 12/2015 Yaron et al.
2016/0015514 A1 1/2016 Lashinski et al.
2016/0074165 A1 3/2016 Spence et al.
2016/0095705 A1 4/2016 Keranen et al.
2016/0143732 A1 5/2016 Glimsdale
2016/0184095 A1 6/2016 Spence et al.
2016/0199177 A1 7/2016 Spence et al.
2016/0256276 A1 9/2016 Yaron
2016/0346080 A1 12/2016 Righini et al.
2017/0007399 A1 1/2017 Keranen
2017/0007402 A1 1/2017 Zerkowski et al.
2017/0217385 A1 8/2017 Rinkleff et al.
2017/0266005 A1 9/2017 McGuckin, Jr.
2017/0273789 A1 9/2017 Yaron et al.
2017/0281337 A1 10/2017 Campbell
2017/0360426 A1 12/2017 Hacohen et al.
2018/0000580 A1 1/2018 Wallace et al.
2018/0085217 A1 3/2018 Lashinski et al.

(56) References Cited

U.S. PATENT DOCUMENTS

| | | | |
|---|---|---|---|
| 2018/0206074 | A1 | 7/2018 | Tanasa et al. |
| 2018/0289481 | A1 | 10/2018 | Dolan |
| 2018/0303606 | A1 | 10/2018 | Rothstein et al. |
| 2018/0318073 | A1 | 11/2018 | Tseng et al. |
| 2018/0318080 | A1 | 11/2018 | Quill et al. |
| 2020/0054453 | A1 | 2/2020 | Zerkowski et al. |
| 2020/0360143 | A1 | 11/2020 | O'Carroll et al. |
| 2021/0212826 | A1 | 7/2021 | Zerkowski et al. |
| 2021/0361426 | A1 | 11/2021 | Hacohen |
| 2023/0086853 | A1 | 3/2023 | Zerkowski et al. |

FOREIGN PATENT DOCUMENTS

| | | | |
|---|---|---|---|
| EP | 0338994 | A1 | 10/1989 |
| EP | 0624080 | A1 | 11/1994 |
| EP | 0592410 | B1 | 10/1995 |
| EP | 0850607 | A1 | 7/1998 |
| EP | 1432369 | A1 | 6/2004 |
| EP | 1521550 | A2 | 4/2005 |
| EP | 1296618 | B1 | 1/2008 |
| EP | 1827314 | B1 | 12/2010 |
| EP | 2591754 | A1 | 5/2013 |
| EP | 3395296 | B1 | 12/2019 |
| EP | 2747708 | B1 | 1/2022 |
| WO | 9117720 | A1 | 11/1991 |
| WO | 9719655 | A1 | 6/1997 |
| WO | 9824386 | A1 | 6/1998 |
| WO | 0149213 | A2 | 7/2001 |
| WO | 0154625 | A1 | 8/2001 |
| WO | 0247575 | A2 | 6/2002 |
| WO | 0249546 | A2 | 6/2002 |
| WO | 2005084595 | A1 | 9/2005 |
| WO | 2005102015 | A2 | 11/2005 |
| WO | 2005107650 | A2 | 11/2005 |
| WO | 2006011127 | A2 | 2/2006 |
| WO | 2006091163 | A1 | 8/2006 |
| WO | 2007067942 | A1 | 6/2007 |
| WO | 2008058940 | A1 | 5/2008 |
| WO | 2009139776 | A1 | 11/2009 |
| WO | 2010121076 | A2 | 10/2010 |
| WO | 2012063228 | A1 | 5/2012 |
| WO | 2015198125 | A1 | 12/2015 |
| WO | 2017103833 | A1 | 6/2017 |
| WO | 2020247907 | A1 | 12/2020 |

PROSTHETIC VALVE DOCKING DEVICE

CROSS-REFERENCE TO RELATED APPLICATIONS

This application is a continuation of PCT patent application no. PCT/US2022/045376, filed on Sep. 30, 2022, which claims the benefit of U.S. Provisional Application No. 63/253,995, filed on Oct. 8, 2021, each of which is incorporated by reference herein.

FIELD

The present disclosure concerns examples of a docking device configured to secure a prosthetic valve at a native heart valve, as well as methods of assembling such devices.

BACKGROUND

Prosthetic valves can be used to treat cardiac valvular disorders. Native heart valves (e.g., the aortic, pulmonary, tricuspid and mitral valves) function to prevent backward flow or regurgitation, while allowing forward flow. These heart valves can be rendered less effective by congenital, inflammatory, infectious conditions, etc. Such conditions can eventually lead to serious cardiovascular compromise or death. For many years, the doctors attempted to treat such disorders with surgical repair or replacement of the valve during open heart surgery.

A transcatheter technique for introducing and implanting a prosthetic heart valve using a catheter in a manner that is less invasive than open heart surgery can reduce complications associated with open heart surgery. In this technique, a prosthetic valve can be mounted in a compressed state on the end portion of a catheter and advanced through a blood vessel of the patient until the valve reaches the implantation site. The valve at the catheter tip can then be expanded to its functional size at the site of the defective native valve, such as by inflating a balloon on which the valve is mounted or, for example, the valve can have a resilient, self-expanding stent or frame that expands the valve to its functional size when it is advanced from a delivery sheath at the distal end of the catheter. Optionally, the valve can have a balloon-expandable, self-expanding, mechanically expandable frame, and/or a frame expandable in multiple or a combination of ways.

In some instances, a transcatheter heart valve (THV) may be appropriately sized to be placed inside a particular native valve (e.g., a native aortic valve). As such, the THV may not be suitable for implantation at another native valve (e.g., a native mitral valve) and/or in a patient with a larger native valve. Additionally or alternatively, the native tissue at the implantation site may not provide sufficient structure for the THV to be secured in place relative to the native tissue. Accordingly, improvements to THVs and the associated transcatheter delivery apparatus are desirable.

SUMMARY

The present disclosure relates to methods and devices for treating valvular regurgitation and/or other valve issues. Specifically, the present disclosure is directed to a docking device configured to receive a prosthetic valve and the methods of assembling the docking device and implanting the docking device.

In one aspect, a docking device can comprise a coil and a guard member surrounding at least a portion of the coil. In addition to these components, a docking device can further comprise one or more of the components disclosed herein.

In some examples, the guard member can include a first layer and a second layer that are fused with each other at a proximal end and a distal end of the guard member.

In some examples, the distal end of the guard member can be fixedly attached to the coil, and the proximal end of the guard member can be movable relative to the coil. In some examples, the guard member can be movable between a radially compressed state and a radially expanded state.

In one aspect, a method can comprise forming a guard member and attaching the guard member to a docking device. In addition to these steps, the method can further comprise one or more of the steps disclosed herein.

Certain examples of the disclosure concern a docking device for securing a prosthetic valve at a native valve. The docking device can include a coil and a guard member surrounding at least a portion of the coil. The guard member can include a first layer and a second layer that are fused with each other at a proximal end and a distal end of the guard member. The distal end of the guard member can be fixedly attached to the coil. The proximal end of the guard member can be movable relative to the coil. The guard member can be movable between a radially compressed state and a radially expanded state.

Certain examples of the disclosure concern a method for assembling a docking device configured to receive a prosthetic valve. The method can include forming a guard member having a proximal end and a distal end, and attaching the guard member to the docking device. The guard member can include a first layer and a second layer that are fused together at the proximal end and the distal end. The guard member can surround at least a portion of a coil of the docking device and be movable between a radially compressed state and a radially expanded state. The distal end of the guard member can be fixed relative to the coil and the proximal end of the guard member can be movable relative to the coil. In the radially expanded state, the guard member can be configured to reduce paravalvular leakage around the prosthetic valve.

Certain examples of the disclosure concern a method for assembling a cover assembly for a docking device configured to receive a prosthetic valve. The method can include braiding a first layer over a mandrel, braiding a second layer over the first layer to form a multi-layer structure, shape setting the multi-layer structure so that the multi-layer structure conforms to a shape of the mandrel, laser cutting the multi-layer structure to form a proximal end and a distal end, and allowing the proximal end and the distal end to cure such that the second layer and the first layer are fused at the proximal end and the distal end.

In some examples, a docking device can comprise one or more of the components recited in Examples 1-18 described in the section "Additional Examples of the Disclosed Technology" below.

In some examples, a method for assembling a docking device or a method for assembling a cover assembly for a docking device comprises one or more of the steps recited in Examples 18-38 described in the section "Additional Examples of the Disclosed Technology" below.

Certain examples of the disclosure concern a method for implanting a prosthetic valve. The method can include deploying a docking device at a native valve, and deploying the prosthetic valve within the docking device. The docking device can include a coil and a guard member covering at least a portion of the coil. The guard member can include a first layer and a second layer that are fused together at a proximal end and a distal end of the guard member. The guard member can be movable between a radially compressed state and a radially expanded state. A distal end of the guard member can be fixed relative to the coil and a proximal end of the guard member can be movable relative to the coil. In the radially expanded state, the guard member can be configured to reduce paravalvular leakage around the prosthetic valve.

In some examples, a method for implanting a prosthetic valve can comprise one or more of the steps recited in Examples 39-46 described in the section "Additional Examples of the Disclosed Technology" below.

The above method(s) can be performed on a living animal or on a simulation, such as on a cadaver, cadaver heart, anthropomorphic ghost, simulator (e.g., with body parts, heart, tissue, etc. being simulated).

The foregoing and other objects, features, and advantages of the disclosed technology will become more apparent from the following detailed description, which proceeds with reference to the accompanying figures.

DETAILED DESCRIPTION

General Considerations

Figure 1A:
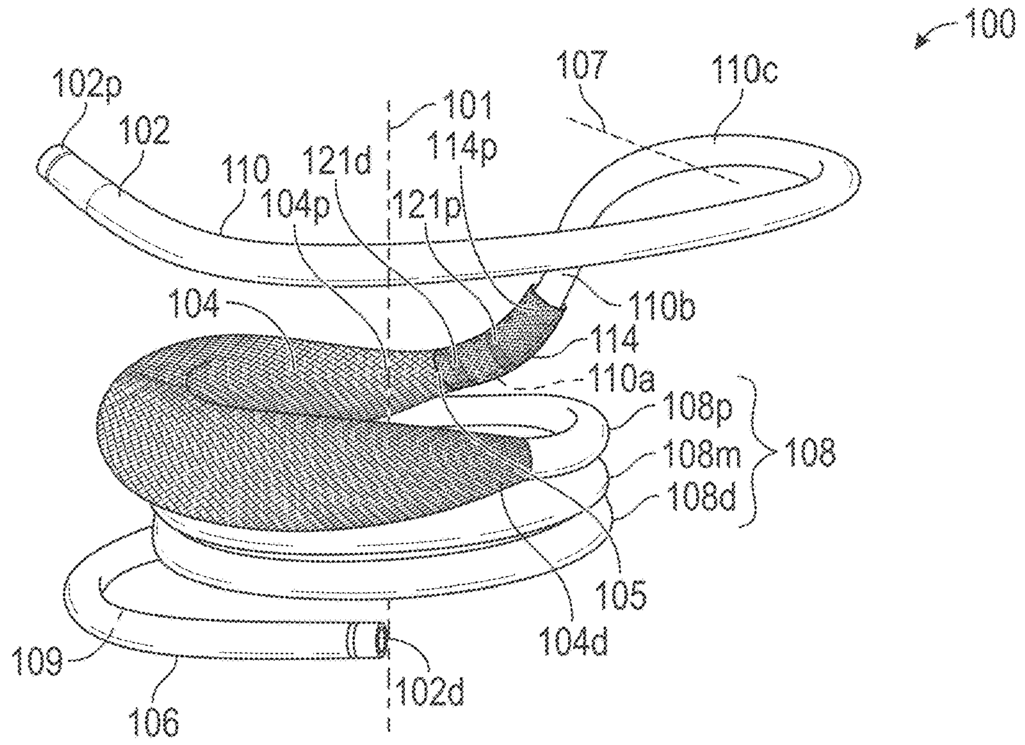
FIG. 1A is a side perspective view of a docking device in a helical configuration, according to one example.

It should be understood that the disclosed examples can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved. The technologies from any example can be combined with the technologies described in any one or more of the other examples. In view of the many possible examples to which the principles of the disclosed technology may be applied, it should be recognized that the illustrated examples are only preferred examples and should not be taken as limiting the scope of the disclosed technology.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the term "approximately" and "about" means the listed value and any value that is within 10% of the listed value. For example, "about 1 mm" means any value between about 0.9 mm and about 1.1 mm, inclusive.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

Introduction to the Disclosed Technology

Disclosed herein are various systems, apparatuses, methods, etc., including anchoring or docking devices, which can be used in conjunction with expandable prosthetic valves at a native valve annulus (e.g., a native mitral and/or tricuspid valve annulus), in order to more securely implant and hold the prosthetic valve at the implant site. Anchoring/docking devices according to examples of the disclosure can, for example, provide a stable anchoring site, landing zone, or implantation zone at the implant site in which prosthetic valves can be expanded or otherwise implanted. Many of the disclosed docking devices comprise a circular or cylindrically-shaped portion, which can (for example) allow a prosthetic heart valve comprising a circular or cylindrically-shaped valve frame or stent to be expanded or otherwise implanted into native locations with naturally circular cross-sectional profiles and/or in native locations with naturally with non-circular cross sections. In addition to providing an anchoring site for the prosthetic valve, the anchoring/docking devices can be sized and shaped to cinch or draw the native valve (e.g., mitral, tricuspid, etc.) anatomy radially inwards. In this manner, one of the main causes of valve regurgitation (e.g., functional mitral regurgitation), specifically enlargement of the heart (e.g., enlargement of the left ventricle, etc.) and/or valve annulus, and consequent stretching out of the native valve (e.g., mitral, etc.) annulus, can be at least partially offset or counteracted. Some examples of the anchoring or docking devices further include features which, for example, are shaped and/or modified to better hold a position or shape of the docking device during and/or after expansion of a prosthetic valve therein. By providing such anchoring or docking devices, replacement valves can be more securely implanted and held at various valve annuluses, including at the mitral valve annulus which does not have a naturally circular cross-section.

In some instances, a docking device can comprise a paravalvular leakage (PVL) guard (also referred to herein as "a guard member"). The PVL guard can, for example, help reduce regurgitation and/or promote tissue ingrowth between the native tissue and the docking device.

The PVL guard can, in some examples, be movable between a delivery configuration and a deployed configuration. When the PVL guard is in the delivery configuration, an outer edge of the PVL guard can extend along and adjacent the coil. When the PVL guard is in the deployed configuration, the outer edge of the PVL guard can form a helical shape rotating about a central longitudinal axis of the coil and at least a segment of the outer edge of PVL guard can extend radially away from the coil.

In certain examples, the PVL guard can cover or surround a portion of a coil of the docking device. As described more fully below, such PVL guard can move from a radially compressed (and axially elongated) state to a radially expanded (and axially foreshortened) state, and a proximal end portion of the PVL guard can be axially movable relative to the coil.

In other examples, the PVL guard can be foldable along a segment of a coil of the docking device. As described more fully below, such PVL guard can have an inner edge coupled the coil and an outer edge that is movable between a folded position and an extended position. The outer edge in the folded position can extend along and adjacent to the coil, and at least a segment of the outer edge in the extended position can be spaced apart from the coil.

Exemplary methods of attaching the PVL guard to the docking device and example methods of limiting axial movement of the PVL guard are also disclosed herein.

Exemplary Docking Devices

Figure 3A:
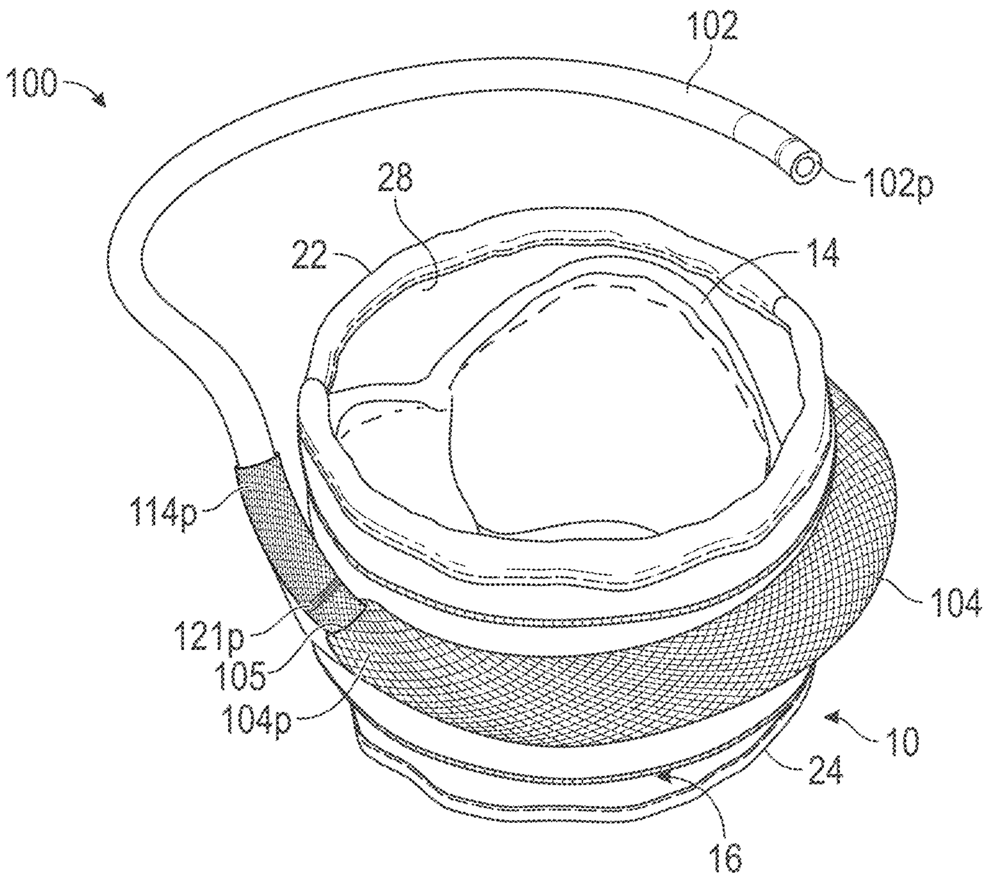
FIG. 3A is a perspective view of an exemplary prosthetic implant assembly comprising the docking device depicted in FIG. 1A and the prosthetic valve of FIG. 2B retained within the docking device.
Figure 3B:
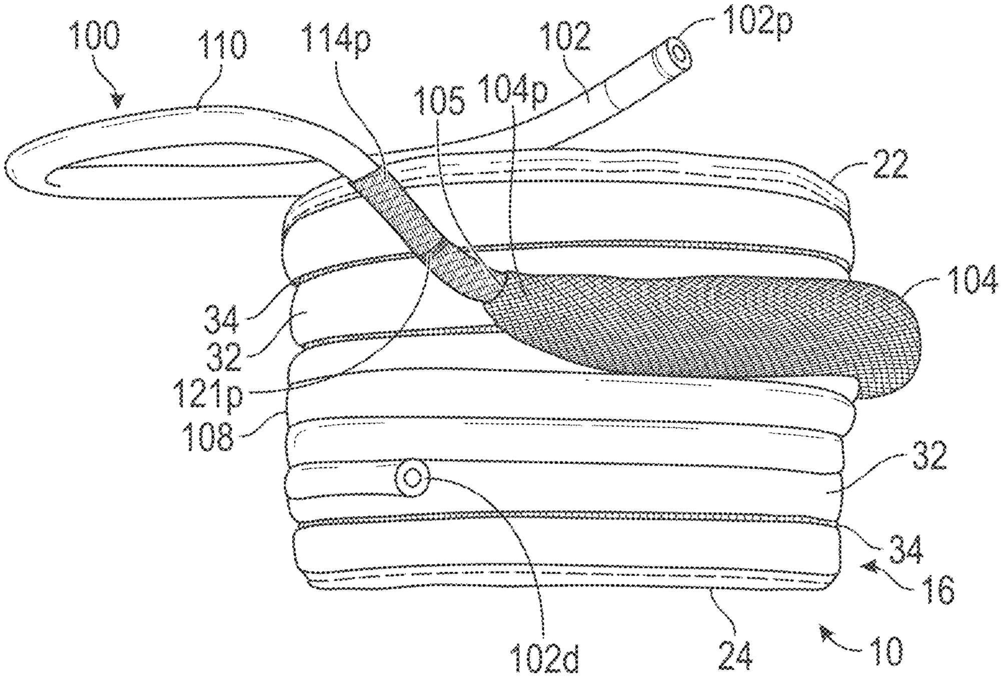
FIG. 3B is a side elevation view of the prosthetic implant assembly of FIG. 3.
Figure 24:
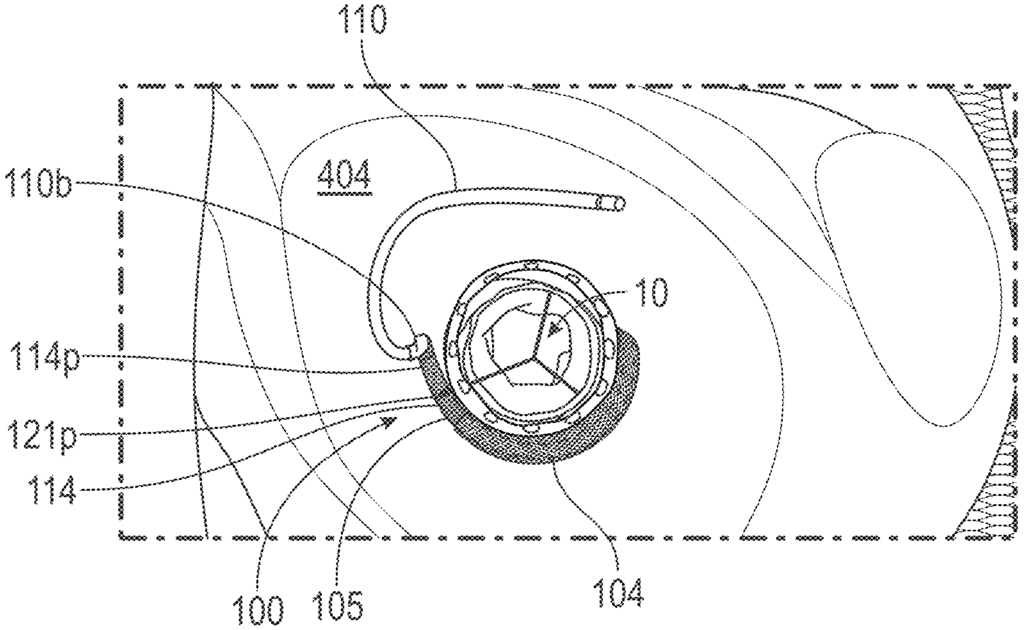

FIGS. 1A-1G show a docking device 100, according to one example. The docking device 100 can, for example, be implanted within a native valve annulus (see, e.g., FIG. 13). As depicted in FIGS. 3A-3B and 24, the docking device can be configured to receive and secure a prosthetic valve within the docking device, thereby securing the prosthetic valve at the native valve annulus.

Figure 1B:
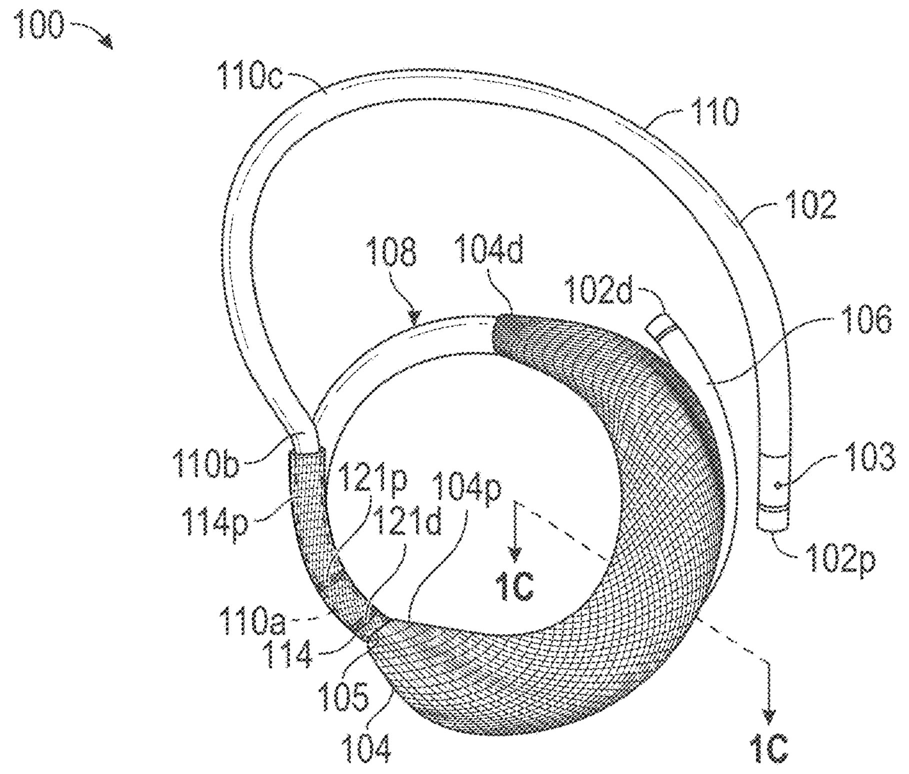
FIG. 1B is a top view of the docking device depicted in FIG. 1A.

Referring to FIGS. 1A-1G, the docking device 100 can comprise a coil 102 and a guard member 104 covering at least a portion of the coil 102. In certain examples, the coil 102 can include a shape memory material (e.g., nickel titanium alloy or "Nitinol") such that the docking device 100 (and the coil 102) can move from a substantially straight configuration (also referred to as "delivery configuration") when disposed within a delivery sheath of a delivery apparatus (as described more fully below) to a helical configuration (also referred to as "deployed configuration," as shown in FIGS. 1A-1B) after being removed from the delivery sheath.

In certain examples, when the guard member 104 is in the deployed configuration, the guard member 104 can extend circumferentially relative to a central longitudinal axis 101 of the docking device 100 from 180 degrees to 400 degrees, or from 210 degrees to 330 degrees, or from 250 degrees to 290 degrees, or from 260 degrees to 280 degrees. In one particular example, when the guard member 104 is in the deployed configuration, the guard member 104 can extend circumferentially 270 degrees relative to the central longitudinal axis 101. In other words, the guard member 104 can extend circumferentially from about one half of a revolution (e.g., 180 degrees) around the central longitudinal axis 101 in some examples to more than a full revolution (e.g., 400 degrees) around the central longitudinal axis 101 in other examples, including various ranges in between. As used herein, a range (e.g., 180-400 degrees, from 180 degrees to 400 degrees, and between 180 degrees and 400 degrees) includes the endpoints of the range (e.g., 180 degrees and 400 degrees).

In some examples, the docking device 100 can also include a retention element 114 surrounding at least a portion of the coil 102 and at least being partially covered by the guard member 104. In some instances, the retention element 114 can comprise a braided material. In addition, the retention element 114 can provide a surface area that encourages or promotes tissue ingrowth and/or adherence, and/or reduce trauma to native tissue. For example, in certain instances, the retention element 114 can have a textured outer surface configured to promote tissue ingrowth. In certain instances, the retention element 114 can be impregnated with growth factors to stimulate or promote tissue ingrowth.

In one example, as illustrated in FIGS. 1A-1B and 3A-3B, at least a proximal end portion of the retention element 114 can extend out of a proximal end of the guard member 104. In another example, the retention element 114 can be completely covered by the guard member 104.

As described further below, the retention element 114 can be designed to interact with the guard member 104 to limit or resist motion of the guard member 104 relative to the coil 102. For example, a proximal end 105 of the guard member 104 can have an inner diameter that is about the same as an outer diameter of the retention element 114. As such, an inner surface of the guard member 104 at the proximal end 105 can frictionally interact or engage with the retention element 114 so that axial movement of the proximal end 105 of the guard member 104 relative to the coil 102 can be impeded by a frictional force exerted by the retention element 114.

The coil 102 has a proximal end **102*p* and a distal end 102*d* (which also respectively define the proximal and distal ends of the docking device 100). When being disposed within the delivery sheath (e.g., during delivery of the docking device into the vasculature of a patient), a body of the coil 102 between the proximal end 102*p* and distal end 102*d* can form a generally straight delivery configuration (i.e., without any coiled or looped portions, but can be flexed or bent) so as to maintain a small radial profile when moving through a patient's vasculature. After being removed from the delivery sheath and deployed at an implant position, the coil 102 can move from the delivery configuration to the helical deployed configuration and wrap around native tissue adjacent the implant position. For example, when implanting the docking device at the location of a native valve, the coil 102** can be configured to surround native leaflets of the native valve (and the chordae tendineae that connects native leaflets to adjacent papillary muscles, if present), as described further below.

The docking device 100 can be releasably coupled to a delivery apparatus. For example, in certain examples, the docking device 100 can be coupled to a delivery apparatus (as described further below) via a release suture that can be configured to be tied to the docking device 100 and cut for removal. In one example, the release suture can be tied to the docking device 100 through an eyelet or eyehole 103 located adjacent the proximal end **102*p* of the coil. In another example, the release suture can be tied around a circumferential recess that is located adjacent the proximal end 102*p* of the coil 102**.

In some examples, the docking device 100 in the deployed configuration can be configured to fit at the mitral valve position. In other examples, the docking device can also be shaped and/or adapted for implantation at other native valve positions as well, such as at the tricuspid valve. As described herein, the geometry of the docking device 100 can be configured to engage the native anatomy, which can, for example, provide for increased stability and reduction of relative motion between the docking device 100, the prosthetic valve docked therein, and/or the native anatomy. Reduction of such relative motion can, among other things, prevent material degradation of components of the docking device 100 and/or the prosthetic valve docked therein and/or prevent damage or trauma to the native tissue.

As shown in FIGS. 1A-1B, the coil 102 in the deployed configuration can include a leading turn 106 (or "leading coil"), a central region 108, and a stabilization turn 110 (or "stabilization coil") around the central longitudinal axis 101. The central region 108 can possess one or more helical turns having substantially equal inner diameters. The leading turn 106 can extend from a distal end of the central region 108 and has a diameter greater than the diameter of the central region 108 (in one or more configurations). The stabilization turn 110 can extend from a proximal end of the central region 108 and has a diameter greater than the diameter of the central region 108 (in one or more configurations).

In certain examples, the central region 108 can include a plurality of helical turns, such as a proximal turn **108*p* in connection with the stabilization turn 110, a distal turn 108*d* in connection with the leading turn 106, and one or more intermediate turns 108*m* disposed between the proximal turn 108*p* and the distal turn 108*d*. In the example shown in FIG. 1A, there is only one intermediate turn 108*m* between the proximal turn 108*p* and the distal turn 108*d*. In other examples, there are more than one intermediate turns 108*m* between the proximal turn 108*p* and the distal turn 108*d*. Some of the helical turns in the central region 108 can be full turns (i.e., rotating 360 degrees). In some examples, the proximal turn 108*p* and/or the distal turn 108*d*** can be partial turns (e.g., rotating less than 360 degrees, such as 180 degrees, 270 degrees, etc.).

A size of the docking device 100 can be generally selected based on the size of the desired prosthetic valve to be implanted into the patient. In certain examples, the central region 108 can be configured to retain a radially expandable prosthetic valve (as shown in FIGS. 3A-3B and described further below). For example, the inner diameter of the helical turns in the central region 108 can be configured to be smaller than an outer diameter of the prosthetic valve when the prosthetic valve is radially expanded so that additional radial force can act between the central region 108 and the prosthetic valve to hold the prosthetic valve in place. As described herein, the helical turns (e.g., **108*p*, 108*m*, 108*d*) in the central region 108** are also referred to herein as "functional turns."

The stabilization turn 110 can be configured to help stabilize the docking device 100 in the desired position. For example, the radial dimension of the stabilization turn 110 can be significantly larger than the radial dimension of the coil in the central region 108, so that the stabilization turn 110 can flare or extend sufficiently outwardly so as to abut or push against the walls of the circulatory system, thereby improving the ability of the docking device 100 to stay in its desired position prior to the implantation of the prosthetic valve. In some examples, the diameter of stabilization turn 110 is desirably larger than the native annulus, native valve plane, and/or native chamber for better stabilization. In some examples, the stabilization turn 110 can be a full turn (i.e., rotating about 360 degrees). In some examples, the stabilization turn 110 can be a partial turn (e.g., rotating between about 180 degrees and about 270 degrees).

In one particular example, when implanting the docking device 100 at the native mitral valve location, the functional turns in the central region 108 can be disposed substantially in the left ventricle and the stabilization turn 110 can be disposed substantially in the left atrium. The stabilization turn 110 can be configured to provide one or more points or regions of contact between the docking device 100 and the left atrial wall, such as at least three points of contact in the left atrium or complete contact on the left atrial wall. In certain examples, the points of contact between the docking device 100 and the left atrial wall can form a plane that is approximately parallel to a plane of the native mitral valve.

In some examples, the stabilization turn 110 can have an atrial portion **110*a* in connection with the proximal turn 108*p* of the central region 108, a stabilization portion 110*c* adjacent to the proximal end 102*p* of the coil 102, and an ascending portion 110*b* located between the atrial portion 110*a* and the stabilization portion 110*c*. Both the atrial portion 110*a* and the stabilization portion 110*c* can be generally parallel to the helical turns in the central region 108, whereas the ascending portion 110*b* can be oriented to be angular relative to the atrial portion 110*a* and the stabilization portion 110*c*. For example, in certain examples, the ascending portion 110*b* and the stabilization portion 110*c* can form an angle from about 45 degrees to about 90 degrees (inclusive). In certain examples, the stabilization portion 110*c* can define a plane that is substantially parallel to a plane defined by the atrial portion 110*a*. A boundary 107 (marked by a dashed line in FIG. 1A) between the ascending portion 110*b* and the stabilization portion 110*c* can be determined as a location where the ascending portion 110*b* intersects the plane defined by the stabilization portion 110*c*. The curvature of the stabilization turn 110 can be configured so that the atrial portion 110*a* and the stabilization portion 110*c* are disposed on approximately opposite sides when the docking device 100 is fully expanded. When implanting the docking device 100 at the native mitral valve location, the atrial portion 110*a* can be configured to abut the posterior wall of the left atrium and the stabilization portion 110*c* can be configured to flare out and press against the anterior wall of the left atrium (see e.g., FIGS. 16-17 and 24**).

As noted above, the leading turn 106 can have a larger radial dimension than the helical turns in the central region 108. As described herein, the leading turn 106 can help more easily guide the coil 102 around and/or through the chordae tendineae and/or adequately around all native leaflets of the native valve (e.g., the native mitral valve, tricuspid valve, etc.). For example, once the leading turn 106 is navigated around the desired native anatomy, the remaining coil (such as the functional turns) of the docking device 100 can also be guided around the same features. In some examples, the leading turn 106 can be a full turn (i.e., rotating about 360 degrees). In some examples, the leading turn 106 can be a partial turn (e.g., rotating between about 180 degrees and about 270 degrees). As described further below in reference to FIG. 24, when a prosthetic valve is radially expanded within the central region 108 of the coil, the functional turns in the central region 108 can be further radially expanded. As a result, the leading turn 106 can be pulled in the proximal direction and become a part of the functional turn in the central region 108.

Figure 1C:
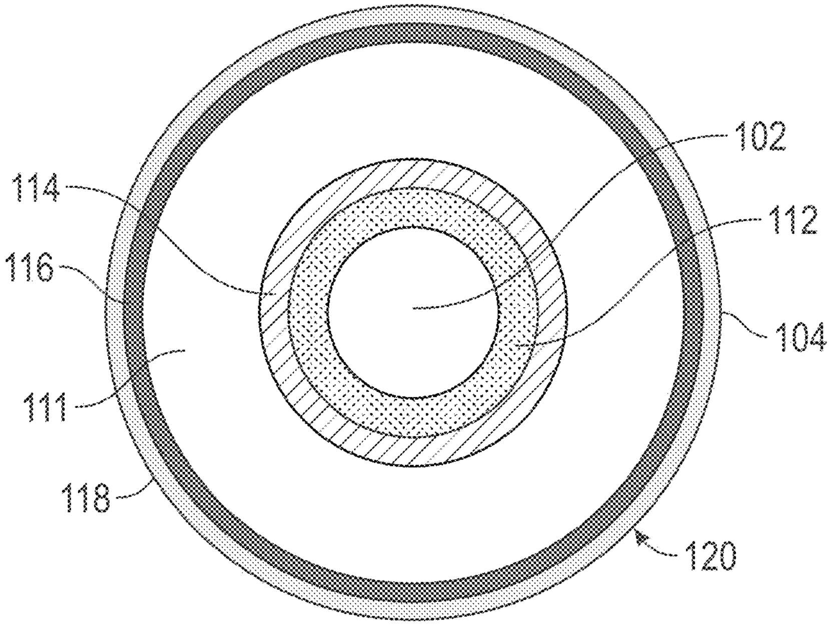
FIG. 1C is a cross-sectional view of the docking device taken along line 1C-1C depicted in FIG. 1B, according to one example.

In certain examples, at least a portion of the coil 102 can be surrounded by a first cover 112. As shown in FIGS. 1C-IF, the first cover 112 can have a tubular shape and thus can also be referred to as a "tubular member." In certain examples, the tubular member 112 can cover an entire length of the coil 102. In certain examples, the tubular member 112 covers only selected portion(s) of the coil 102.

In certain examples, the tubular member 112 can be coated on and/or bonded on the coil 102. In certain examples, the tubular member 112 can be a cushioned, padded-type layer protecting the coil. The tubular member 112 can be constructed of various native and/or synthetic materials. In one particular example, the tubular member 112 can include expanded polytetrafluoroethylene (ePTFE). In certain examples, the tubular member 112 is configured to be fixedly attached to the coil 102 (e.g., by means of textured surface resistance, suture, glue, thermal bonding, or any other means) so that relative axial movement between the tubular member 112 and the coil 102 is restricted or prohibited.

Figure 1D:
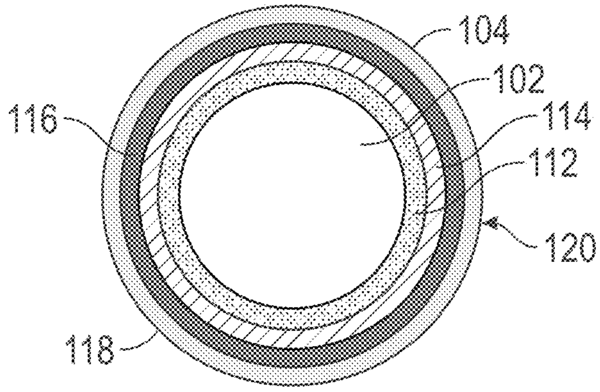
FIG. 1D is a cross-sectional view of the docking device taken along the same line as in FIG. 1C, except in FIG. 1D, the docking device is in a substantially straight delivery configuration.

In some examples, as illustrated in FIGS. 1C-1D, at least a portion of the tubular member 112 can be surrounded by the retention element 114. In some examples, the tubular member 112 can extend through an entire length of the retention element 114. Exemplary methods of attaching the retention element 114 to the tubular member 112 are described further below.

Figure 1E:
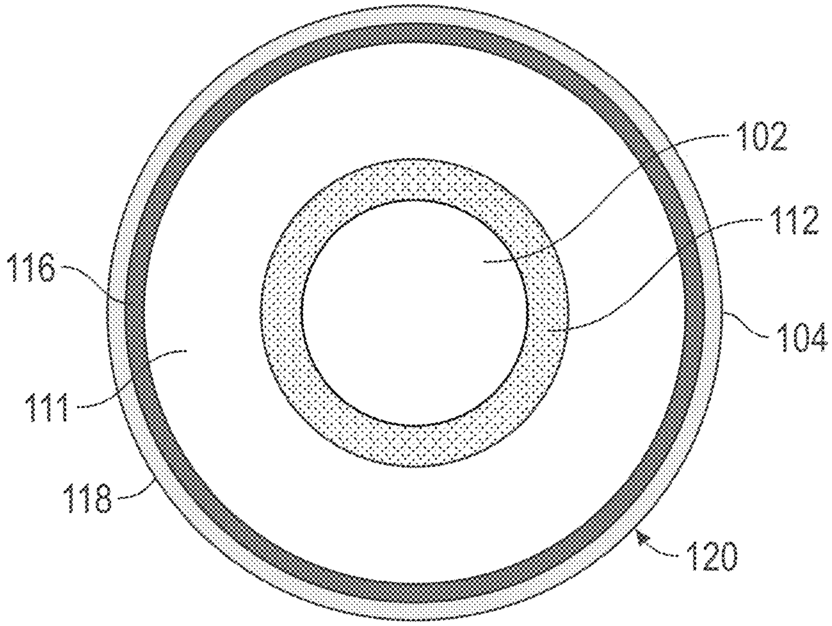
FIG. 1E is a cross-sectional view of the docking device taken along line 1C-1C depicted in FIG. 1B, according to another example.
Figure 1F:
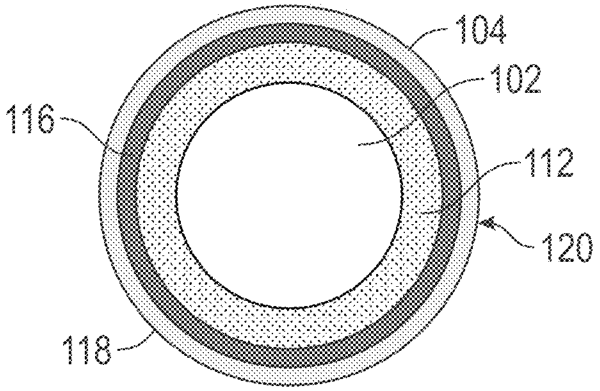
FIG. 1F is a cross-sectional view of the docking device taken along the same line as in FIG. 1E, except in FIG. 1F, the docking device is in a substantially straight delivery configuration.

In some examples, a distal end portion of the retention element 114 can extent axially beyond (i.e., positioned distal to) the distal end of the guard member 104, and a proximal end portion of the retention element 114 can extend axially beyond (i.e., positioned proximal to) the proximal end 105 of the guard member 104 to aid retention of prosthetic valve and tissue ingrowth. In one example, a distal end of the retention element 114 can be positioned adjacent the leading turn 106 (e.g., near the location marked by the dashed line 109 in FIG. 1A). In another example, the distal end of the retention element 114 can be disposed at or adjacent a distal end of the coil 102. In one example, a proximal end of the retention element 114 can be disposed at or adjacent the ascending portion 110*b* of the coil 102. In one example, as illustrated in FIGS. 1E-1F, at least a portion of the tubular member 112 may not be surrounded by the retention element 114.

In certain examples, the docking device 100 can have one or more seating markers. For example, FIGS. 1A-1B show a proximal seating marker 121*p* and a distal seating marker 121*d*, wherein the proximal seating marker 121*p* is positioned proximal relative to the distal seating marker 121*d*. Both the proximal and distal seating markers 121*p*, 121*d* can have predefined locations relative to the coil 102. As shown, both the proximal and distal seating markers 121*p*, 121*d* can be disposed distal to the ascending portion 110*b*, e.g., at the atrial portion 110*a*, of the coil 102. In addition, a proximal end portion of the retention element 114 can extend to, and/or positioned at, the ascending portion 110*b*.

In certain examples, both the proximal and distal seating markers 121*p*, 121*d* can include a radiopaque material so that these seating markers can be visible under fluoroscopy such as during an implantation procedure. As described further below, the seating markers 121*p*, 121*d* can be used to mark the proximal and distal boundaries of a segment of the coil 102 where the proximal end 105 of the guard member 104 can be positioned when deploying the docking device 100.

In certain examples, the seating markers 121*p*, 121*d* can be disposed on the tubular member 112 and covered by the retention element 114. In some examples, the seating markers 121*p*, 121*d* can be disposed on the atrial portion 110*a* of the coil 102 and covered by the tubular member 112. In particular examples, the seating markers 121*p*, 121*d* can be disposed directly on the retention element 114. In yet alternative examples, the seating markers 121*p*, 121*d* can be disposed on different layers relative to each other. For example, one of the seating markers (e.g., 121*p*) can be disposed outside the tubular member 112 and covered by the retention element 114, whereas another seating marker (e.g., 121*d*) can be disposed directly on the coil 102 and covered by the tubular member 112.

In certain examples, a segment of the coil 102 located between the proximal seating marker 121*p* and the distal seating marker 121*d* can have an axial length between about 2 mm and about 7 mm, or between about 3 mm and about 5 mm. In one specific example, the axial length of the coil segment between the proximal seating marker 121*p* and the distal seating marker 121*d* is about 4 mm.

In certain examples, an axial distance between the proximal seating marker 121*p* and a distal end of the ascending portion 110*b* is between about 10 mm and about 30 mm, or between about 15 mm and about 25 mm. In one specific example, the axial distance between the proximal seating marker 121*p* and the distal end of the ascending portion 110*b* is about 20 mm.

Although two seating markers 121*p*, 121*d* are shown in FIGS. 1A-1B, it is to be understood that the number of seating markers can be more than two or less than two. For example, in one example, the docking device 100 can have only one seating marker (e.g., 121*p*). In another example, one or more additional seating markers can be placed between the proximal and distal seating markers 121*p*, 121*d*. As noted above, the proximal end 105 of the guard member can be positioned between the proximal and distal seating markers 121*p*, 121*d* when deploying the docking device 100. As such, these additional seating markers can function as a scale to indicate a precise location of the proximal end 105 of the guard member 104 relative to the coil 102.

As described herein, the guard member 104 can constitute a part of a cover assembly 120 for the docking device 100. In some examples, the cover assembly 120 can also include the tubular member 112. In some examples, the cover assembly 120 can further include the retention element 114.

In some examples, as shown in FIGS. 1A-1B, when the docking device 100 is in the deployed configuration, the guard member 104 can be configured to cover a portion (e.g., the atrial portion 110*a*) of the stabilization turn 110 of the coil 102. In certain examples, the guard member 104 can be configured to cover at least a portion of the central region 108 of the coil 102, such as a portion of the proximal turn 108*p*. In certain examples, the guard member 104 can extend over the entirety of the coil 102.

As described herein, the guard member 104 can radially expand so as to help preventing and/or reducing paravalvular leakage. Specifically, the guard member 104 can be configured to radially expand such that an improved seal is formed closer to and/or against a prosthetic valve deployed within the docking device 100. In some examples, the guard member 104 can be configured to prevent and/or inhibit leakage at the location where the docking device 100 crosses between leaflets of the native valve (e.g., at the commissures of the native leaflets). For example, without the guard member 104, the docking device 100 may push the native leaflets apart at the point of crossing the native leaflets and allow for leakage at that point (e.g., along the docking device or to its sides). However, the guard member 104 can be configured to expand to cover and/or fill any opening at that point and inhibit leakage along the docking device 100.

In another example, when the docking device 100 is deployed at a native atrioventricular valve, the guard member 104 covers predominantly a portion of the stabilization turn 110 and/or a portion of the central region 108. In one example, the guard member 104 can cover predominantly the atrial portion 110*a* of the stabilization turn 110 that is located distal to the ascending portion 110*b*. Thus, the guard member 104 does not extend into the ascending portion 110*b* (or at least the guard member 104 can terminate before the anterolateral commissure 419 of the native valve, see e.g., FIGS. 16-17) when the docking device 100 is in the deployed configuration. In certain circumstances, the guard member 104 can extend onto the ascending portion 110*b*. This may cause the guard member 104 to kink, which (in some instances) may reduce the performance and/or durability of the guard member. Thus, the retention member 114 can, among other things, improve the functionality and/or longevity of the guard member 114 by preventing the guard member 104 from extending into the ascending portion 110*b* of the coil 102.

Yet in alternative examples, the guard member 104 can cover not only the atrial portion 110*a*, but can also extend over the ascending portion 110*b* of the stabilization turn 110. This can occur, e.g., in circumstances when the docking device is implanted in other anatomical locations and/or the guard member 104 is reinforced to reduce the risk of wire break.

In various examples, the guard member 104 can help covering an atrial side of an atrioventricular valve to prevent and/or inhibit blood from leaking through the native leaflets, commissures, and/or around an outside of the prosthetic valve by blocking blood in the atrium from flowing in an atrial to ventricular direction (i.e., antegrade blood flow)—other than through the prosthetic valve. Positioning the guard member 104 on the atrial side of the valve can additionally or alternatively help reduce blood in the ventricle from flowing in a ventricular to atrial direction (i.e., retrograde blood flow).

In some examples, the guard member 104 can be positioned on a ventricular side of an atrioventricular valve to prevent and/or inhibit blood from leaking through the native leaflets, commissures, and/or around an outside of the prosthetic valve by blocking blood in the ventricle from flowing in a ventricular to atrial direction (i.e., retrograde blood flow). Positioning the guard member 104 on the ventricular side of the valve can additionally or alternatively help reduce blood in the atrium from flowing in the atrial direction to ventricular direction (i.e., antegrade blood flow)—other than through the prosthetic valve.

The guard member 104 can include an expandable member 116 and a cover member 118 (also referred to as a "second cover" or an "outer cover") surrounding an outer surface of the expandable member 116. In certain examples, the expandable member 116 surrounds at least a portion of the tubular member 112. In certain examples, the tubular member 112 can extend (completely or partially) through the expandable member 116.

The expandable member 116 can extend radially outwardly from the coil 102 (and the tubular member 112) and is movable between a radially compressed (and axially elongated) state and a radially expanded (and axially foreshortened) state. That is, the expandable member 116 can axially foreshorten when it moves from the radially compressed state to the radially expanded state and can axially elongate when it moves from the radially expanded state to the radially compressed state.

In certain examples, the expandable member 116 can include a braided structure, such as a braided wire mesh or lattice. In certain examples, the expandable member 116 can include a shape memory material that is shape set and/or pre-configured to expand to a particular shape and/or size when unconstrained (e.g., when deployed at a native valve location). For example, the expandable member 116 can have a braided structure containing a metal alloy with shape memory properties, such as Nitinol or cobalt chromium. The number of wires (or fibers, strands, or the like) forming the braided structure can be selected to achieve a desired elasticity and/or strength of the expandable member 116. In certain examples, the number of wires used to braid the expanding member 116 can range from 16 to 128 (e.g., 48 wires, 64 wires, 96 wires, etc.). In certain examples, the braid density can range from 20 picks per inch (PPI) to 70 PPI, or from 25 PPI to 65 PPI. In one specific example, the braid density is about 36 PPI. In another specific example, the braid density is about 40 PPI. In certain examples, the diameter of the wires can range from about 0.002 inch to about 0.004 inch. In one particularly example, the diameter of the wires can be about 0.003 inch. In another example, the expandable member 116 can be a combination of braided Nitinol wire and textile (e.g., polyethylene terephthalate (PET), polytetrafluoroethylene (PTFE), etc.) yarns. In yet another example, the expandable member 116 can include a polymeric material, such as a thermoplastic material (e.g., PET, polyether ether ketone (PEEK), thermoplastic polyurethane (TPU), etc.), as described further below.

In certain examples, the expandable member 116 can include a foam structure. For example, the expandable member can include an expandable memory foam which can expand to a specific shape or specific pre-set shape upon removal of a crimping pressure (e.g., removal of the docking device 100 from the delivery sheath) prior to delivery of the docking device.

As described herein, the cover member 118 can be configured to be so elastic that when the expandable member 116 moves from the radially compressed (and axially elongated) state to the radially expanded (and axially foreshortened) state, the cover member 118 can also radially expand and axially foreshorten together with the expandable member 116. In other words, the guard member 104, as a whole, can move from a radially compressed (and axially elongated) state to a radially expanded (and axially foreshortened) state. As described herein, the radially expanded (and axially foreshortened) state is also referred to as the "relaxed state," and the radially compressed (and axially elongated) state is also referred to as the "collapsed state."

In certain examples, the cover member 118 can be configured to be atraumatic to native tissue and/or promote tissue ingrowth into the cover member 118. For example, the cover member 118 can have pores to encourage tissue ingrowth. In another example, the cover member 118 can be impregnated with growth factors to stimulate or promote tissue ingrowth, such as transforming growth factor alpha (TGF-alpha), transforming growth factor beta (TGF-beta), basic fibroblast growth factor (bFGF), vascular epithelial growth factor (VEGF), and combinations thereof. The cover member 118 can be constructed of any suitable material, including foam, cloth, fabric, and/or polymer, which is flexible to allow for compression and expansion of the cover member 118. In one example, the cover member 118 can include a fabric layer constructed from a thermoplastic polymer material, such as polyethylene terephthalate (PET).

As described herein, a distal end portion **104*d* of the guard member 104 (including a distal end portion of the expandable member 116 and a distal end portion of the cover member 118) can be fixedly coupled to the coil 102 (e.g., via suturing, gluing, or the like), and a proximal end portion 104*p* of the guard member 104 (including a proximal end portion of the expandable member 116 and a proximal end portion of the cover member 118) can be axially movable relative to the coil 102. Further, the proximal end portion of the expandable member 116 can be fixedly coupled to the proximal end portion of the cover member 118** (e.g., via suturing, gluing, thermal compression, laser fusion, etc.).

When the docking device 100 is retained within the delivery sheath in the substantially straight configuration, the expandable member 116 can be radially compressed by the delivery sheath and remains in the radially compressed (and axially elongated) state. The radially compressed (and axially elongated) expandable member 116 can contact the retention element 114 (sec, e.g., FIG. 1C) or the tubular member 112 (sec, e.g., FIG. 1E) so that no gap or cavity exists between the retention element 114 and the expandable member 116 or between the tubular member 112 (and/or the coil 102) and the expandable member 116.

After the docking device 100 is removed from the delivery sheath and changes from the delivery configuration to the deployed configuration, the guard member 104 can also move from a delivery configuration to a deployed configuration. In certain examples, a dock sleeve (which is described more fully below) can be configured to cover and retain the docking device 100 within the delivery sheath when navigating the delivery sheath through the patient's native valve. The docking sleeve can also, for example, help to guide the docking device around the native leaflets and chordae. Retraction of the dock sleeve relative to the docking device 100 can expose the guard member 104 and cause it to move from the delivery configuration to the deployed configuration. Specifically, without the constraint of the delivery sheath and the dock sleeve, the expandable member 116 can radially expand (and axially foreshorten) so that a gap or cavity 111 can be created between the retention element 114 and the expandable member 116 (see, e.g., FIG. 1C) and/or between the tubular member 112 and the expandable member 116 (see, e.g., FIG. 1E). Thus, when the guard member 104 is in the delivery configuration, an outer edge of the guard member 104 can extend along and adjacent the coil 102 (since there is no gap 111, only the retention element 114 and/or the tubular member 112 separate the coil 102 from the expandable member 116, as shown in FIG. 1D and FIG. 1F). When the guard member 104 is in the deployed configuration, the outer edge of the guard member 104 can form a helical shape rotating about the central longitudinal axis 101 (see, e.g., FIGS. 1A-1B and 3A-3B) and at least a segment of the outer edge of guard member can extend radially away from the coil 102 (e.g., due to the creation of the gap 111 between the expandable member 116 and the retention element 114 or the tubular member 112).

Because the distal end portion 104*d* of the guard member 104 is fixedly coupled to the coil 102 and the proximal end portion 104*p* of the guard member 104 can be axially moveable relative to the coil 102, the proximal end portion 104*p* of the guard member 104 can slide axially over the tubular member 112 and toward the distal end 102*d* of the coil 102 when expandable member 116 moves from the radially compressed state to the radially expanded state. As a result, the proximal end portion 104*p* of the guard member 104 can be disposed closer to the proximal end 102*p* of the coil 102 when the expandable member 116 is in the radially compressed state than in the radially expanded state.

In certain examples, the cover member 118 can be configured to engage with the prosthetic valve deployed within the docking device 100 so as to form a seal and reduce paravalvular leakage between the prosthetic valve and the docking device 100 when the expandable member 116 is in the radially expanded state. The cover member 118 can also be configured to engage with the native tissue (e.g., the native annulus and/or native leaflets) to reduce PVL between the docking device and/or the prosthetic valve and the native tissue.

In certain examples, when the expandable member 116 is in the radially expanded state, the proximal end portion 104*p* of the guard member 104 can have a tapered shape as shown in FIGS. 1A-1B, such that the diameter of the proximal end portion 104*p* gradually increases from a proximal end 105 of the guard member 104 to a distally located body portion of the guard member 104. This can, for example, help to facilitate loading the docking device into a delivery sheath of the delivery apparatus and/or retrieval and/or re-positioning of the docking device into the delivery apparatus during an implantation procedure. In addition, due to its small diameter, the proximal end 105 of the guard member 104 can frictionally engage with the retention element 114 so that the retention element 114 can reduce or prevent axial movement of the proximal end portion 104*p* of the guard member 104 relative to the coil 102.

In certain examples, the docking device 100 can include at least one radiopaque marker configured to provide visual indication about the location of the docking device 100 relative to its surrounding anatomy, and/or the amount of radial expansion of the docking device 100 (e.g., when a prosthetic valve is subsequently deployed in the docking device 100) under fluoroscopy. For example, one or more radiopaque markers can be placed on the coil 102. In one particular example, a radiopaque marker (which can be larger than the seating markers 121*p*, 121*d*) can be disposed at the central region 108 of the coil. In another example, one or more radiopaque markers can be placed on the tubular member 112, the expandable member 116, and/or the cover member 118. As noted above, the docking device 100 can also have one or more radiopaque markers (e.g., 121*p* and/or 121*d*) located distal to the ascending portion 110*b* of the coil 102. The radiopaque marker(s) used to provide visual indication about the location and/or the amount of radial expansion of the docking device 100 can be in addition to the seating markers (e.g., 121*p*, 121*d*) described above.

Figure 1G:
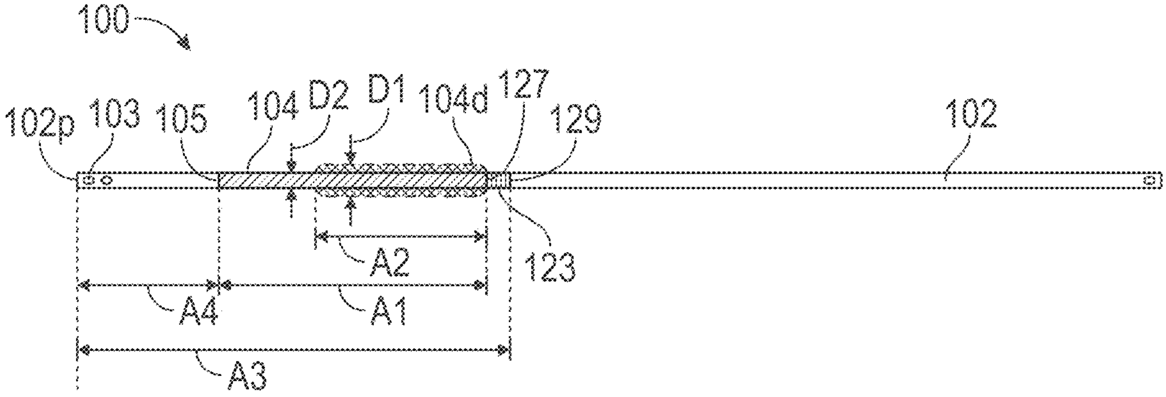
FIG. 1G is a schematic diagram depicting the docking device in a substantially straight configuration.

FIG. 1G schematically depicts some example dimensions of the docking device 100 when the coil 102 is in a substantially straight configuration (e.g., compared to the helical configuration depicted in FIG. 1A). The guard member 104 surrounding the coil 102 is shown in both the collapsed state (shown in solid contour) and the relaxed state (shown in dashed contour). In certain examples, the guard member 104 in the relaxed state can have a maximum outer diameter (D1) ranging from about 4 mm to about 8 mm (e.g., about 6 mm in one particular example), and the guard member 104 in the collapsed state can have a maximum outer diameter (D2) ranging from about 1 mm to about 3 mm (e.g., about 2 mm in one particular example). The expansion of the guard member 104 from the collapsed state to the relaxed state can be characterized by an expansion ratio defined as D1/D2. In certain examples, the expansion ratio can range from about 1.5 to about 8, or from about 2 to about 6, or from about 2.5 to about 4. In one specific example, the expansion ratio is about 3.

The distal end portion 104*d* of the guard member 104 can be fixedly attached to the coil 102, e.g., via sutures, gluing, or other means. The portion of the guard member 104 that is fixedly attached to the coil 102 can define a distal attachment region 123, which has a proximal end 127 and a distal end 129. Thus, only the portion of the guard member 104 that is proximal to the distal attachment region 123 is movable relative to the coil 102.

Returning again to FIG. 1G, in certain examples, when the guard member 104 is in the relaxed state, its movable portion (i.e., the portion extending from the proximal end 105 of the guard member 104 to the proximal end 127 of the distal attachment region 123) can have an axial length (A2) ranging from about 30 mm to about 100 mm. In one specific example, A2 is about 51 mm. In another specific example, A2 is about 81 mm. When the guard member 104 is in the collapsed state, its movable portion can have an axial length (A1) ranging from about 50 mm to about 120 mm. In one specific example, A1 is about 72 mm. In another specific example, A1 is between 105 mm and 106.5 mm. The elongation of the guard member 104 from the relaxed state to the collapsed state can be characterized by an elongation ratio defined as A1/A2. In certain examples, the elongation ratio can range from about 1.05 to about 1.7, or from about 1.1 to about 1.6, or from about 1.2 to about 1.5, or from 1.3 to about 1.4. In one specific example, the elongation ratio is about 1.47. In another specific example, the elongation ratio is about 1.31.

In certain examples, an axial length (A3) measured from the proximal end 102*p* of the coil 102 to the distal end 129 of the distal attachment region 123 can range from about 130 mm to about 200 mm, or from about 140 mm to about 190 mm. In one specific example, A3 is between 133 mm and 135 mm (e.g., 134 mm). In another specific example, A3 is between 178 mm and 180 mm (e.g., 179 mm). In certain examples, when the guard member 104 is in the collapsed state, an axial length (A4) measured from the proximal end 102*p* of the coil 102 to the proximal end 105 of the guard member 104 can range from about 40 mm to about 90 mm, or from about 50 mm to about 80 mm. In certain examples, A4 is between 60 mm and 70 mm (e.g., 61 mm).

Further details of the docking device and its variants, including various examples of the coil, the first cover (or tubular member), the second cover (or cover member), the expandable member, and other components of the docking device, are described in PCT Patent Application Publication No. WO/2020/247907, the entirety of which is incorporated by reference herein.

Exemplary Prosthetic Valves

Figure 2A:
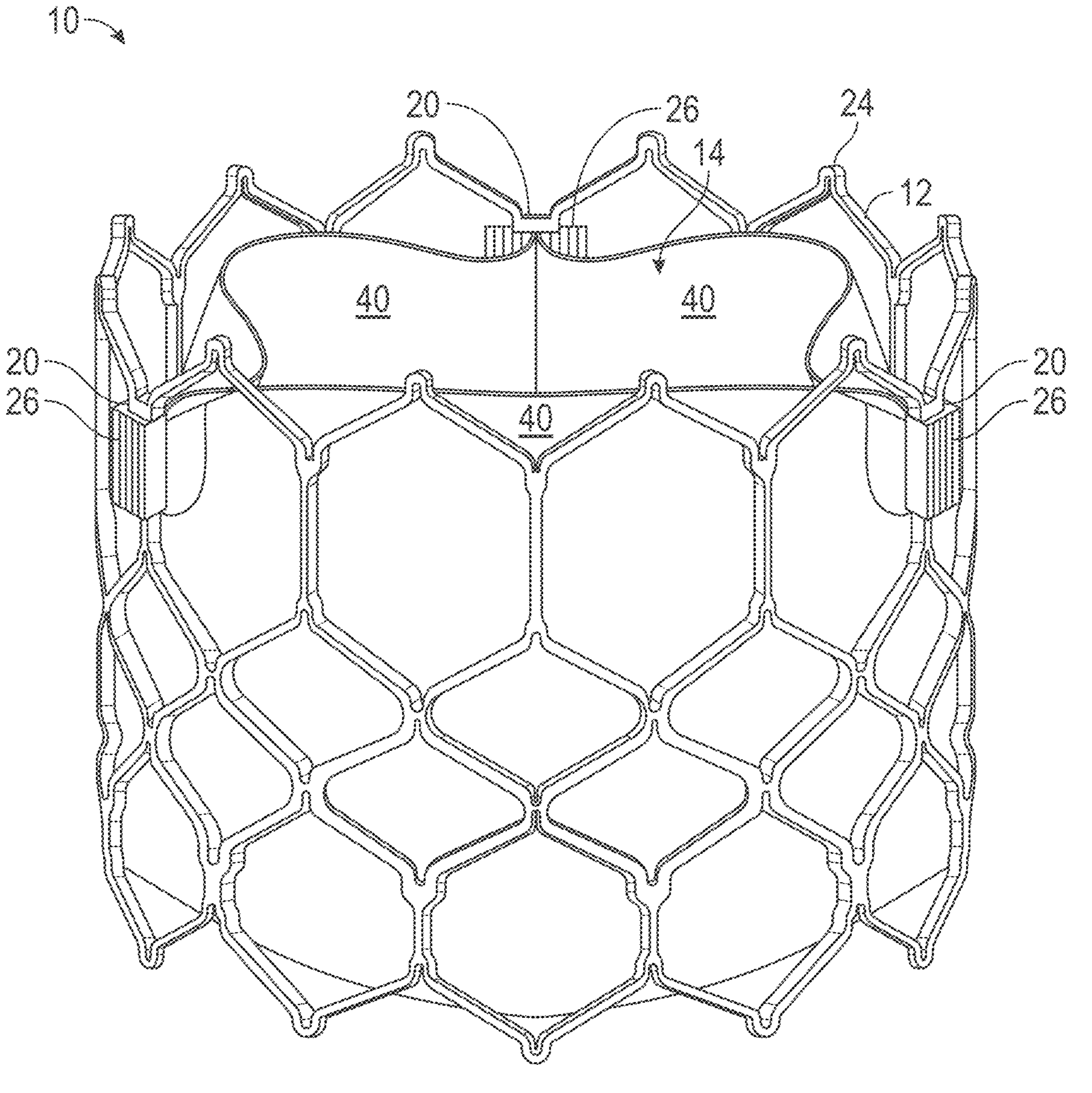
FIG. 2A is a perspective view a prosthetic valve, according to one example.
Figure 2B:
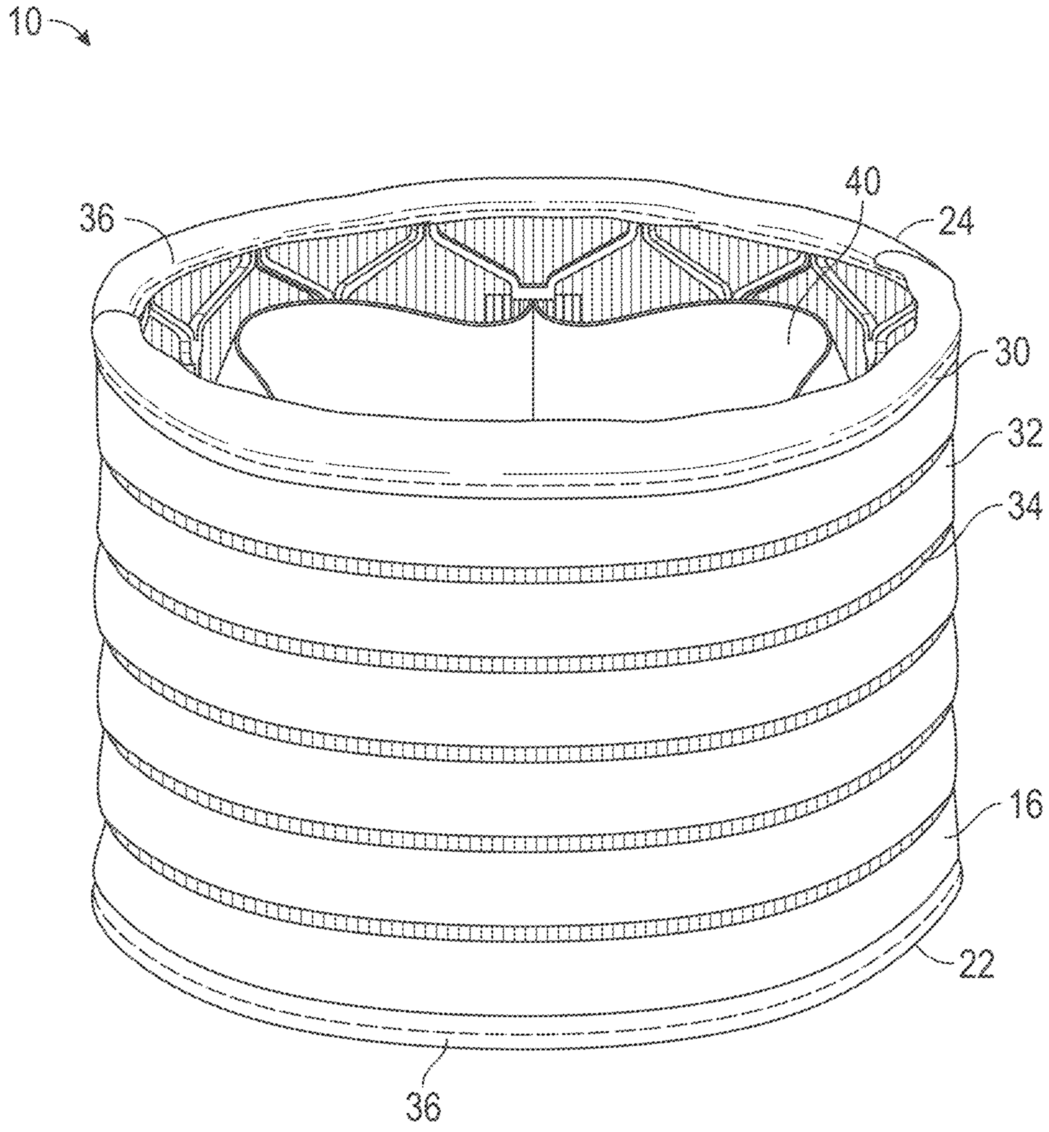
FIG. 2B is a perspective view of the prosthetic valve of FIG. 2A with an outer cover, according to one example.

FIGS. 2A-2B show a prosthetic valve 10, according to one example. The prosthetic valve 10 can be adapted to be implanted, with or without a docking device, in a native valve annulus, such as the native mitral valve annulus, native aortic annulus, native pulmonary valve annulus, etc. The prosthetic valve 10 can include a stent, or frame, 12, a valvular structure 14, and a valve cover 16 (the valve cover 16 is removed in FIG. 2A to show the frame structure).

The valvular structure 14 can include three leaflets 40, collectively forming a leaflet structure (although a greater or fewer number of leaflets can be used), which can be arranged to collapse in a tricuspid arrangement. The leaflets 40 are configured to permit the flow of blood from an inflow end 22 to an outflow end 24 of the prosthetic valve 10 and block the flow of blood from the outflow end 24 to the inflow end 22 of the prosthetic valve 10. The leaflets 40 can be secured to one another at their adjacent sides to form commissures 26 of the leaflet structure. The lower edge of valvular structure 14 desirably has an undulating, curved scalloped shape. By forming the leaflets 40 with this scalloped geometry, stresses on the leaflets 40 can be reduced, which in turn can improve durability of the prosthetic valve 10. Moreover, by virtue of the scalloped shape, folds and ripples at the belly of each leaflet 40 (the central region of each leaflet), which can cause early calcification in those areas, can be eliminated or at least minimized. The scalloped geometry can also reduce the amount of tissue material used to form leaflet structure, thereby allowing a smaller, more even crimped profile at the inflow end of the prosthetic valve 10. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 12 can be formed with a plurality of circumferentially spaced slots, or commissure windows 20 (three in the illustrated example) that are adapted to mount the commissures 26 of the valvular structure 14 to the frame. The frame 12 can be made of any of various suitable plastically expandable materials (e.g., stainless steel, etc.) or self-expanding materials (e.g., Nitinol) as known in the art. When constructed of a plastically expandable material, the frame 12 (and thus the prosthetic valve 10) can be crimped to a radially compressed state on a delivery apparatus and then expanded inside a patient by an inflatable balloon or equivalent expansion mechanism. When constructed of a self-expandable material, the frame 12 (and thus the prosthetic valve 10) can be crimped to a radially compressed state and restrained in the compressed state by insertion into a valve sheath or equivalent mechanism of a delivery apparatus. Once inside the body, the prosthetic valve 10 can be advanced from the delivery sheath, which allows the prosthetic valve 10 to expand to its functional size.

Suitable plastically expandable materials that can be used to form the frame 12 include, without limitation, stainless steel, a nickel-based alloy (e.g., a cobalt-chromium or a nickel-cobalt-chromium alloy), polymers, or combinations thereof. In particular examples, frame 12 can be made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form the frame 12 can provide superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

As shown in FIG. 2B, the valve cover 16 can include an outer portion 18 which can cover an entire outer surface of the frame 12. In certain examples, as shown in FIG. 3A, the valve cover 16 can also include an inner portion 28. The inner portion 28 can cover an entire inner surface of the frame 12, or alternatively, cover only selected portions of the inner surface of the frame 12. In the depicted example, the inner portion 28 is formed by folding the valve cover 16 over the outflow end 24 of the frame 12. In certain examples, a protective cover 36 comprising a high abrasion resistant material (e.g., ePTFE, etc.) can be placed over the fold of the valve cover 16 at the outflow end 24. In certain examples, similar protective cover 36 can be placed over the inflow end 22 of the frame. The valve cover 16 and the protective cover 36 can be affixed to the frame 12 by a variety of means, such as via sutures 30.

As described herein, the valve cover 16 can be configured to prevent paravalvular leakage between the prosthetic valve 10 and the native valve, to protect the native anatomy, to promote tissue ingrowth, among some other purposes. For mitral valve replacement, due to the general D-shape of the mitral valve and relatively large annulus compared to the aortic valve, the valve cover 16 can act as a seal around the prosthetic valve 10 (e.g., when the prosthetic valve 10 is sized to be smaller than the annulus) and allows for smooth coaptation of the native leaflets against the prosthetic valve 10.

In various examples, the valve cover 16 can include a material that can be crimped for transcatheter delivery of the prosthetic valve 10 and is expandable to prevent paravalvular leakage around the prosthetic valve 10. Examples of possible materials include foam, cloth, fabric, one or more synthetic polymers (e.g., polyethylene terephthalate (PET), polytetrafluoroethylene (PTFE), expanded polytetrafluoroethylene (cPTFE), etc.), organic tissues (e.g., bovine pericardium, porcine pericardium, equine pericardium, etc.), and/or an encapsulated material (e.g., an encapsulated hydrogel).

In certain examples, the valve cover 16 can be made of a woven cloth or fabric possessing a plurality of floated yarn sections 32 (e.g., protruding or puffing sections, also referred to as "floats" hereinafter). Details of exemplary covered valves with a plurality of floats 32 are further described in U.S. Patent Publication Nos. US2019/0374337, US2019/0192296, and US2019/0046314, the disclosures of which are incorporated herein in their entireties for all purposes. In certain examples, the float yarn sections 32 are separated by one or more horizontal bands 34. In some examples, the horizontal bands 34 can be constructed via a leno weave, which can improve the strength of the woven structure. In some examples of the woven cloth, vertical fibers (e.g., running along the longitudinal axis of the prosthetic valve 10) can include a yarn or other fiber possessing a high level of expansion, such as a texturized weft yarn, while horizontal fibers (e.g., running circumferentially around the prosthetic valve 10) in a leno weave can include a low expansion yarn or fiber.

In some examples, the valve cover 16 can include a woven cloth resembling a greige fabric when assembled and under tension (e.g., when stretched longitudinally on a compressed valve prior to delivery of a prosthetic valve 10). When the prosthetic valve 10 is deployed and expanded, tension on floats 32 is relaxed allowing expansion of the floats 32. In some examples, the valve cover 16 can be heat set to allow floats 32 to return to an enlarged, or puffed, space-filling form. In some examples, the number and sizes of floats 32 can be optimized to provide a level of expansion to prevent paravalvular leakage across the mitral plane (e.g., to have a higher level of expansion thickness) and/or a lower crimp profile (e.g., for delivery of the prosthetic valve). Additionally, the horizontal bands 34 can be optimized to allow for attachment of the valve cover 16 to the frame 12 based on the specific size or position of struts or other structural elements on the prosthetic valve 10.

Further details of the prosthetic valve 10 and its components are described, for example, in U.S. Pat. Nos. 9,393,110 and 9,339,384, which are incorporated by reference herein. Additional examples of the valve cover are described in PCT Patent Application Publication No. WO/2020/247907.

As described above and illustrated in FIGS. 3A-3B, the prosthetic valve 10 can be radially expanded and securely anchored within the docking device 100.

In certain examples, and as described further below in reference to FIGS. 21-22, the coil 102 of the docking device 100 in the deployed configuration can be movable between a first radially expanded configuration before the prosthetic valve 10 is radially expanded within the coil 102 and a second radially expanded configuration after the prosthetic valve 10 is radially expanded within the coil 102. In the example depicted in FIGS. 3A-3B, the coil 102 is in the second radially expanded configuration since the prosthetic valve 10 is shown in the radially expanded state.

As described herein, at least a portion of the coil 102, such as the central region 108, can have a larger diameter in the second radially expanded configuration than in the first radially expanded configuration (i.e., the central region 108 can be further radially expanded by radially expanding the prosthetic valve 10). As the central region 108 increases in diameter when the coil 102 moves from the first radially expanded configuration to the second radially expanded configuration, the functional turns in the central region 108 and the leading turn 106 can rotate circumferentially (e.g., in clockwise or counter-clockwise direction when viewed from the stabilization turn 110). Circumferential rotation of the functional turns in the central region 108 and the leading turn 106, which can also be referred to as "clocking," can slightly unwind the helical coil in the central region 108. Generally, the unwinding can be less a turn, or less than a half turn (i.e., 180 degrees). For example, the unwinding can be about 60 degrees and may be up to 90 degrees in certain circumstances. As a result, a distance between the proximal end 102*p* and the distal end 102*d* of the coil 102 measured along the central longitudinal axis of the coil 102 can be foreshorten.

In the example depicted in FIGS. 3A-3B (and FIG. 24), the proximal end 105 of the guard member 104 is shown to be positioned distal to the proximal seating marker 121*p*. In other examples, after the prosthetic valve 10 is radially expanded within the coil 102, the proximal end 105 of the guard member 104 can be positioned proximal to the proximal seating marker 121*p* (i.e., the proximal seating marker 121*p* is covered by the guard member 104) but remains distal to the ascending portion 110*b*.

Overview of Exemplary Cover Assembly

As described above, the docking device 100 can have a cover assembly 120 including the tubular member 112 and the guard member 104, and in some instances the retention element 114. The guard member 104 can further include the expandable member 116 and the cover member 118. As described herein, the cover member 118 can be fixedly coupled to the expandable member 116 so that the cover member 118 can radially expand and axially foreshorten together with the expandable member 116.

In one example, the cover assembly 120 can be assembled by fixedly attaching the distal end portion 104*d* of the guard member 104 to the coil 102 (and the tubular member 112 surrounding the coil 102) while leaving the proximal end portion 104*p* of the guard member 104 unattached to the coil 102 (and the tubular member 112 surrounding the coil 102). Thus, the proximal end portion 104*p* can be axially movable relative to the coil 102 and the tubular member 112. As a result, when the coil 102 moves from the delivery configuration to the deployed configuration (e.g., during the initial deployment of the docking device 100), the proximal end portion 104*p* of the guard member 104 can slide distally over the coil 102 to cause the guard member 104 to contract axially (i.e., with decrease of axial length) while it expands radially (i.e., with increase in diameter).

On the other hand, the retention element 114, by applying a friction force (e.g., the frictional interaction between the retention element 114 and the proximal end 105 of the guard member 104), can limit the extent of distal movement of the proximal end portion 104*p* relative to the coil 102. For example, if the proximal end portion 104*p* of a fully expanded guard member 104 (i.e., expanding to its largest diameter) can slide distally over the coil 102 to a first location in the absence of retention element 114, then the presence of the retention element 114 can cause the proximal end portion 104*p* to slide distally over the coil 102 to a second location that is proximal to the first location. In other words, the retention element 114 can prevent the guard member 104 to expand to its largest diameter and/or contract to its shortest axial length.

Similarly, the retention element 114, by exerting a friction force (e.g., the frictional interaction between the retention element 114 and the proximal end 105 of the guard member 104), can limit the extent of proximal movement of the proximal end portion 104*p* relative to the coil 102. As noted above and described further below, the coil 102 of the docking device 100 in the deployed configuration can be further radially expanded (e.g., moving from the first radially expanded configuration to the second radially expanded configuration) when the prosthetic valve 10 is radially expanded within the coil 102, and radial expansion of the coil 102 can cause corresponding circumferential rotation of the coil 102. The radially expanded prosthetic valve 10 can press against the guard member 104, causing the guard member 104 to be radially compressed and axially extended. Because the distal end portion 104*d* of the guard member 104 is fixedly attached to the coil 102 and the proximal end portion 104*p* of the guard member 104 is untethered to the coil 102, the proximal end portion 104*p* of the guard member 104 can have a tendency to move proximally relative to the coil 102 when the prosthetic valve 10 is radially expanded within the coil 102. However, the presence of the retention element 114 can impede the proximal end portion 104*p* of the guard member 104 to move proximally over the coil 102. In specific examples, the presence of the retention element 114 can prevent the proximal end 105 of the guard member 104 from extending onto the ascending portion 110*b* of the coil 102. This can, for example, improve the functionality and/or durability of the guard member 104, as discussed above.

The guard member 104 can be coupled to the coil 102 and/or tubular member 112 in various ways such as adhesive, fasteners, welding, and/or other means for coupling. For example, in some cases, attaching the cover member 118 to the expandable member 116 or attaching the distal end portion 104*d* of the guard member to the coil 102 and the tubular member 112 can be achieved by using one or more sutures. However, there are several technical challenges when using the sutures. First, when the expandable member 116 has a meshed wire frame made of certain metal or metal alloy (e.g., Nitinol), sewing the sutures with a needle may scratch the surface of the metal or metal alloy and increase the risk of corrosion for the wire frame when exposed to the bodily fluid, especially if the needle is also made of metal. Sewing the sutures with a non-metal needle (e.g., a plastic needle) has its own disadvantages because the non-metal needle typically has less strength compared to a metal needle, thus making it difficult to thread through various layers of the cover assembly 120. Further, even a non-metal needle can damage the surface of the metal or metal alloy of the wire frame. Second, the routing of sutures can be challenging because the sutures not only must ensure secure attachment between components of the cover assembly 120, but also not significantly increase the radial profile of the guard member 104 so that the docking device 100 can be retained in a delivery sheath of a delivery apparatus for transcatheter implantation.

An example method of assembling the guard member 104 is described in Provisional U.S. Application No. 63/252,524, the entirety of which is incorporated by reference herein. The method described therein (also referred to as the "stitching method" hereinafter) overcomes the challenges described above by forming a plurality of knots and wraps with sutures at both the proximal end portion 104*p* and distal end portion 104*d* of the guard member 104.

For example, in the stitching method, two separate processes can be used to prepare the expandable member 116 and the cover member 118. Specifically, to prepare the expandable member 116, a wire (e.g., Nitinol) is first braided onto a straight mandrel and then heat is applied to shape-set the braided wire to a straight configuration. Such straight-shaped braided wire can be reconfigured to generate a tapered proximal end portion (so that the proximal end portion 104*p* of the guard member 104 can have a tapered shape as shown in FIGS. 1A-1B). Such reconfiguration can be achieved by transferring the braided wire to a tapered mandrel (i.e., one end of the mandrel has a tapered shape), and then reapplying heat to shape-set the braided wire to create the tapered end portion. To prepare the cover member 118, the same steps described above for the expandable member 116 can be repeated. In other words, the cover material (e.g., PET) is first braided onto a straight mandrel, then a heat is applied to shape-set the braided cover to a straight configuration. Then, the straight-shaped braided cover is transferred to a tapered mandrel, and heat is reapplied to shape-set the braided cover to create a tapered end portion matching that of the expandable member 116. These two separate processes prepare the expandable member 116 and the cover member 118.

As another example, the stitching method involves attaching a proximal end portion of the expandable member 116 to a proximal end portion of the cover member 118 via a proximal suture. In some instances, the proximal suture can be used to connect each looped wire at the proximal end of the expandable member 116 to adjacent strands of yarns or filaments of the cover member 118 via a stitch so as to form a stitch loop around the proximal end of the expandable member 116.

Alternative processes of assembling a guard member are described below.

Exemplary Method of Assembling Guard Member

According to certain examples, the guard member 104 can have a multi-layer structure comprising a braided inner layer and a braided outer layer, where the inner layer and the outer layer can be fused with each other at a proximal end and a distal end of the guard member 104.

Specifically, the expandable member 116 can form the inner layer and can comprise a polymeric material, such as a thermoplastic material (e.g., PET, PEEK, TPU, etc.). The cover member 118 can form the outer layer and can comprise another polymeric material, such as a thermoplastic material (e.g., PET, etc.). In certain examples, the inner layer and the outer layer can comprise the same material (e.g., PET). In other examples, the inner layer and the outer layer can comprise different materials (e.g., the inner layer can comprise PEEK while the outer layer can comprise PET).

As described herein, the inner layer can be braided using fibers/yarns that are larger or thicker than fibers/yarns used to braid the outer layer so that the inner layer can as a skeleton for the guard member 104 and provide a sufficient strength and crush resistance for the guard member 104. As an example, the inner layers can be braided using plastic monofilament PET fibers/yarns having a diameter ranging between 0.001 inch and 0.005 inch, or between 0.002 inch and 0.004 inch (e.g., 0.003 inch).

In certain examples, the inner layer comprises a smaller number of fibers/yarns compared to the outer layer. For example, the inner layer can be braided using between 32 and 64 (e.g., 48) fibers/yarns, and the outer layer can be braided using between 80 and 112 (e.g., 96) fibers/yarns. In addition, the outer layer can be braided using multifilament fibers/yarns. For example, the number of filaments in a fiber/yarn of the outer layer can range between 12 and 36, or between 18 and 32. In one specific example, the outer layer can be braided using 40 denier, 24-filament PET fibers/yarns. Using a denser but smaller yarns for the outer layer can cause the guard member 104 to have a smoother/softer outer surface, and the denser fabric of the outer layer can also make the guard member more effective to block the blood flow, thus reducing paravalvular leakage.

Figure 4:
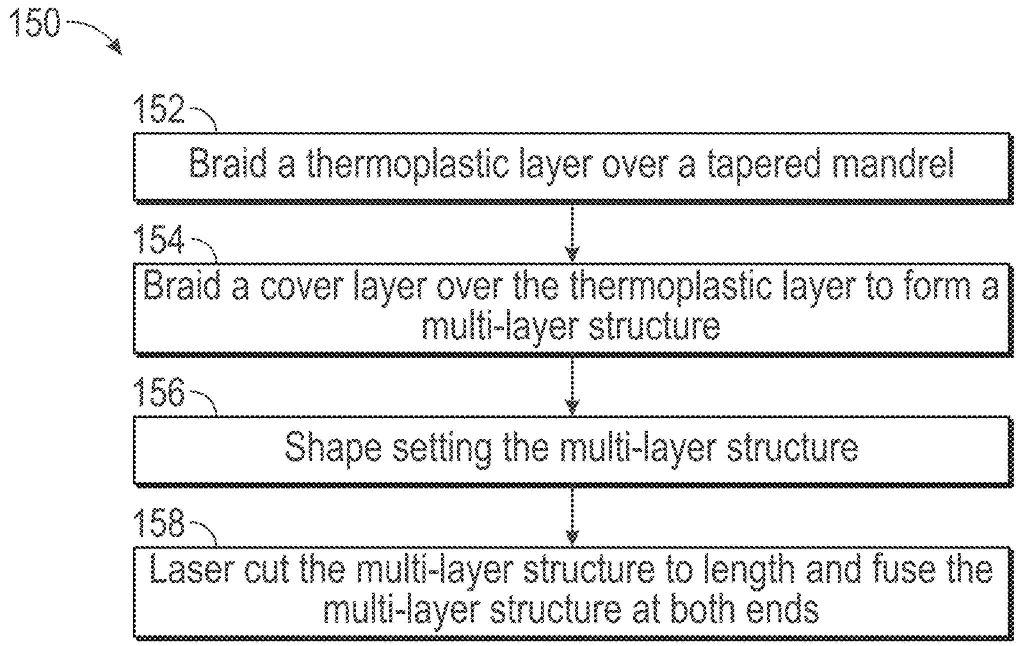
FIG. 4 is a flowchart depicting a method of forming a paravalvular leakage guard, according to one example.

FIG. 4 is a flowchart 150 depicting a method of forming a guard member 104, according to one example. At 152, a thermoplastic layer (which forms the expandable member 116) can be braided over a tapered mandrel. At 154, a cover layer (which forms the cover member 118) can be braided over the thermoplastic layer to form a multi-layer structure. At 156, the multi-layer structure can be shape set so as to conform to a shape of the mandrel. At 158, the multi-layer structure can be laser cut to length, and the multi-layer structure can fuse at both ends because of the laser cutting.

Figure 5A:
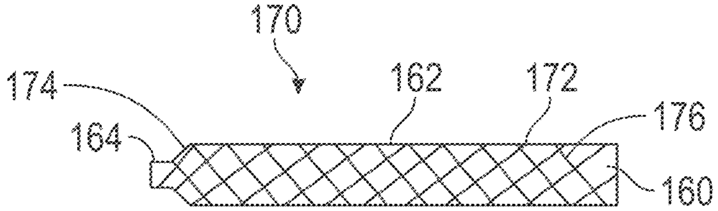
FIG. 5A depicts braiding a thermoplastic layer over a tapered mandrel, according to one example.
Figure 5B:
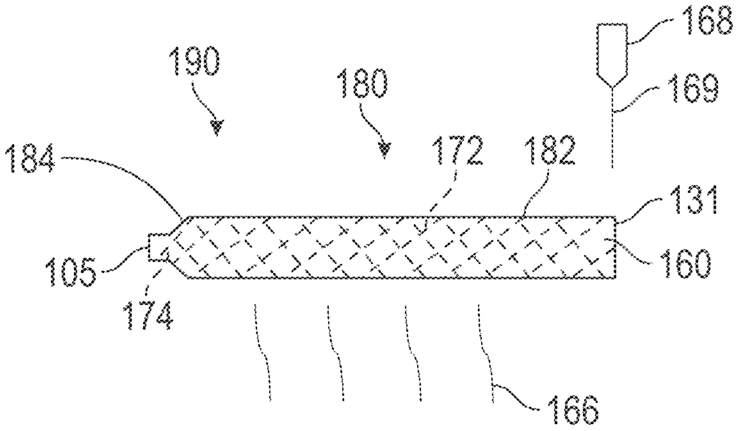
FIG. 5B depicts braiding an outer cover layer over the thermoplastic layer of FIG. 5A.

The method of forming the guard member 104 is further illustrated in FIGS. 5A-5B. FIG. 5A depicts a thermoplastic layer 170 comprising thermoplastic fibers 176 (e.g., PET fibers) braided over a tapered mandrel 160. As shown, the tapered mandrel 160 has a generally cylindrical body portion 162 and a tapered end portion 164. A first portion 172 of the thermoplastic layer 170 can be braided over the cylindrical body portion 162, and a second portion 174 of the thermoplastic layer 170 can be braided over the tapered end portion 164.

FIG. 5B depicts a cover layer 180 comprising another type of thermoplastic polymeric fibers (e.g., PET fibers) braided over the thermoplastic layer 170. As shown, a first portion 182 of the cover layer 180 can be braided over the first portion 172 of the thermoplastic layer 170, and a second portion 184 of the cover layer 180 can be braided over the second portion 174 of the thermoplastic layer 170. Thus, the thermoplastic layer 170 and the cover layer 180 can form a multi-layer structure 190 over the tapered mandrel 160.

After forming the multi-layer structure 190, heat 166 can be applied to shape set the multi-layer structure 190 to the shape of the mandrel 160. Specifically, the multi-layer structure 190 can be heated at a predetermined temperature over a predetermined duration so that the first portion 172 of the thermoplastic layer 170 and the first portion 182 of the cover layer 180 can conform to the cylindrical body portion 162 of the mandrel 160, while the second portion 174 of the thermoplastic layer 170 and the second portion 184 of the cover layer 180 can conform to the tapered end portion 164 of the mandrel 160.

After shape setting, the multi-layer structure 190 can be cut to length (i.e., a desired length of the guard member 104) to give it a proximal end 105 and a distal end 131. As shown, the proximal end 105 is located at the tapered end portion 164 of the mandrel 160 and the distal end 131 is located at the cylindrical body portion 162 of the mandrel 160.

In certain examples, cutting of the multi-layer structure 190 can be achieved by using a laser cutter 168 configured to emit a laser beam 169 directed at the proximal end 105 and/or the distal end 131, respectively. The laser beam 169 can heat and melt the thermoplastic fibers in layers 170 and 180 at the proximal end 105 and the distal end 131. The melted thermoplastic fibers of the layers 170 and 180 can flow together such that they contact each other and/or intermix. After curing, the thermoplastic fibers can fuse the thermoplastic layer 170 with the cover layer 180 at the proximal end 105 and the distal end 131.

In other examples, cutting of the multi-layer structure 190 can be achieved by other means (e.g., using a cutting blade), and the fusing of the layers 170 and 180 at the proximal end 105 and distal end 131 can also be achieved by other means for melting the materials (e.g., ultrasonic welding, etc.).

To assemble the docking device 100, the cut-to-length multi-layer structure 190, with fused proximal end 105 and distal end 131, can be removed from the mandrel 160 and attached to the coil 102, thereby forming the guard member 104, which can reduce paravalvular leakage around a prosthetic valve received in the docking device. As described above, the distal end 131 of the guard member 104 can be fixedly attached to the coil 102, and the proximal end 105 of the guard member 104 can be movable relative to the coil 102. Further, when the guard member moves from the radially compressed state to the radially expanded state, the proximal end 105 of the guard member 104 can slide distally over the coil 102.

The process depicted in FIGS. 4 and 5A-5B can, for example, reduce the manufacturing time and/or processes. It can also provide a relatively simple means for forming the guard member.

The multi-layer structure depicted herein has two layers. In other examples, a multi-layer structure can comprise more than two (e.g., 3-5) layers. The additional layers can be disposed radially inward of the expandable member, between the expandable member and the cover member, and/or radially outward of the cover member.

Exemplary Delivery Apparatus

Figure 6:
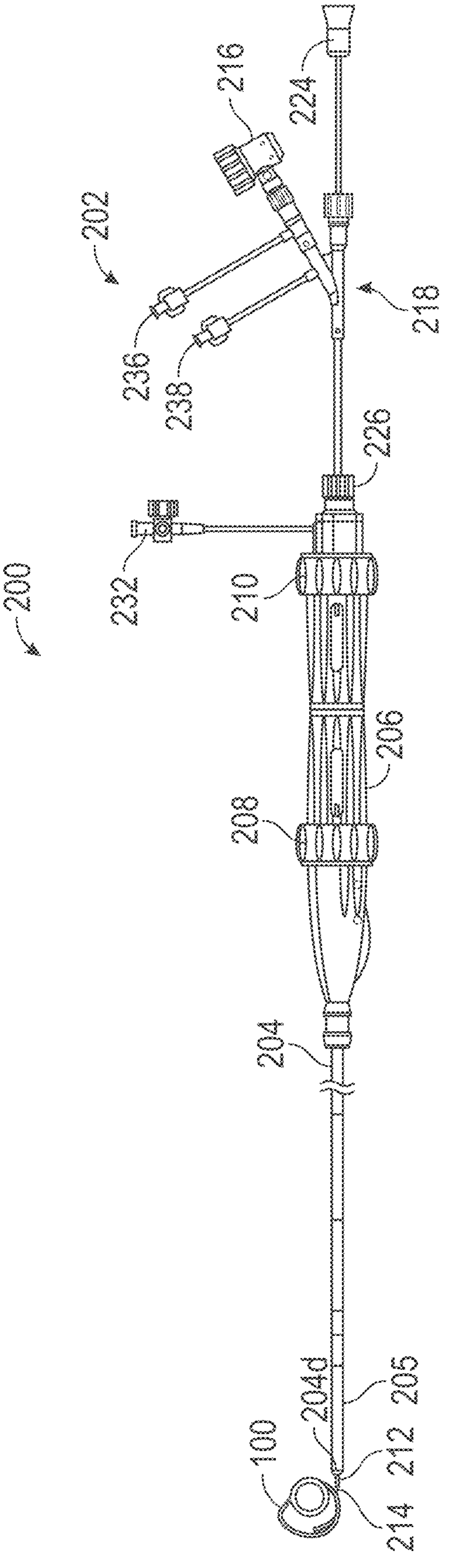
FIG. 6 is a side view of a delivery assembly comprising a delivery apparatus and the docking device of FIG. 1A, according to one example.

FIG. 6 shows a delivery apparatus 200 configured to implant a docking device, such as the docking device 100 described above or other docking devices, to a target implantation site in a patient, according to one example. Thus, the delivery apparatus 200 can also be referred to as a "dock delivery catheter" or "dock delivery system."

As shown, the delivery apparatus 200 can include a handle assembly 202 and a delivery sheath 204 (also referred to as the "delivery shaft" or "outer shaft" or "outer sheath") extending distally from the handle assembly 202. The handle assembly 202 can include a handle 206 including one or more knobs, buttons, wheels, and/or other means for controlling and/or actuating one or more components of the delivery apparatus 200. For example, in some examples, as shown in FIG. 6, the handle 206 can include knobs 208 and 210 which can be configured to steer or control flexing of the delivery apparatus 200 such as the delivery sheath 204 and/or the sleeve shaft 220 described below.

In certain examples, the delivery apparatus 200 can also include a pusher shaft 212 (sec e.g., FIG. 7B) and a sleeve shaft 220 (see e.g., FIG. 7A), both of which can extend through an inner lumen of the delivery sheath 204 and have respective proximal end portions extending into the handle assembly 202.

As described below, a distal end portion (also referred to as "distal section") of the sleeve shaft 220 can include a lubricous dock sleeve 222 configured to cover (e.g., surround) the docking device 100. For example, the docking device 100 (including the guard member 104) can be retained inside the dock sleeve 222, which is further retained by a distal end portion 205 of the delivery sheath 204, when navigating through a patient's vasculature. As noted above, the docking device 100 retained within the delivery sheath 204 can remain in the delivery configuration. Similarly, the guard member 104 retained within the dock sleeve 222 can also remain in the delivery configuration.

Figure 12:
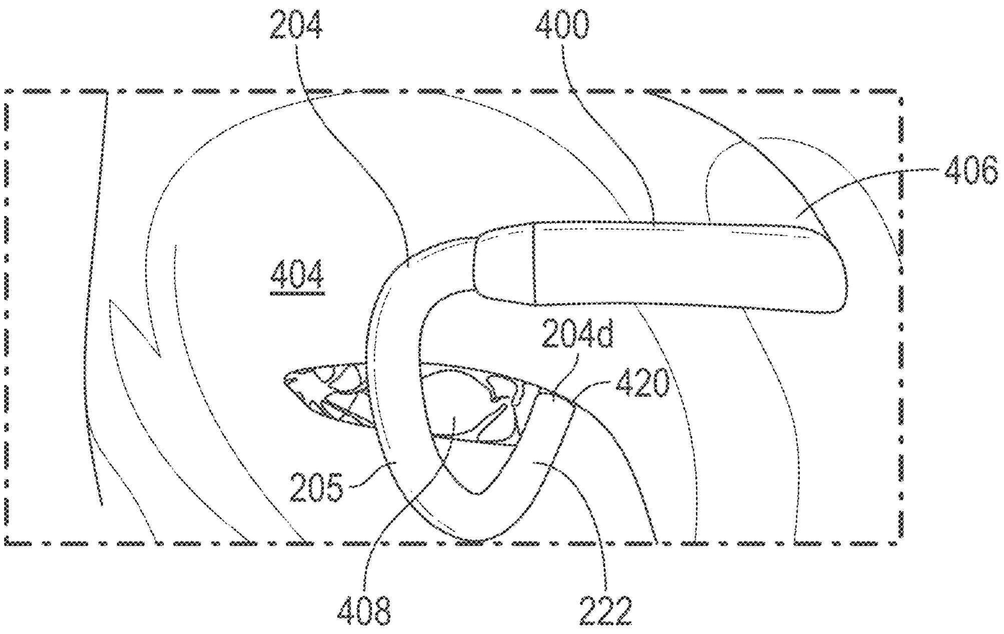

Additionally, the distal end portion 205 of the delivery sheath 204 can be configured to be steerable. In one example, by rotating a knob (e.g., 208 or 210) on the handle 206, a curvature of the distal end portion 205 can be adjusted so that the distal end portion 205 of the delivery sheath 204 can be oriented in a desired angle. For example, as shown in FIG. 12 and described below, to implant the docking device 100 at the native mitral valve location, the distal end portion 205 of the delivery sheath 204 can be steered in the left atrium so that the dock sleeve 222 and the docking device 100 retained therein can extend through the native mitral valve annulus at a location adjacent the posteromedial commissure.

In certain examples, the pusher shaft 212 and the sleeve shaft 220 can be coaxial with one another, at least within the delivery sheath 204. In addition, the delivery sheath 204 can be configured to be axially movable relative to the sleeve shaft 220 and the pusher shaft 212. As described further below, a distal end of the pusher shaft 212 can be inserted into a lumen of the sleeve shaft 220 and press against the proximal end (e.g., 102*d*) of the docking device 100 retained inside the dock sleeve 222.

After reaching a target implantation site, the docking device 100 can be deployed from the delivery sheath 204 by manipulating the pusher shaft 212 and sleeve shaft 220 using a hub assembly 218, as described further below. For example, by pushing the pusher shaft 212 in the distal direction while holding the delivery sheath 204 in place or retracting the delivery sheath 204 in the proximal direction while holding the pusher shaft 212 in place, or pushing the pusher shaft 212 in the distal direction while simultaneously retracting the delivery sheath 204 in the proximal direction, the docking device 100 can be pushed out of a distal end 204*d* of the delivery sheath 204, thus changing from the delivery configuration to the deployed configuration. In certain examples, the pusher shaft 212 and the sleeve shaft 220 can be actuated independently of each other.

In certain examples, when deploying the docking device 100 from the delivery sheath 204, the pusher shaft 212 and the sleeve shaft 220 can be configured to move together, in the axial direction, with the docking device 100. For example, actuation of the pusher shaft 212, to push against the docking device 100 and move it out of the delivery sheath 204 can also cause the sleeve shaft 220 to move along with the pusher shaft 212 and the docking device 100. As such, the docking device 100 can remain being covered by the dock sleeve 222 of the sleeve shaft 220 during the procedure of pushing the docking device 100 into position at the target implantation site via the pusher shaft 212. Thus, when the docking device 100 is initially deployed at the target implantation site, the lubricous dock sleeve 222 can facilitate the covered docking device 100 to encircle the native anatomy.

During delivery, the docking device 100 can be coupled to the delivery apparatus 200 via a release suture 214 (or other retrieval line comprising a string, yarn, or other material that can be configured to be tied around the docking device 100 and cut for removal) that extends through the pusher shaft 212. In one specific example, the release suture 214 can extend through the delivery apparatus 200, e.g., through an inner lumen of the pusher shaft 212, to a suture lock assembly 216 of the delivery apparatus 200.

The handle assembly 202 can further include a hub assembly 218 to which the suture lock assembly 216 and a sleeve handle 224 are attached. The hub assembly 218 can be configured to independently control the pusher shaft 212 and the sleeve shaft 220 while the sleeve handle 224 can control an axial position of the sleeve shaft 220 relative to the pusher shaft 212. In this way, operation of the various components of the handle assembly 202 can actuate and control operation of the components arranged within the delivery sheath 204. In some examples, the hub assembly 218 can be coupled to the handle 206 via a connector 226.

The handle assembly 202 can further include one or more flushing ports (e.g., three flushing ports 232, 236, 238 are shown in FIG. 6) to supply flush fluid to one or more lumens arranged within the delivery apparatus 200 (e.g., annular lumens arranged between coaxial components of the delivery apparatus 200), as described below.

Further details on delivery apparatus/catheters/systems (including various examples of the handle assembly) that are configured to deliver a docking device to a target implantation site can be found in U.S. Patent Publication Nos. 2018/0318079 and 2018/0263764, which are all incorporated by reference herein in their entireties.

Exemplary Sleeve Shaft

Figure 7A:
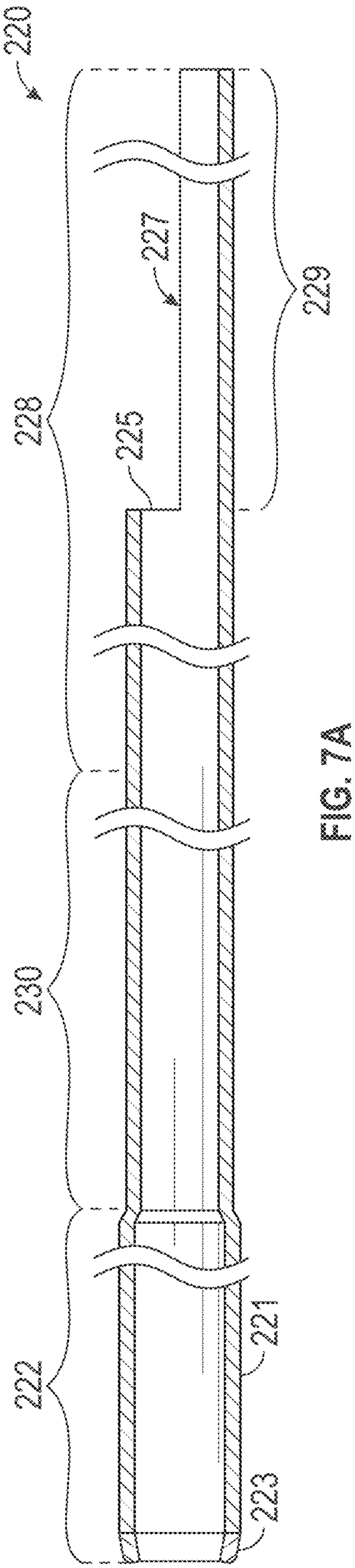
FIG. 7A is a side cross-sectional view of a sleeve shaft, according to one example.

FIG. 7A shows a sleeve shaft 220, according to one example. In some examples, the sleeve shaft 220 can have a lubricous distal section 222 (also referred to as the "dock sleeve" herein) configured to cover a docking device (e.g., 100) during deployment, a proximal section 228 used to manipulate or actuate position of the distal section 222, and a middle section 230 connecting the distal section 222 and the proximal section 228.

In some examples, the dock sleeve 222 can be configured to be flexible, have a lower durometer than the remainder of the sleeve shaft 220, and have a hydrophilic coating, which can act as a lubricous surface to improve the case of encircling the native anatomy and reduce risk of damage to the native tissue. In some examples, the dock sleeve 222 can form a tubular structure which has an inner diameter sufficient to surround the docking device 100 and an outer diameter that is small enough to be retained within and axially movable within the delivery sheath 204. In some examples, the outer diameter of the dock sleeve 222 can be slightly larger than the outer diameter of the middle section 230. In some examples, the length of the dock sleeve 222 is sufficient to cover or longer than the full length of the docking device 100 when it is retained inside the dock sleeve 222.

The dock sleeve 222 can have a body portion 221 and a tip portion 223 located at a distal end of the body portion 221. In some examples, the tip portion 223 can extend about 1-4 mm (e.g., about 2 mm) distally from the distal end of the body portion 221. In some examples, the tip portion 223 can taper radially inwardly such that it has a smaller diameter than the body portion 221. In some examples, during delivery, the tip portion 223 can extend past the distal end (e.g., 102*d*) of the docking device, thereby providing the dock sleeve 222 with a more atraumatic tip that can bend, squeeze, deform, or the like, as it is navigated around the native architecture of the implantation site for the docking device.

Additional examples of the dock sleeve, including various features of the body portion and tip portion of the dock sleeve, are described further in Provisional U.S. Application No. 63/138,910, the entirety of which is incorporated by reference herein.

In some examples, the middle section 230 of the sleeve shaft 220 can be configured to provide a sufficient column strength so as to push the dock sleeve 222 (with the docking device 100) out of a distal end 204*d* of the delivery sheath 204, and/or retract the dock sleeve 222 after the docking device 100 is deployed at the target implantation site. The middle section 230 can also be configured to have an enough flexibility so as to facilitate navigating the anatomy of a patient from the point of insertion of the delivery apparatus 200 to the heart. In certain examples, the dock sleeve 222 and the middle section 230 can be formed as a single, continuous unit with varying properties (e.g., dimensions, polymers, braids, etc.) along the length of the singular unit.

In some examples, a proximal portion of the proximal section 228 can be arranged in the handle assembly 202. The proximal section 228 of the sleeve shaft 220 can be configured to be more rigid and provide column strength to actuate the position of the dock sleeve 222 by pushing the middle section 230 and dock sleeve 222 with the docking device 100 and retracting the dock sleeve 222 after the docking device 100 is deployed at the target implantation site.

In some examples, the proximal portion of the proximal section 228 can include a cut portion 229 which has a cross-section (in a plane normal to a central longitudinal axis of the sleeve shaft 220) that is not a complete circle (e.g., is open and does not form a closed tube). An end surface 225 can be formed between the cut portion 229 and the remainder of the proximal section 228. The end surface 225 can be configured normal to a central longitudinal axis of the sleeve shaft 220 and can be configured to come into contact with a stop element (e.g., plug 254) of the pusher shaft 212, as explained further below.

The cut portion 229 can extend into the hub assembly 218 of the handle assembly 202. As described below, a proximal extension 256 of the pusher shaft 212 can extend along an inner surface of the cut portion 229. The cut (e.g., open) profile of the cut portion 229 can allow the proximal extension 256 of the pusher shaft 212 to extend out of a void space 227 formed in the cut portion 229 and branch off, at an angle relative to the cut portion 229, into the suture lock assembly 216 of the hub assembly 218 (see e.g., FIG. 6). As such, the pusher shaft 212 and sleeve shaft 220 can be operated in parallel with one another and an overall length of the delivery apparatus 200 in which the sleeve shaft 220 and pusher shaft 212 are incorporated can be maintained similar to or only minimally longer than a delivery system that does not incorporate the sleeve shaft 220.

Additional examples of the sleeve shaft are described further in PCT Patent Application Publication No. WO/2020/247907.

Exemplary Pusher Shaft

Figure 7B:
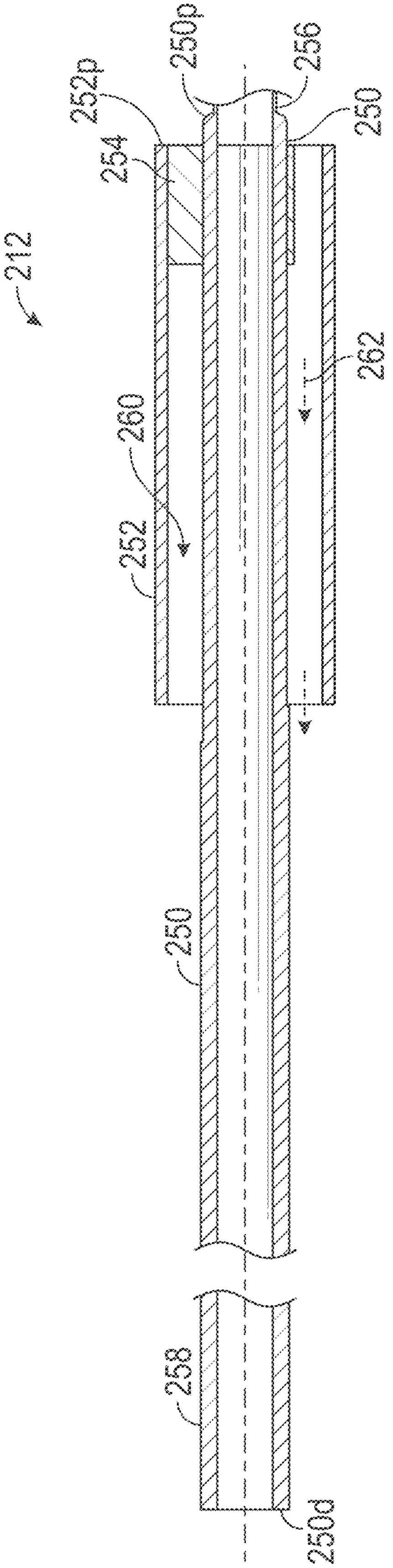
FIG. 7B is a side cross-sectional view of a pusher shaft, according to one example.

FIG. 7B shows a pusher shaft 212, according to one example. As shown, the pusher shaft 212 can include a main tube 250, a shell 252 surrounding a proximal end portion of the main tube 250, a plug 254 connecting the main tube 250 to the shell 252, and a proximal extension 256 extending from a proximal end of the main tube 250.

The main tube 250 can be configured for advancing and retracting a docking device (such as one of the docking devices described herein) and housing the release suture (e.g., 214) that secures the docking device to the pusher shaft 212. The main tube 250 can extend from the distal end 204*d* of the delivery sheath 204 into the handle assembly 202 of the delivery apparatus 200. For example, in certain examples, a proximal end portion of the pusher shaft 212, which includes an interface between the main tube 250, the shell 252, the plug 254, and the proximal extension 256, can be arranged within or proximate to the hub assembly 218 of the handle assembly 202. Thus, the main tube 250 can be an elongate tube that extends along a majority of the delivery apparatus 200.

The main tube 250 can be a relatively rigid tube that provides column strength for actuating deployment of a docking device. In some examples, the main tube 250 can be a hypo tube. In some examples, the main tube 250 can comprise a biocompatible metal, such as stainless steel. The main tube 250 can have a distal end 250*d* configured to interface with a docking device and a proximal end 250*p*, where the proximal extension 256 is attached. In some examples, a distal section 258 of the main tube 250 can be relatively more flexible (e.g., via one or more cuts into an outer surface of the main tube and/or having a durometer material) than the remaining part of the main tube 250. Thus, the distal section 258 can flex and/or bend along with the delivery sheath 204 of the delivery apparatus 200, as it is navigated through a vasculature of a patient, to the target implantation site.

In some examples, the shell 252 can be configured to lock the main tube 250 and provide a hemostatic seal on the pusher shaft 212 without interfering with movement of the sleeve shaft 220. As shown in FIG. 7B, an inner diameter of the shell 252 can be larger than an outer diameter of the main tube 250, thereby forming an annular cavity 260 between the main tube 250 and the shell 252. As such, the proximal section 228 of the sleeve shaft 220 can slide within the annular cavity 260, as described further below. Further, flush fluid provided to a lumen on an exterior of the proximal extension 256, in the hub assembly 218, can flow through the annular cavity 260 and exit at a distal end of the shell 252 (as shown by arrows 262) to enter a lumen between the sleeve shaft 220 and delivery sheath 204 of the delivery apparatus, as discussed further below with reference to FIG. 9.

The plug 254 can be configured to be arranged within the annular cavity 260, at a proximal end 252*p* of the shell 252. In some examples, the plug 254 can be configured to "plug" or fill a portion of the annular cavity 260 located at the proximal end 252*p* of the shell 252, while leaving the remaining portion of the annular cavity 260 open to receive the cut portion 229 of the sleeve shaft 220 therein. In some examples, the shell 252 and the plug 254 can be fixedly coupled to the main tube 250 (e.g., via welding) to allow the cut portion 229 of the sleeve shaft 220 to slide between the main tube 250 and the shell 252. As described below, the plug 254 can also act as a stop for the sleeve shaft 220.

As noted above, the proximal extension 256 can extend from the proximal end 250*p* of the main tube 250 and the shell 252. The proximal extension 256 can provide the pusher shaft 212 with certain flexibility such that it may be routed from the inside of the sleeve shaft 220 (e.g., the cut portion 229) to the outside of the sleeve shaft 220, thereby allowing the pusher shaft 212 and the sleeve shaft 220 to be actuated in parallel and reducing an overall length of the delivery apparatus. In certain examples, the proximal extension 256 can be made of a flexible polymer.

Additional examples of the pusher shaft are described further in PCT Patent Application No. PCT/US20/36577.

Exemplary Sleeve Shaft and Pusher Shaft Assembly

Figure 8A:
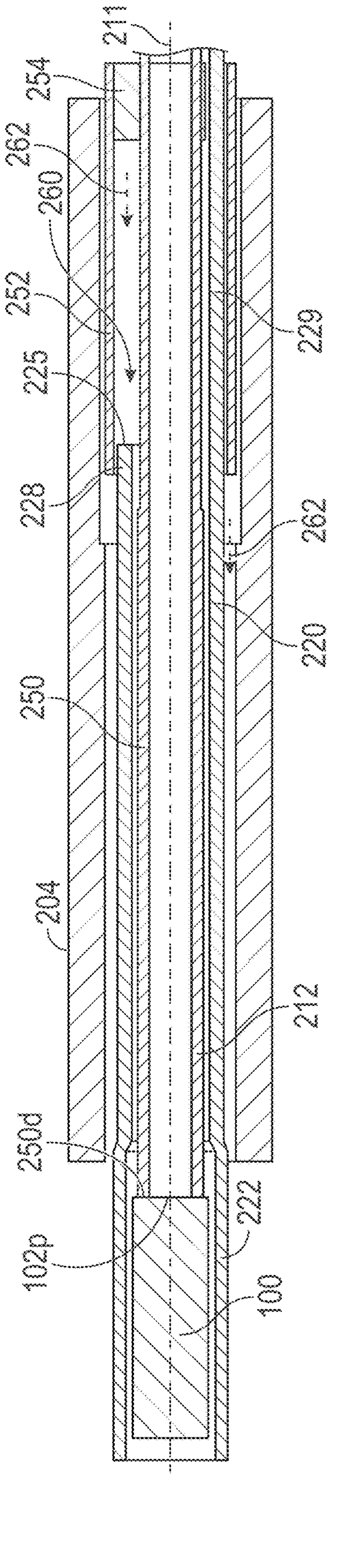
FIG. 8A is a side cross-sectional view of an assembly comprising the sleeve shaft of FIG. 7A, the pusher shaft of FIG. 7B, and a delivery sheath, wherein the sleeve shaft covers a docking device.
Figure 8B:
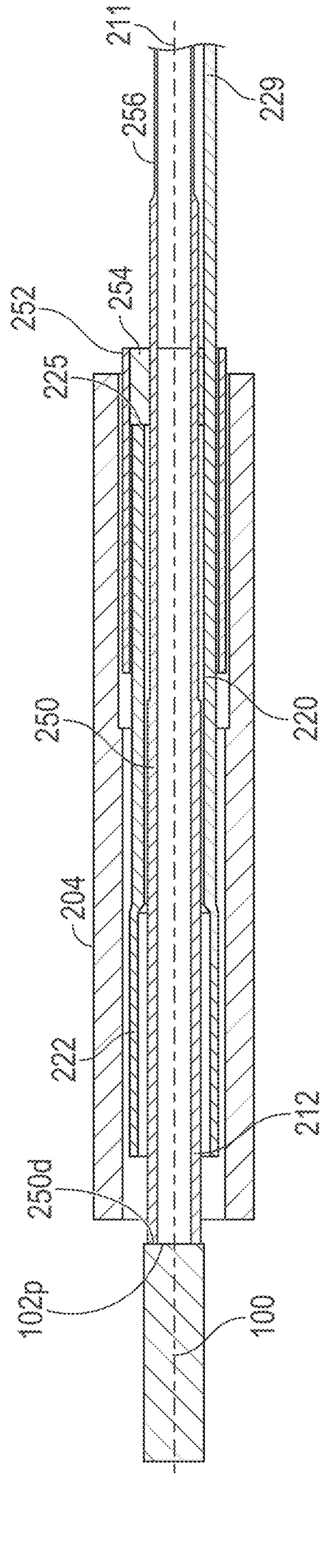
FIG. 8B is a side cross-sectional view of the same assembly of FIG. 8A, except the docking device is uncovered by the sleeve shaft.

FIGS. 8A-8B illustrate example arrangements of the pusher shaft 212 and sleeve shaft 220 in the delivery sheath 204 of the delivery apparatus 200, before and after deployment of a docking device such as 100. As shown, the main tube 250 of the pusher shaft 212 can extend through a lumen of the sleeve shaft 220, which can extend through a lumen of the delivery sheath 204. The pusher shaft 212 and the sleeve shaft 220 can share a central longitudinal axis 211 of the delivery sheath 204.

Figure 9:
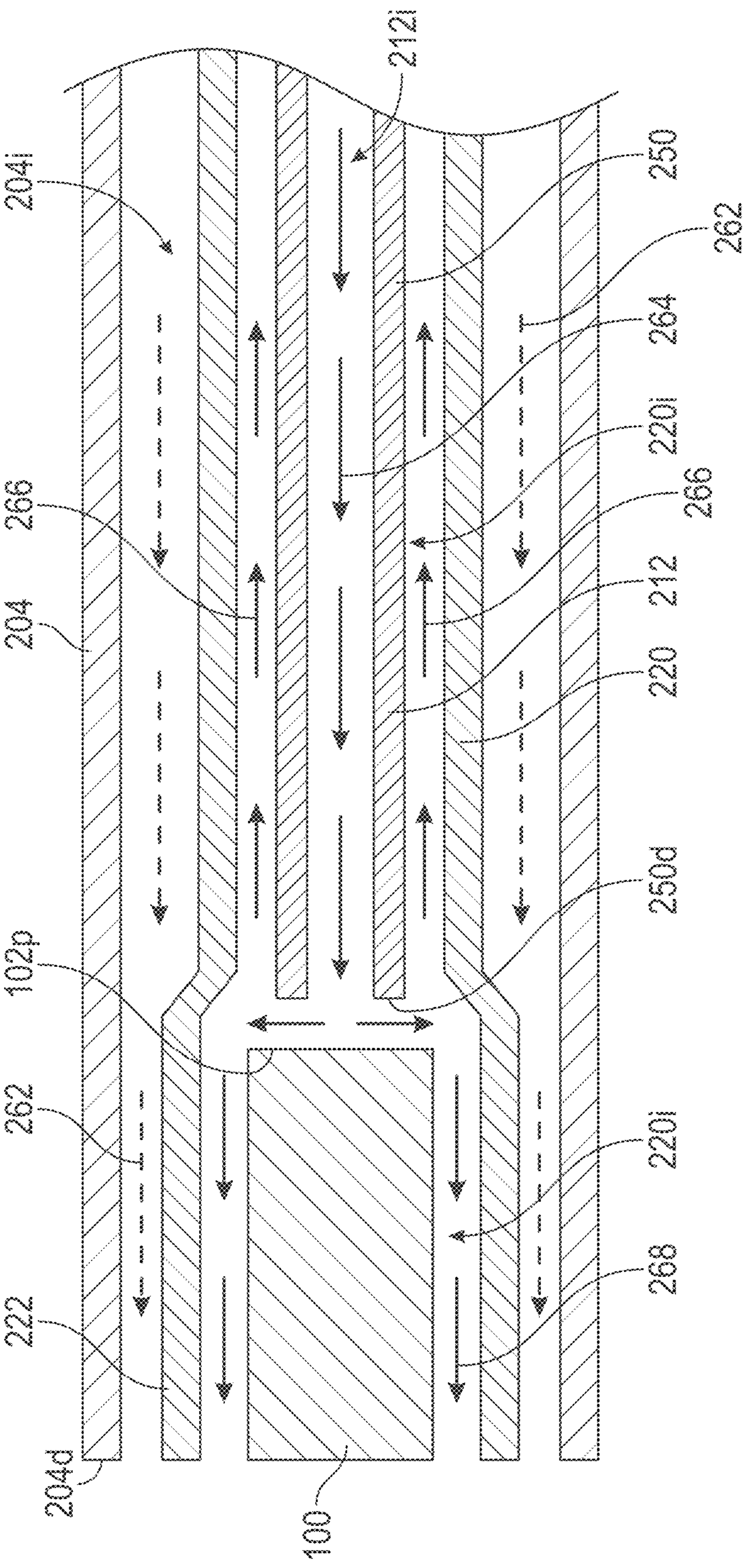
FIG. 9 is a schematic cross-sectional view of a distal end portion of a delivery system, showing fluid flow through lumens within the delivery system.
Figure 10A:
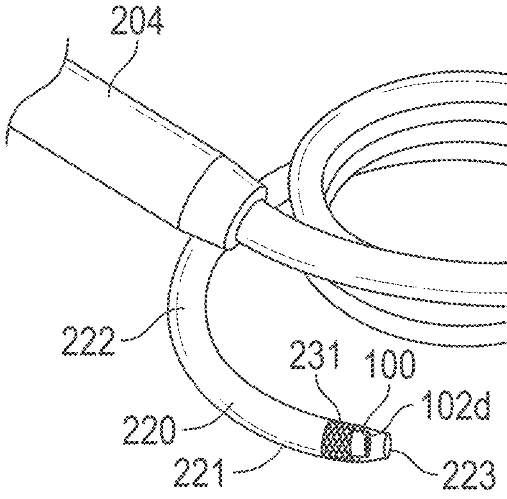
FIG. 10A illustrates a perspective view of an example of a sleeve shaft covering a docking device and extending outside of a delivery sheath of a delivery system.
Figure 10B:
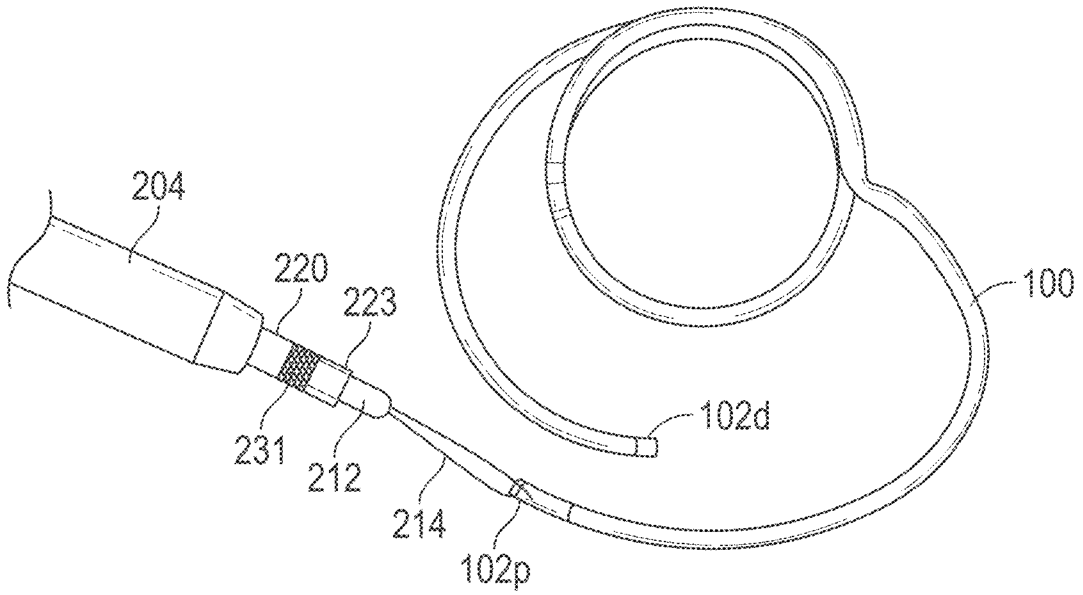
FIG. 10B illustrates the sleeve shaft surrounding a pusher shaft after deploying the docking device from the delivery system of FIG. 10A and removing the sleeve shaft from the docking device.

FIG. 9 shows various lumens configured to receive flush fluid during a delivery and implantation procedure can be formed between the docking device 100, the pusher shaft 212, the sleeve shaft 220, and the delivery sheath 204. Additionally, FIG. 10A shows a first configuration where the docking device 100 has been deployed from the delivery sheath 204 while still being covered by the dock sleeve 222 of the sleeve shaft 220. The dock sleeve 222 in the first configuration is also referred to be in a "covered state." When the dock sleeve 222 is in the covered state, the guard member 104 (not shown for clarity purposes) can remain in the delivery configuration (i.e., radially compressed by and retained within the dock sleeve 222). FIG. 10B shows a second configuration where the docking device 100 is uncovered by the dock sleeve 222 after the sleeve shaft 220 has been retracted back into the delivery sheath 204. The dock sleeve 222 in the second configuration is also referred to be in an "uncovered state." When the dock sleeve 222 is in the uncovered state, the guard member 104 (not shown for clarity purposes) can radially expand and move to the deployed configuration.

Specifically, FIG. 8A illustrates a first configuration of the pusher shaft 212 and sleeve shaft 220 assembly, pre-deployment or during deployment of the docking device 100, according to one example. As shown, the dock sleeve 222 can be configured to cover the docking device 100 while the end surface 225 of the sleeve shaft 220 is positioned away from the plug 254. In addition, the distal end 250*d* of the pusher shaft 212 can extend into the dock sleeve 222 and come into contact with the proximal end 102*p* of the docking device 100.

During deploying the docking device 100 from the delivery sheath 204, the pusher shaft 212 and the sleeve shaft 220 can be configured to move together, in the axial direction, with the docking device 100. For example, actuation of the pusher shaft 212, to push against the docking device 100 and move it out of the delivery sheath 204 can also cause the sleeve shaft 220 to move along with the pusher shaft 212 and the docking device 100. As such, the docking device 100 can remain being covered by the dock sleeve 222 of the sleeve shaft 220 during the procedure of pushing the docking device 100 into position at the target implantation site via the pusher shaft 212, as illustrated in FIG. 10A.

Additionally, as shown in FIG. 10A, during delivery and implantation of the covered docking device 100 at the target implantation site, the tip portion 223 of the sleeve shaft 220 can extend distal to the distal end 102*d* of the docking device 100, thereby providing the dock sleeve 222 with a more atraumatic tip.

In some examples, one or more radiopaque markers 231, can be placed at the dock sleeve 222 to increase the ability to visualize the dock sleeve 222 during deployment of a docking device (e.g., 100). In certain examples, at least one radiopaque marker 231 can be placed at the intersection between the body portion 221 and the tip portion 223. In certain examples, at least one radiopaque marker 231 can be placed on the tip portion 223. In some examples, the distal end 102*d* of the docking device 100 can be arranged proximate to or just distal to the radiopaque markers 231 of the dock sleeve 222.

In some examples, the radiopaque markers 231 can include a radiopaque material such as platinum-iridium. In other examples, the radiopaque material included in the radiopaque markers 231 can be Barium Sulphate (BaSO4), Bismuth Subcarbonate ($(BiO)_2CO_3$), Bismuth Oxychloride (BiOCl), or the like.

In some examples, the tip portion 223 of the dock sleeve 222 can be made from a polymeric material loaded with any one of the radiopaque material described above so as to enable the most distal edge of the tip portion 223 to be visible under fluoroscopy.

FIG. 8B illustrates a second configuration of the pusher shaft 212 and sleeve shaft 220 assembly, after deploying the docking device 100 from the delivery sheath 204 at the target implantation site and removing the dock sleeve 222 from the implanted docking device 100, according to one example. As shown, after implanting the docking device 100 at the target implantation site, in its desired position, the sleeve shaft 220 can be pulled off the docking device 100 and retracted back into delivery sheath 204 while holding the pusher shaft 212 steady so that its distal end 250*d* presses against the proximal end 102*p* of the docking device 100. Alternatively, the docking device 100 can be exposed by pushing the pusher shaft 212 in the distal direction while holding the sleeve shaft 220 steady. In some examples, as shown in FIG. 8B, the sleeve shaft 220 can be stopped from further retraction into the delivery apparatus upon the end surface 225 coming into contact with the plug 254.

FIG. 10B shows the sleeve shaft 220 removed from the docking device 100, leaving the docking device 100 uncovered by the dock sleeve 222. As shown, the tip portion 223 of the sleeve shaft 220 can be arranged proximal to (e.g., retracted past) the distal end of the pusher shaft 212 which can still be connected to the proximal end 102*p* of the docking device 100 via the release suture 214. As explained further below, after implanting the docking device 100 at the target implantation site and removing the dock sleeve 222 from covering the docking device 100, the docking device 100 can be disconnected from the delivery apparatus by cutting the release suture 214, e.g., by using the suture lock assembly 216 of the delivery apparatus 200.

As shown in FIG. 9, a first, pusher shaft lumen 212*i* can be formed within an interior of the pusher shaft 212 (e.g., within an interior of the main tube 250). The pusher shaft lumen 212*i* can receive a flush fluid from a first fluid source, which may be fluidly coupled to a portion of the handle assembly 202. The flush fluid flow 264 through the pusher shaft lumen 212*i* can travel along a length of the main tube 250 of the pusher shaft 212, to the distal end 250*d* of the main tube 250 of the pusher shaft 212. In some examples, the distal end 250*d* of the main tube 250 can be spaced away from the proximal end 102*p* of the docking device 100. Thus, at least a portion of the flush fluid flow 264 can flow into a distal portion of a second, sleeve shaft lumen 220*i*, which is arranged between an outer surface of the docking device 100 and an inner surface of the dock sleeve 222 of the sleeve shaft 220, as flush fluid flow 268. Further, in some examples, a portion of the flush fluid flow 264 can also flow back into a proximal portion of the sleeve shaft lumen 220*i*, which is arranged between an outer surface of the pusher shaft 212 and an inner surface of the sleeve shaft 220 that is proximal to the dock sleeve 222, as flush fluid flow 266. Thus, the same, first fluid source may provide flush fluid to the pusher shaft lumen 212*i* the sleeve shaft lumen 220*i* (including both the distal portion outside the dock sleeve 222 and the proximal portion that is proximal to the dock sleeve 222), via the pusher shaft lumen 212*i*.

FIG. 9 also shows a third, delivery sheath lumen 204*i*, which is arranged between an inner surface of the delivery sheath 204 and an outer surface of the sleeve shaft 220. The delivery sheath lumen 204*i* can receive a flush fluid from one or more second fluid sources, which may be fluidly coupled to a portion of the handle assembly 202, and which may result in flush fluid flow (as shown by arrows 262) flowing through the delivery sheath lumen 204*i*, to the distal end 204*d* of the delivery sheath 204.

Flushing the above-described lumens can help prevent or reduce thrombosis on and around the docking device 100 and other concentric parts of the delivery apparatus 200 during deployment of the docking device 100 from the delivery apparatus 200 and implantation of the docking device 100 at a target implantation site. In an example, as shown in FIG. 6, the first and/or the second fluid sources can be connected to one or more flushing ports (e.g., 232, 236, 238) arranged on and/or coupled to the handle assembly 202 of the delivery apparatus 200 to provide the flush fluid to the lumens described above.

Additional examples of the sleeve shaft and pusher shaft assembly are described further in PCT Patent Application No. PCT/US20/36577.

Exemplary Implantation Procedure

An example method of delivering a docking device (such as the docking device 100 described above) and implanting a prosthetic valve (such as the prosthetic valve 10 described above) within the docking device is illustrated in FIGS.

11-24. In this example, the target implantation site is at the native mitral valve 422. Following the same principle described herein, the same method or its variants can also be used for implantation of the docking device and the prosthetic valve at other target implantation sites.

Figure 11:
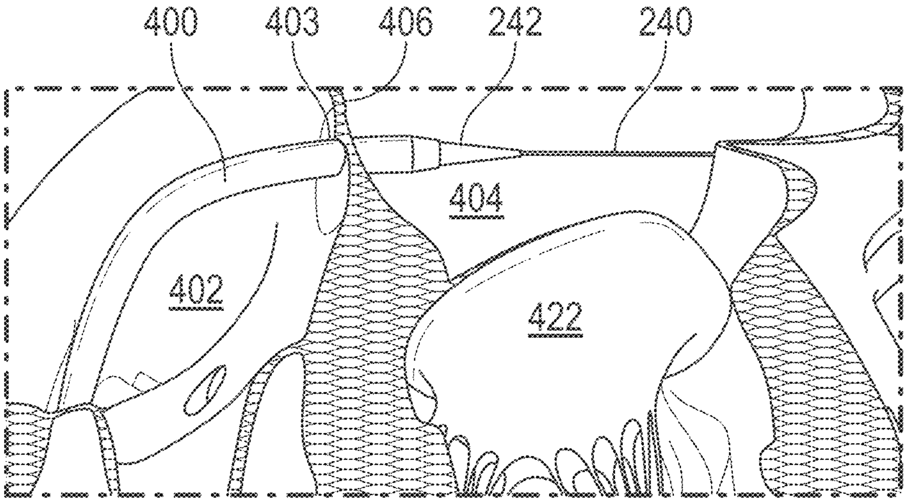
FIGS. 11-24 depict various portions of an exemplary implantation procedure in which the delivery apparatus of FIG. 6 is being used to implant the prosthetic implant assembly of FIG. 3A at a native mitral valve location using a transseptal delivery approach.

FIG. 11 illustrates introducing a guiding catheter 400 into a patient's heart over a previously inserted guidewire 240. Specifically, the guiding catheter 400 and the guidewire 240 are inserted from the right atrium 402 into the left atrium 404 through the interatrial septum 406 (e.g., via a previously punctured hole 403 in the interatrial septum 406). To facilitate navigation through the patient's vasculature and transseptal insertion, a nosecone 242 having a tapered distal tip can be placed at a distal end of the guiding catheter 400. After the distal end of the guiding catheter 400 enters the left atrium 404, the nosecone 242 and the guidewire 240 can be retracted back into the guiding catheter 400, for example, by operating a handle connected to a proximal end of the guiding catheter 400. The guiding catheter 400 can remain in place (i.e., extending through the interatrial septum 406) so that the distal end of the guiding catheter 400 remains within the left atrium 404.

FIG. 12 illustrates introducing a delivery apparatus (such as the delivery apparatus 200 described above) through the guiding catheter 400. Specifically, the delivery sheath 204 can be inserted through a lumen of the guiding catheter 400 until the distal end portion 205 of the delivery sheath 204 extends distally out of the distal end of the guiding catheter 400 and into the left atrium 404.

Figure 13:
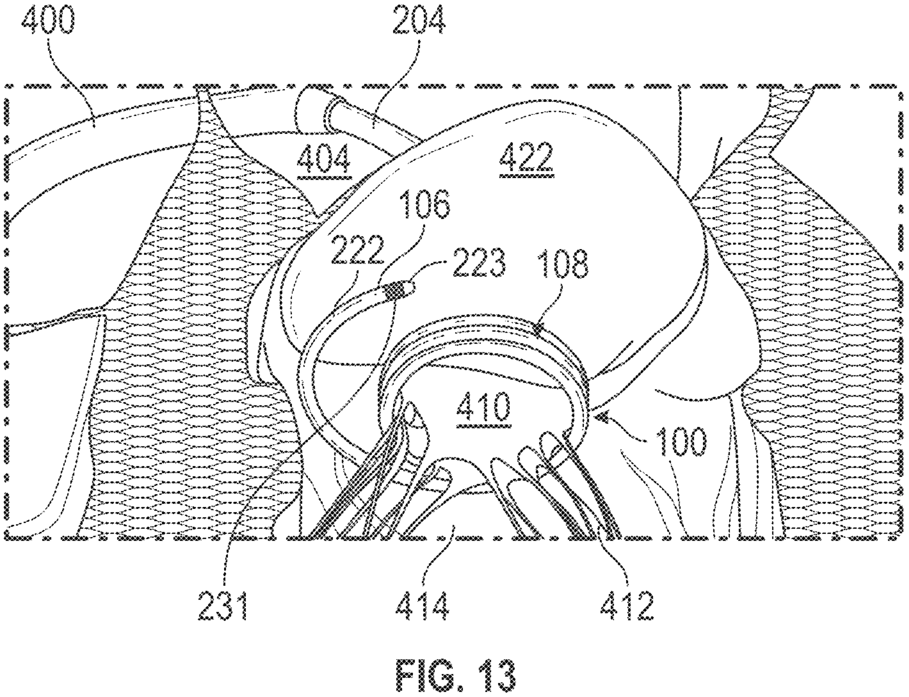
Figure 14:
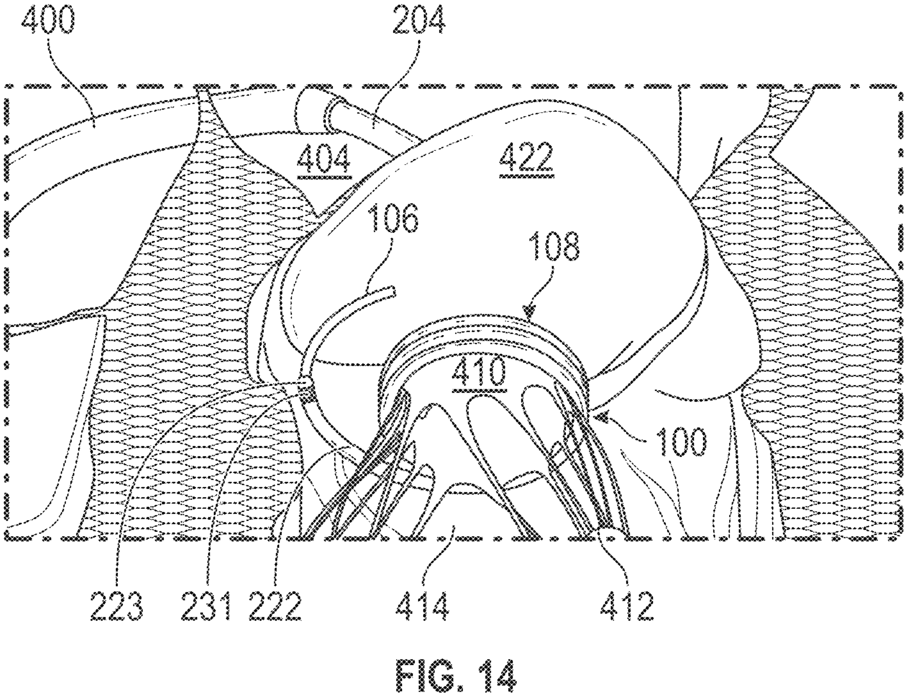

As described above, the delivery apparatus 200 can have a sleeve shaft 220 and a pusher shaft 212, both of which can extend through a lumen of the delivery sheath 204. As shown in FIGS. 13-14, the distal end portion of the sleeve shaft 220 can have a dock sleeve 222 which surrounds the docking device 100. As described herein, the dock sleeve 222 can be retained within the distal end portion 205 of the delivery sheath 204.

As described above, the distal end portion 205 of the delivery sheath 204 can be steerable, for example, by operating a knob located on the handle assembly 202. Because the dock sleeve 222 and the docking device 100 are also flexible, flexing of the distal end portion 205 of the delivery sheath 204 can also cause flexing of the dock sleeve 222 and the docking device 100 retained therein. As shown in FIG. 12, the distal end portion 205 of the delivery sheath 204 (along with the dock sleeve 222 retaining the docking device 100) can be flexed in desired angular directions so that the distal end 204*d* of the delivery sheath 204 can extend through the native mitral valve annulus 408 at a location adjacent the posteromedial commissure 420 and into the left ventricle 414.

FIG. 13 illustrates deployment of the docking device 100 at the mitral valve location. As shown, a distal portion of the docking device 100, which includes the leading turn 106 and the central region 108 of the coil, can be deployed out of the distal end 204*d* of the delivery sheath 204 and extend into the left ventricle 414. Note that the deployed distal portion of the docking device 100 is still covered by the dock sleeve 222. This can be achieved, for example, by retracting the delivery sheath 204 in the proximal direction while holding both the pusher shaft 212 and the sleeve shaft 220 in place, thus causing the distal portion of the docking device 100 to extend distally out of the delivery sheath 204 while it remains to be covered by the dock sleeve 222. Retraction of the delivery sheath 204 can continue until the delivery sheath 204 is moved to the stabilization turn 110 and proximal to the expandable member 104.

Not being restrained by the distal end portion 205 of the delivery sheath 204, the distal portion of the docking device 100 can move from the delivery configuration to the deployed (i.e., helical) configuration. Specifically, as shown in FIG. 13, the coil of the docking device 100 (covered by the dock sleeve 222) can form the leading turn 106 extending into the left ventricle 414, as well as a plurality of functional turns in the central region 108 that wrap around the native leaflets 410 of the native valve and the chordae tendineae 412.

Because the dock sleeve 222 has a lubricious surface, it can prevent or reduce the likelihood of the tubular member 112 (which surrounds the coil 102 of the docking device) from directly contacting and catching (or getting stuck with) the native tissue and help ensure that the covered docking device 100 encircles the native anatomy. In addition, the soft tip portion 223 (which can have a tapered shape) of the dock sleeve 222 can also facilitate atraumatic encircling around the native tissue. As noted above, a flush fluid (sec e.g., 264 in FIG. 9) can flow through the dock sleeve 222 and around the docking device 100 to prevent or reduce thrombosis on and around the docking device 100 and other concentric parts of the delivery apparatus 200 during deployment of the docking device 100.

Figure 15:
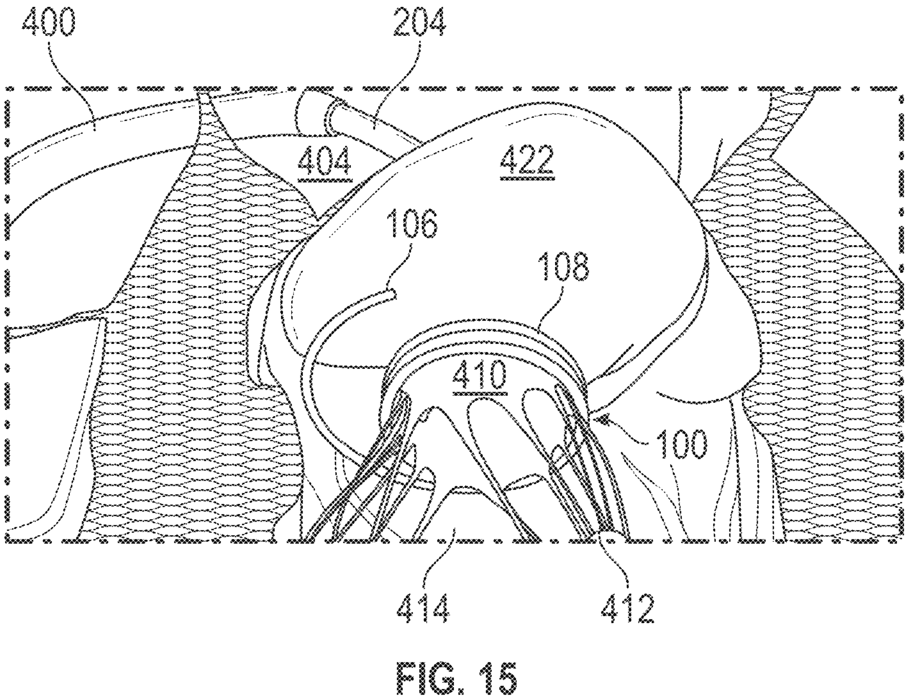

As shown in FIG. 14, after the functional turns of the docking device 100 successfully wraps round the native leaflets 410 and the chordae tendineae 412, the dock sleeve 222 can be retracted in a proximal direction relative to the docking device 100. This can be achieved, for example, by pulling the sleeve shaft 220 in the proximal direction while holding the pusher shaft 212 steady so that its distal end can press against the proximal end of the docking device 100, as described above with reference to FIG. 8B. As noted above, the dock sleeve 222 can be retracted back into the delivery sheath 204. FIG. 15 shows the docking device 100, which is uncovered by the dock sleeve 222, encircling the native leaflets and chordae tendineae.

Figure 16A:
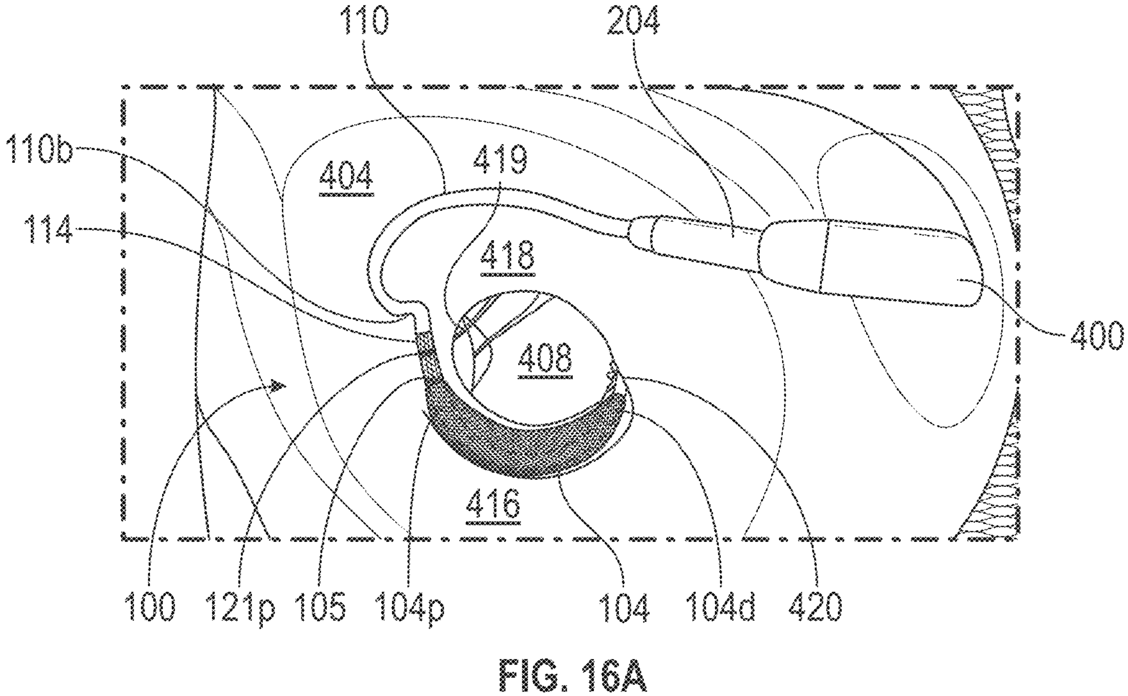

FIG. 16A illustrates stabilizing the docking device 100 from the atrial side. As shown, the delivery sheath 204 can be retracted into the guiding catheter 400 so that the atrial side (i.e., the proximal portion) of the docking device 100, including the stabilization turn 110 of the coil can be exposed. The stabilization turn 110 can be configured to provide one or more points or regions of contact between the docking device 100 and the left atrial wall, such as at least three points of contact in the left atrium or complete contact on the left atrial wall. The stabilization turn 110 can be flared out or biased toward both the posterior wall 416 and the anterior wall 418 of the left atrium so as to prevent the docking device 100 from falling into the left ventricle prior to deployment of a prosthetic valve therein.

Without the constraint of the delivery sheath 204 and the dock sleeve 222, the guard member 104 can move to the deployed configuration (due to radial expansion of the expandable member 116). As shown, the guard member 104 of the docking device 100 can be configured to contact the native annulus in the left atrium to create a sealed and atraumatic interface between the docking device 100 and the native tissue. The proximal end portion 104*p* of the guard member can be configured to be positioned adjacent (but does not reach) the anterolateral commissure 419 of the native valve. In the deployed configuration, the proximal end 105 of the guard member can be configured to be positioned within the atrial portion 110*a* or the ascending portion 110*b* of the stabilization turn, but distal to the boundary 107 between the ascending portion 110*b* and the stabilization portion 110*c* (see, e.g., FIG. 1A). For example, after the initial deployment of the docking device 100 and before deploying the prosthetic valve (e.g., 10) within the docking device 100, the proximal end 105 of the guard member can be configured to be positioned between the proximal seating marker 121*p* and the distal seating marker 121*d*, or slightly distal to the distal seating marker 121*d* in certain circumstances. In certain examples, the distal end portion 104*d* of the guard member can be disposed in the left ventricle 414 or at least adjacent a posteromedial commissure 420 of the native valve so that leakage at that location can be prevented or reduced.

In the depicted example, a proximal end portion of the retention element 114 extends into the ascending portion 110*b* of the coil. In addition, the proximal end 105 of the guard member 104 is located distal to the proximal seating marker 121*p*, which is located distal to the ascending portion 110*b*. In certain examples, the proximal end 105 of the guard member 104 is located between the proximal seating marker 121*p* and the distal seating marker 121*d* (which is covered by the guard member 104 and not shown in FIG. 16A). As described above, such configuration can advantageously improve the sealing and/or durability of the guard member 104.

Figure 16B:
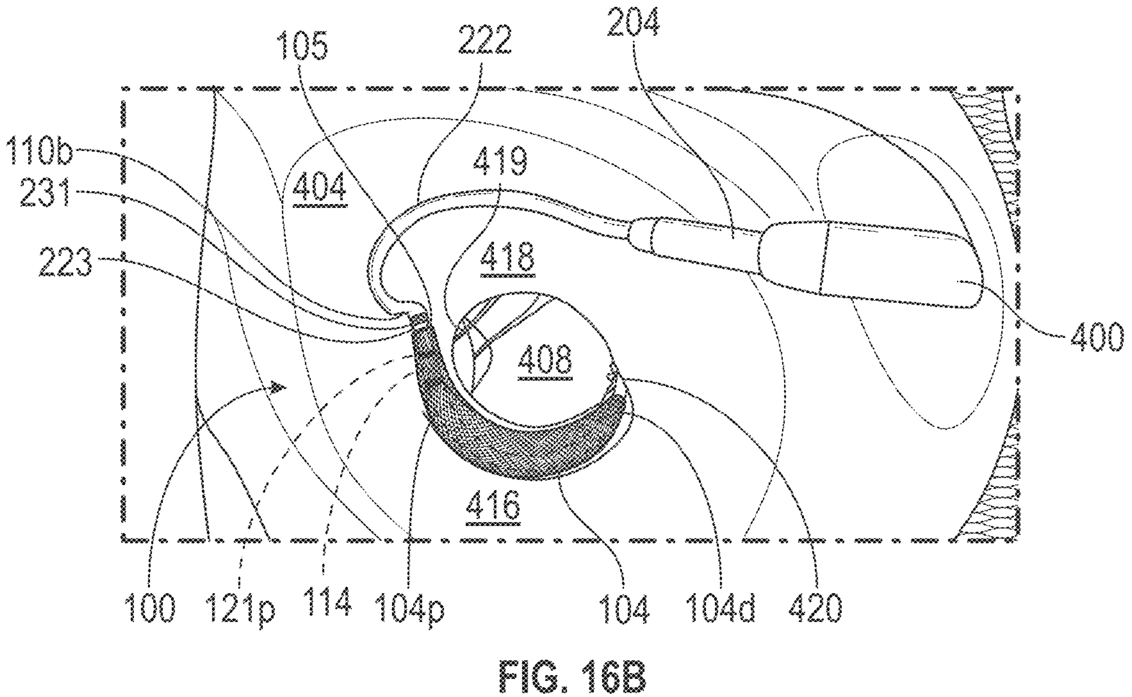
Figure 16C:
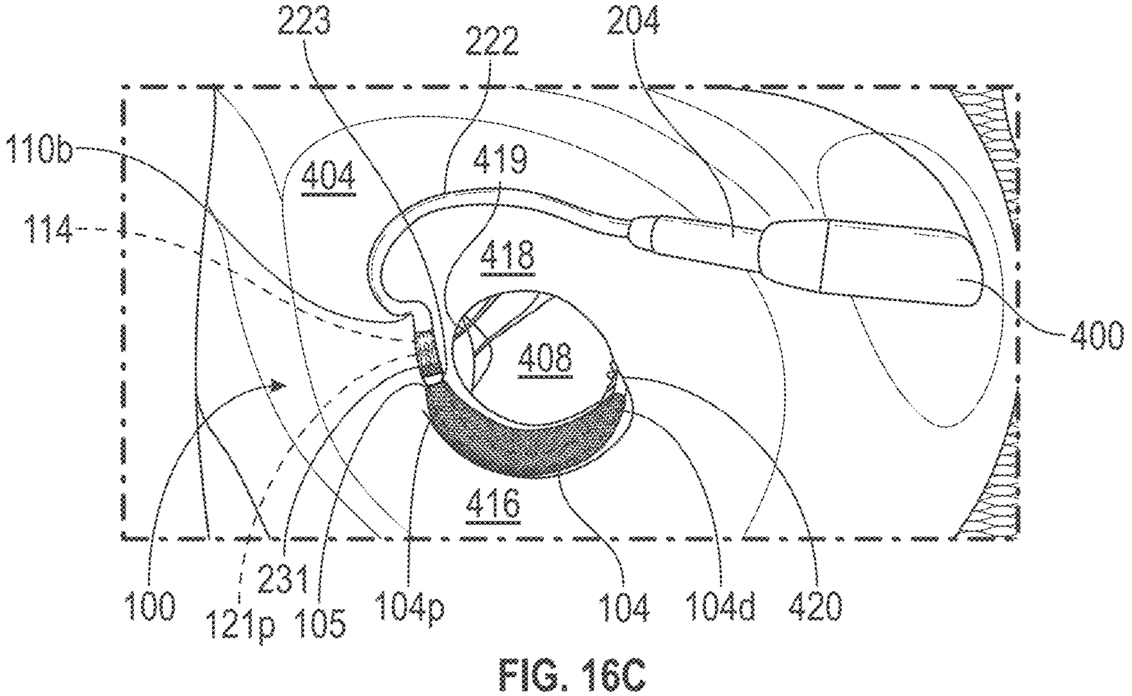

In certain instances, after initial deployment of docking device 100, the proximal end 105 of the guard member 104 may incidentally extend onto the ascending portion 110*b*, as illustrated in FIG. 16B. Under such circumstances, the dock sleeve 222 can be used to "reposition" the proximal end 105 of guard member 104 away from the ascending portion 110*b*. According to one example, the dock sleeve 222 can be pushed out of the delivery sheath 204 until its tapered tip portion 223 contacts the tapered proximal end 105 of the guard member 104 (see, e.g., FIG. 16B). Location of the tip portion 223 of the dock sleeve 222 can be determined, e.g., based on visualization of the radiopaque marker 231 on the dock sleeve 222 under fluoroscopy. Thus, by further pushing the dock sleeve 222 in the distal direction, the proximal end 105 of the guard member 104 can be moved distally until it is repositioned distal to the proximal seating marker 121*p* (see e.g., FIG. 16C). Such positioning can be confirmed, e.g., by observing the radiopaque marker 231 on the dock sleeve 222 is located distal to the proximal seating marker 121*p*. The dock sleeve 222 can then be retracted back into the delivery sheath 204. As described above, the retention element 114, by applying a friction force (e.g., the frictional interaction between the retention element 114 and the proximal end 105 of the guard member 104), can impede the axial movement of the proximal end portion 104*p* of the guard member 104 relative to the coil. Thus, the retention element 114 can retain the proximal end 105 of the guard member 104 in the repositioned location, which is distal to the ascending portion 110*b*.

Figure 17:
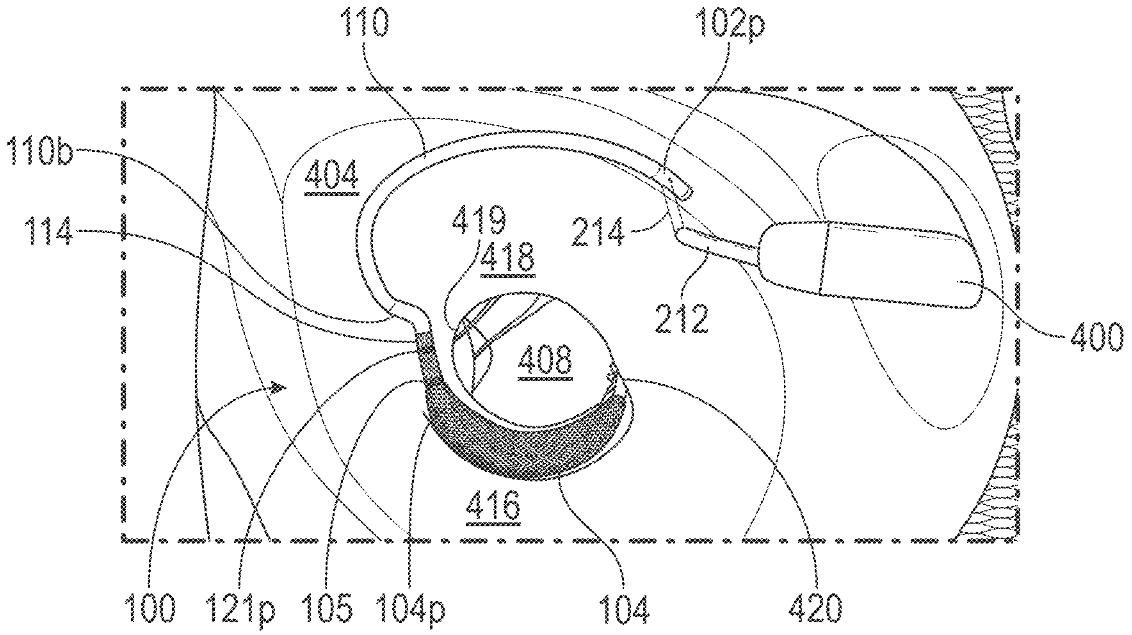

FIG. 17 illustrates the fully deployed docking device 100. The release suture 214, which extends through the pusher shaft 212 and connects the proximal end 102*p* of the coil to the suture lock assembly 216, can then be cut so that the docking device 100 can be released from the delivery apparatus 200. The delivery apparatus 200 can then be removed from the guiding catheter 400 to prepare for implantation of a prosthetic valve.

Figure 18:
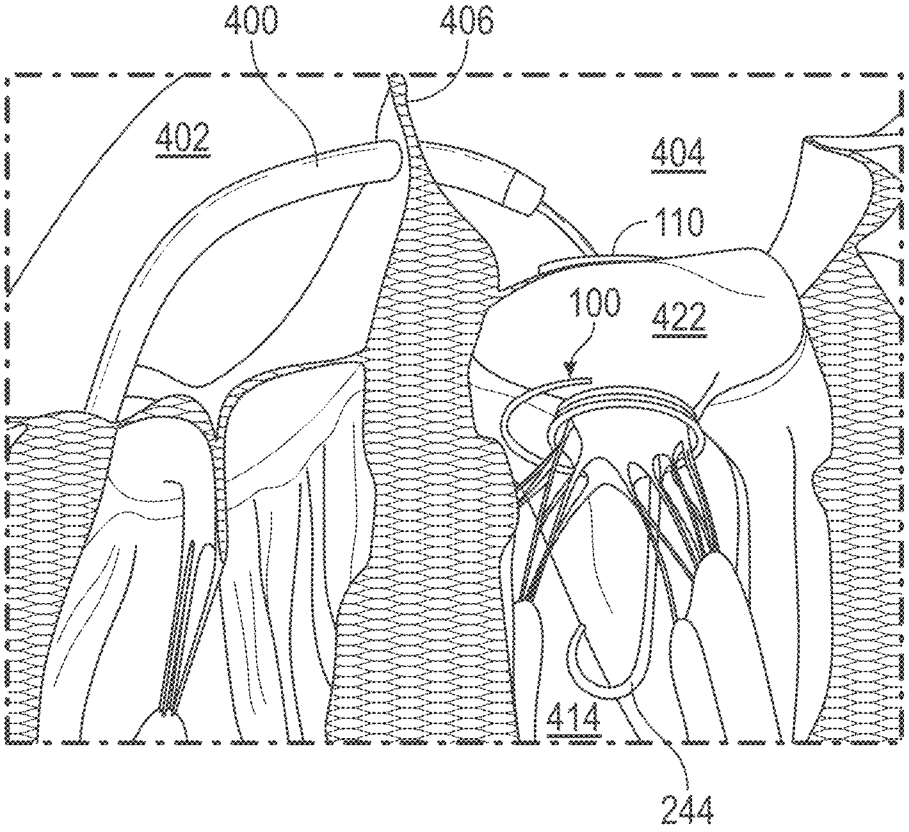

FIG. 18 illustrates inserting a guidewire catheter 244 through the guiding catheter 400, across the native mitral valve annulus through the docking device 100, and into the left ventricle 414.

Figure 19:
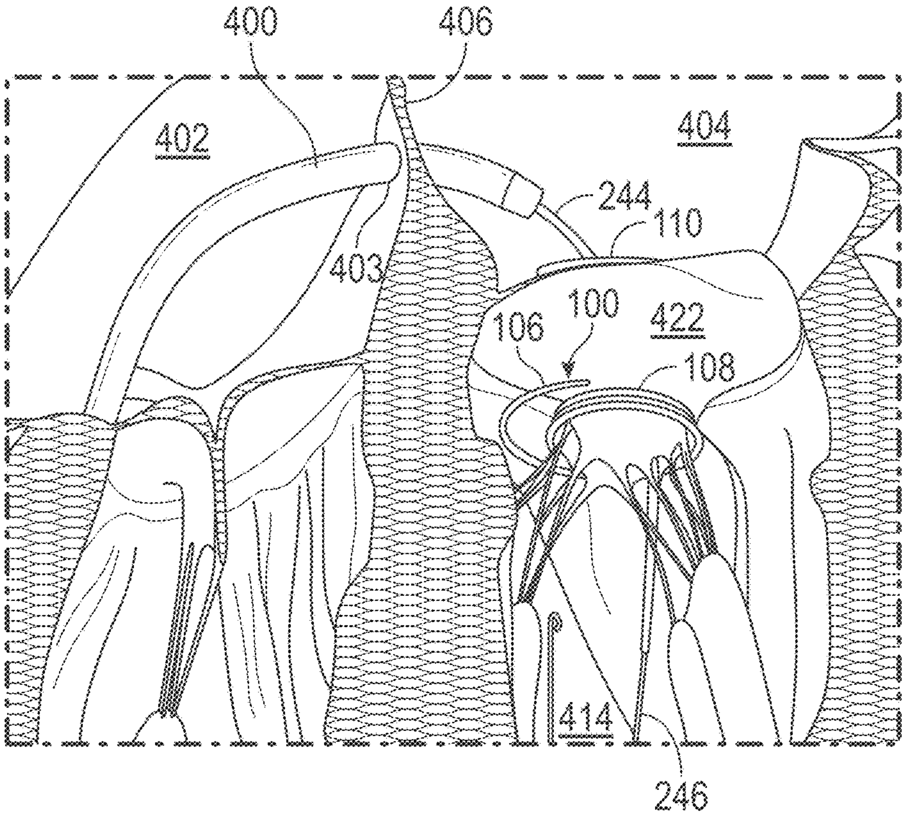

FIG. 19 illustrates inserting a valve guidewire 246 into the left ventricle 414 through an inner lumen of the guidewire catheter 244. The guidewire catheter 244 can then be retracted back into the guiding catheter 400, and the guiding catheter 400 and the guidewire catheter 244 can be removed, leaving the valve guidewire 246 in place.

Figure 20:
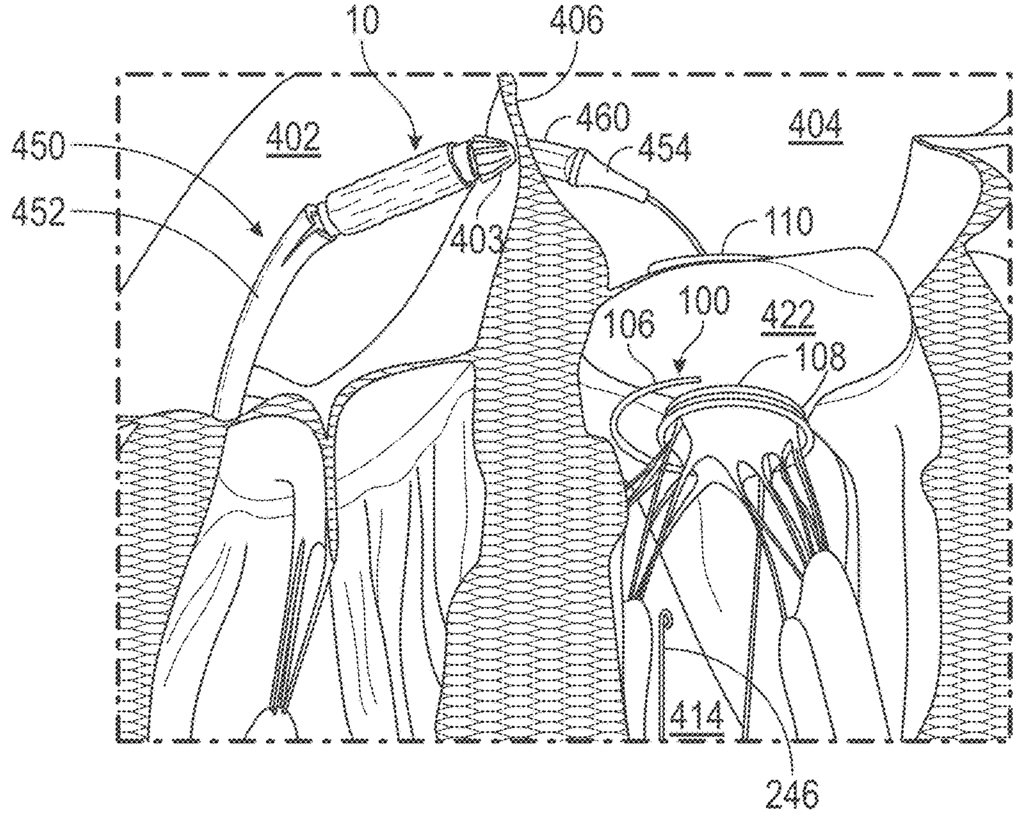

FIG. 20 illustrates transseptal delivery of a prosthetic valve (such as the prosthetic valve 10) into the left atrium 404. A prosthetic valve delivery apparatus 450 can be introduced over the valve guidewire 246. During delivery, the prosthetic valve 10 can be crimped over a deflated balloon 460 located between a distal end of an outer shaft 452 and a nosecone 454 of the delivery apparatus 450. In some examples, before transseptal delivery of the prosthetic valve 10, the hole 403 on the interatrial septum 406 can be further dilated by inserting a balloon catheter through the hole 403 and radially expanding a balloon mounted on the balloon shaft.

Figure 21:
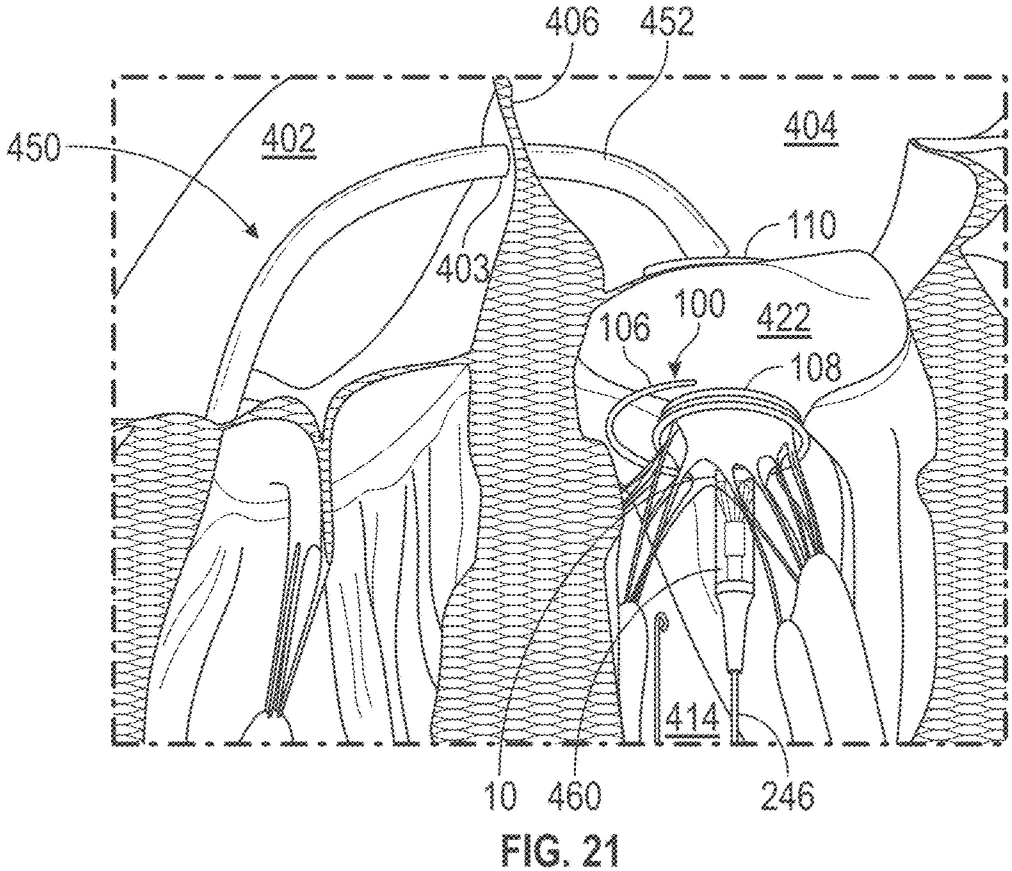
Figure 22:
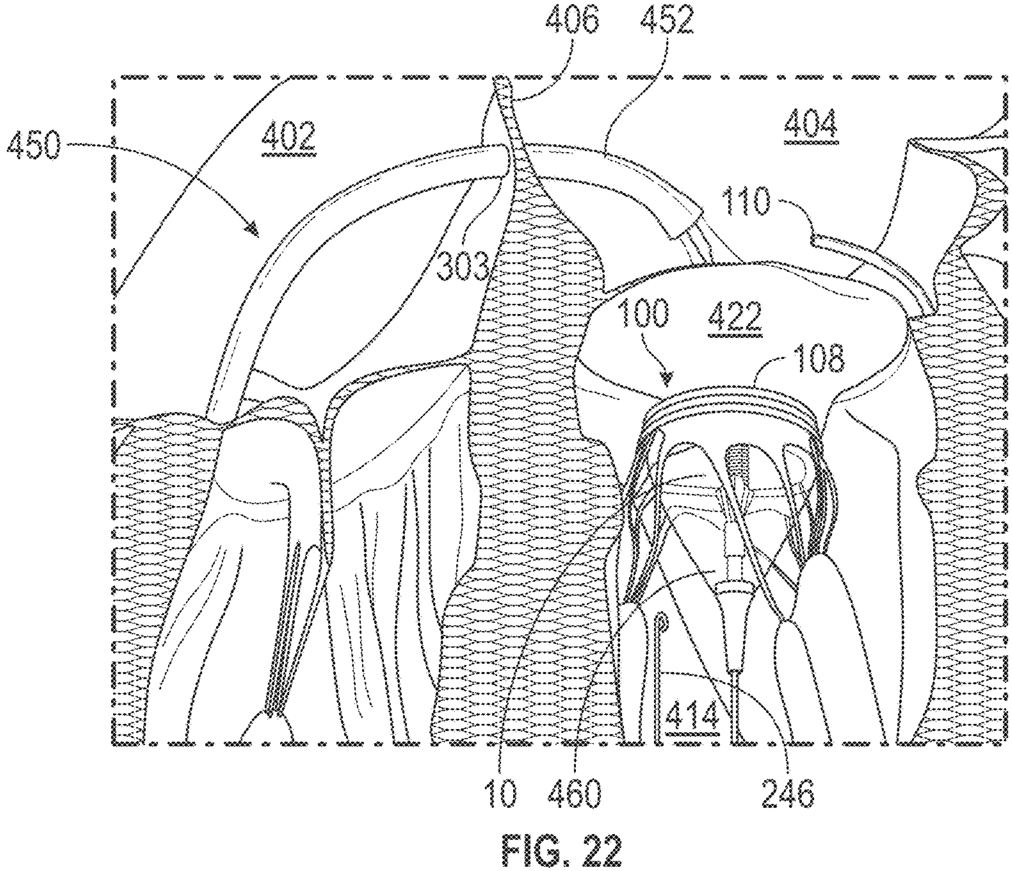

FIG. 21 illustrates placing the prosthetic valve 10 within the docking device 100. Specifically, the prosthetic valve 10 can be positioned within and substantially coaxial with the functional turns in the central region 108 of the docking device 100. In some examples, the outer shaft 452 can be slightly retracted so that the balloon 460 is located outside the outer shaft 452. FIG. 22 illustrates radial expansion of the prosthetic valve 10 within the docking device 100. Specifically, the balloon 460 can be radially inflated by injecting an inflation fluid into the balloon through the delivery apparatus 450, thereby causing radial expansion of the prosthetic valve 10. As the prosthetic valve 10 is radially expanded within the central region 108 of the coil, the functional turns in the central region 108 can be further radially expanded (i.e., the coil 102 of the docking device can move from the first radially expanded configuration to the second radially expanded configuration, as described above). To compensate for the increased diameter of the function turns, the leading turn 106 can be retracted in the proximal direction and become a part of the functional turn in the central region 108.

Figure 23:
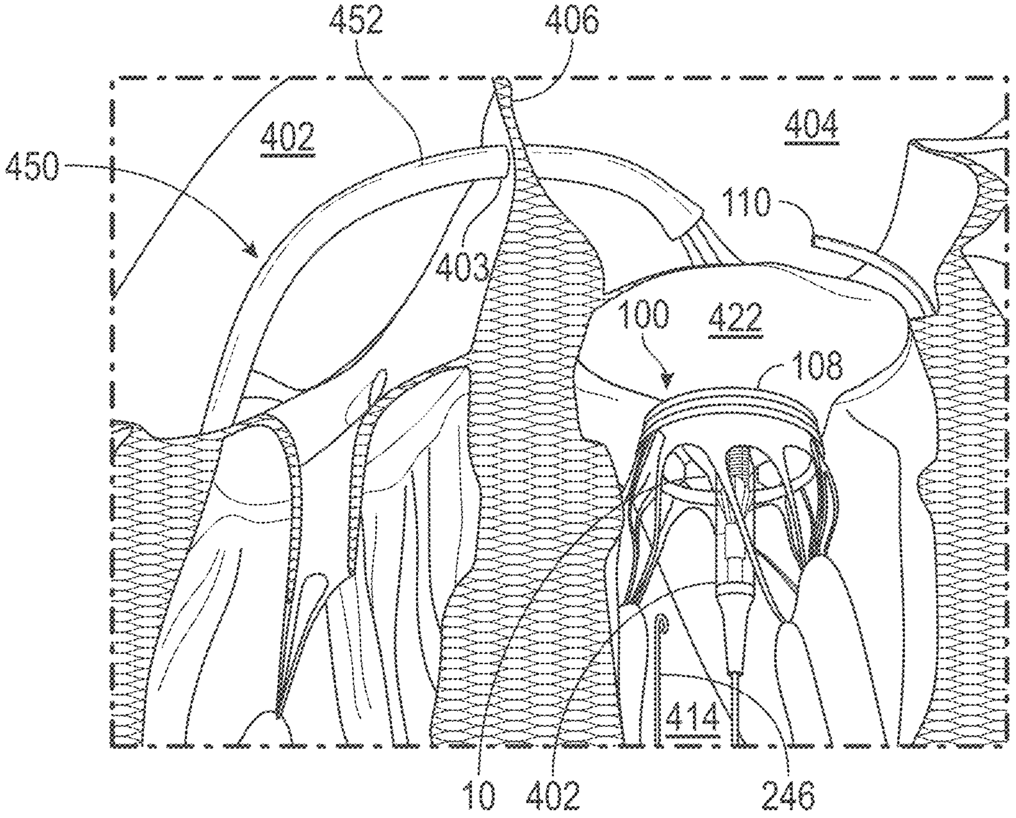

FIG. 23 illustrates deflating the balloon 460 after radial expansion of the prosthetic valve 10 within the docking device 100. The balloon 460 can be deflated by withdrawing the inflation fluid out of the balloon through the delivery apparatus 450. The delivery apparatus 450 can then be retracted out of the patient's vasculature, and the valve guidewire 246 can also be removed.

FIG. 24 illustrates the final disposition of the docking device 100 at the mitral valve and the prosthetic valve 10 received within the docking device 100. As described above, the radial tension between the prosthetic valve 10 and the central region 108 of the docking device can securely hold the prosthetic valve 10 in place. In addition, the guard member 104 can act as a seal between the docking device 100 and the prosthetic valve 10 disposed therein to prevent or reduce paravalvular leakage around the prosthetic valve 10.

As described above, radially expanding the prosthetic valve 10 within the docking device 100 can cause the guard member 104 to be radially compressed and axially extended, and as a result, the proximal end 105 of the guard member 104 can have a tendency to move proximally relative to the coil. However, the presence of the retention element 114 can frictionally impede the proximal end 105 of the guard member 104 to move proximally over the coil. In addition, the proximal seating marker 121*p* (which sets the proximal boundary of the proximal end 105 of the guard member 104 after initial deployment of the docking device 100) can be configured to be located far enough from the ascending portion 110*b* of the coil. Thus, even if the proximal end 105 of the guard member 104 indeed moves proximally due to radial expansion of the prosthetic valve 10 within the docking device 100, such movement can be limited to the extent that the proximal end 105 of the guard member 104 does not extend into the ascending portion 110*b* of the coil 102.

As the prosthetic heart valve 10 is fully expanded within the docking device 100, the prosthetic heart valve 10 contacts the guard member 104 and urges the guard member 104 against the coil 102, thereby restricting further axial movement of the guard member 104 relative to the native anatomy (e.g., the left atrial wall). In this manner, the retention member 114 can serve to temporarily retain the proximal end of the guard member in the desired position from the time the docking device is deployed until the prosthetic heart valve is expanded therein. After that, the prosthetic heart valve can secure the positioning of the guard member relative to the coil.

Although in the method described above, the prosthetic valve 10 is radially expanded using the inflatable balloon 460, it is to be understood that alternative methods can be used to radially expand the prosthetic valve 10.

For example, in some instances, the prosthetic valve can be configured to be self-expandable. During delivery, the prosthetic valve can be radially compressed and retained within a valve sheath located at a distal end portion of a delivery apparatus. When the valve sheath is disposed within the central region 108 of the docking device, the valve sheath can be retracted to expose the prosthetic valve, which can then self-expand and securely engage with the central region 108 of the docking device. Additional details regarding exemplary self-expandable prosthetic valves and the related delivery apparatus/catheters/systems are described in U.S. Pat. Nos. 8,652,202 and 9,155,619, the entirety of which is incorporated by reference herein.

In another example, in certain instances, the prosthetic valve can be mechanically expanded. Specifically, the prosthetic valve can have a frame comprising a plurality of struts that are connected to each other such that an axial force applied to the frame (e.g., pressing an inflow and an outflow end of the frame in toward each other or pulling the inflow end and the outflow end of the frame away from each other) can cause the prosthetic valve to radially expand or compress. Additional details regarding exemplary mechanically-expandable prosthetic valves and the related delivery apparatus/catheters/systems are described in U.S. Patent Application Publication No. 2018/0153689 and PCT Patent Application Publication No. WO/2021/188476, the entirety of which are incorporated by reference herein.

The treatment techniques, methods, steps, etc. described or suggested herein or in references incorporated herein can be performed on a living animal or on a non-living simulation, such as on a cadaver, cadaver heart, anthropomorphic ghost, simulator (e.g., with the body parts, tissue, etc. being simulated), etc.

Exemplary Foldable PVL Guard

Figure 25A:
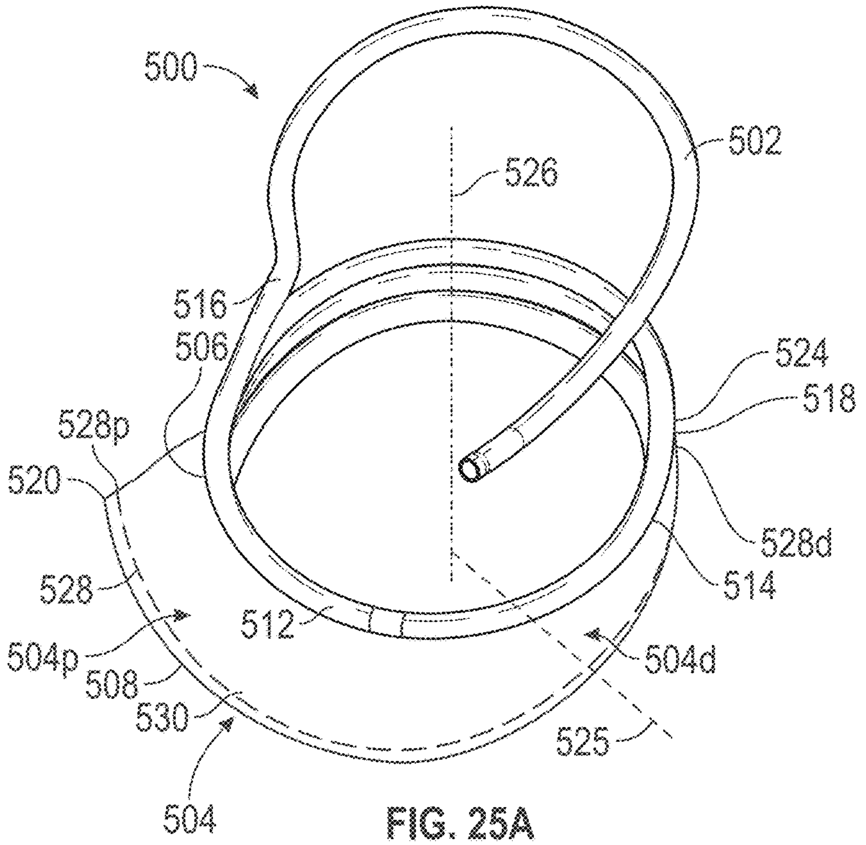
FIG. 25A is a top perspective view of another docking device having a foldable PVL guard in a deployed configuration, according to one example.
Figure 25B:
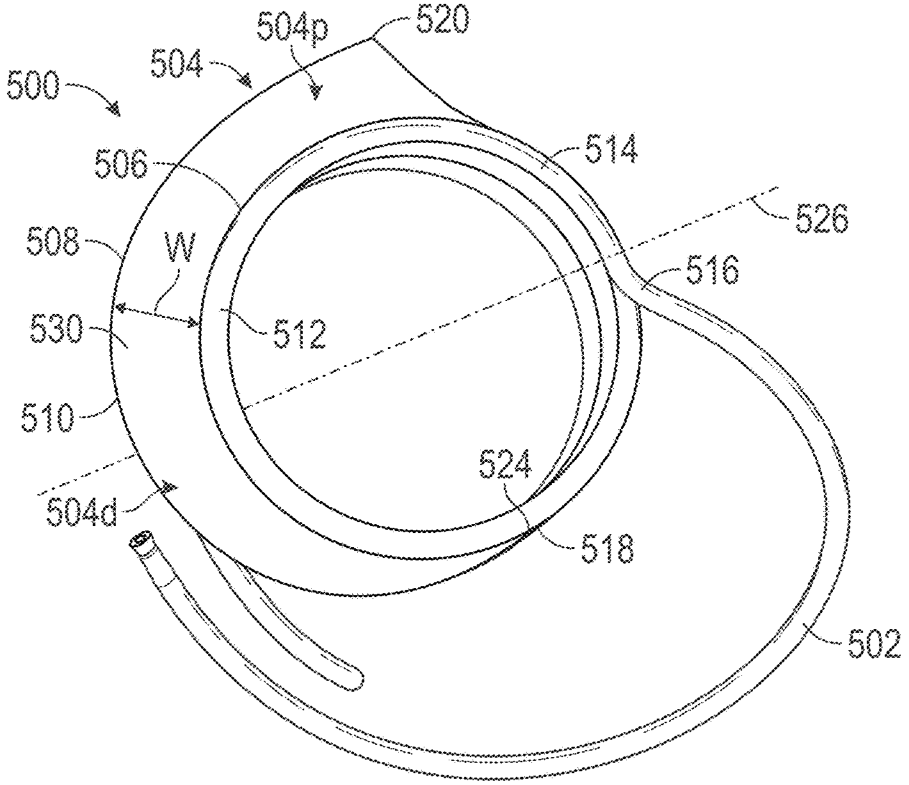
FIG. 25B is a top perspective view of the docking device depicted in FIG. 25A.
Figure 25C:
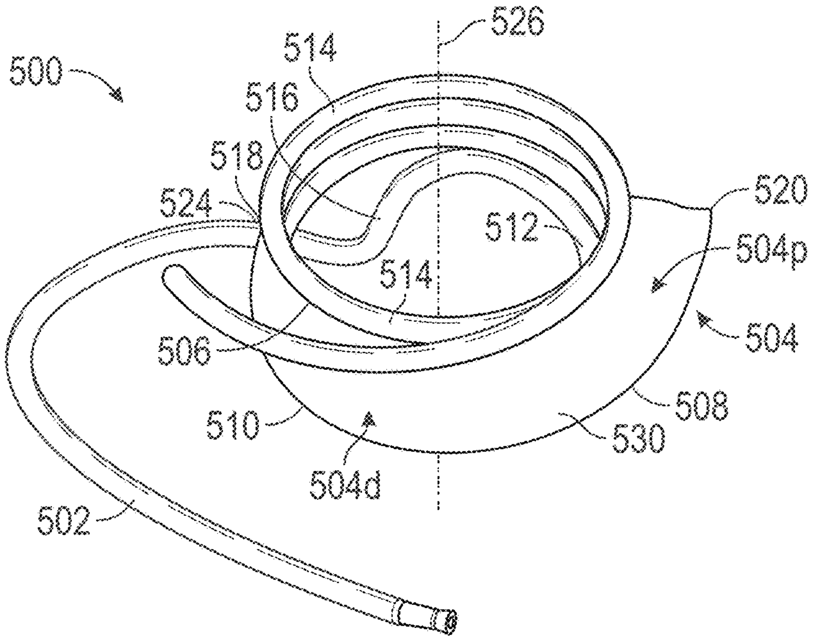
FIG. 25C is a bottom perspective view of the docking device depicted in FIG. 25A.

FIGS. 25A-25C show a docking device 500, according to another example. The docking device 500 includes a coil 502 which can move from a substantially straight or delivery configuration to a helical or deployed configuration similar to the coil 102. The docking device 500 also includes a foldable PVL guard 504 attached to the coil 502. As described herein, the foldable PVL guard 504 is also referred to as a "sealing member" or a "skirt," and these terms are used interchangeably hereinafter.

Figure 26A:
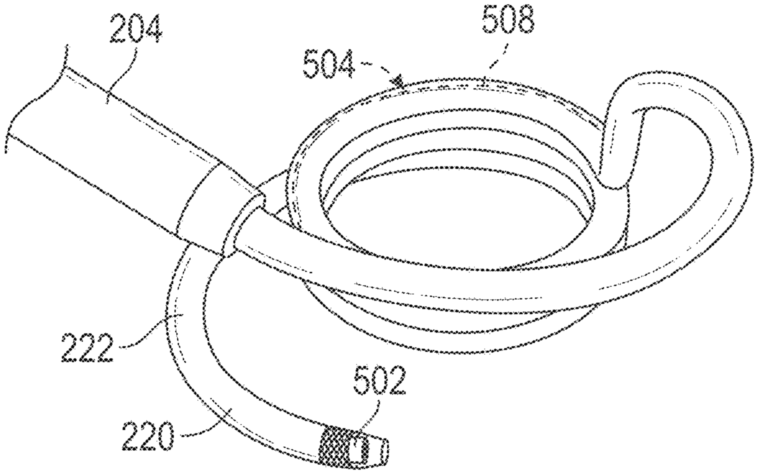
FIG. 26A is a perspective view of an example sleeve shaft covering the docking device of FIG. 25A and a sealing member of the docking device being in a delivery configuration.
Figure 26B:
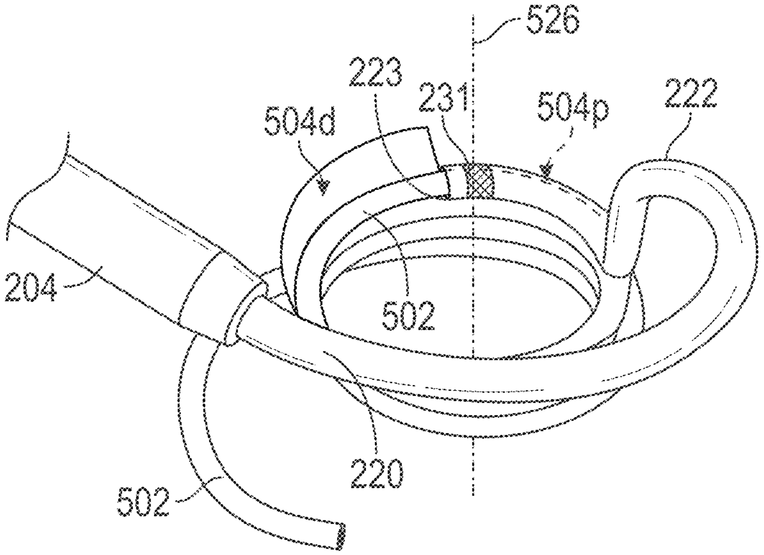
FIG. 26B depicts the sleeve shaft is partially removed from the docking device and a part of the sealing member is exposed and radially expanded.

The sealing member 504 can be movable between a delivery configuration (as shown in FIG. 26A) and a deployed configuration (as shown in FIGS. 25A-25C and FIGS. 27-31). In the delivery configuration, the sealing member 504 can be folded and retained within the dock sleeve 222 (which can be a distal end portion of the sleeve shaft 220, as described above). With the coil 502 in the deployed configuration (e.g., FIG. 26A), the sealing member 504 can be exposed (e.g., by retracting the dock sleeve 222 proximally relative to the docking device 500) and extend radially outwardly from the coil 502, as depicted in FIG. 26B. Such radially extended the sealing member 504 can be flat or substantially flat relative to a plane perpendicular to a central longitudinal axis 526 (see FIGS. 25C and 27).

In addition, FIG. 26B shows that the sealing member 504 is partially deployed from the dock sleeve 222. This can happen when the sealing member 504 is partially exposed, e.g., a distal portion 504*d* of the sealing member is exposed from the dock sleeve 222 but a proximal portion 504*p* of the sealing member is still covered by the dock sleeve 222. In such circumstances, the distal portion 504*d* of the sealing member can extend radially outwardly from the coil 502 and form a flat or substantially flat surface, whereas the proximal portion 504*p* of the sealing member can remain folded and covered by the dock sleeve 222.

Figure 25D:
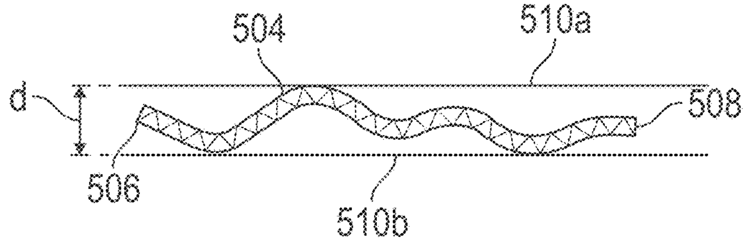
FIG. 25D is a cross-sectional view of a sealing member of the docking device and depicts an example measurement of flatness of the sealing member.

FIG. 25D shows a cross-sectional view of the sealing member 504 along a radial axis 525 and depicts an example measurement of flatness of the sealing member 504. For illustrative purposes, the cross-section of the sealing member 504 is depicted as an exaggeratedly rugged or uneven surface. The flatness measure of the sealing member 504 at the cross-section can be defined as a distance between two closest parallel lines 510*a*, 510*b* within which the cross-section of the sealing member 504 is bound (e.g., the highest point in the cross-section is located on the line 510*a* and the lowest point of the cross-section is located on the line 510*b*).

In certain examples, the flatness measure can be substantially uniform across the sealing member 504 (e.g., the flatness measure can be substantially constant at various cross-sections taken between the proximal end 518 and the distal end 520). In certain examples, the flatness measure can vary across the sealing member 504 (e.g., the flatness measure at a cross-section of the proximal 504*p* may be different from the flatness measure at a cross-section of the distal portion 504*d*).

As described here, the sealing member 504 (or a portion of the sealing member) is considered to be flat or substantially flat if a flatness measure at any cross-section of the sealing member 504 (or the portion of the sealing member) is smaller than a predefined threshold value. In certain examples, the predefined threshold value for the flatness measure can range from 1 mm to 10 mm, or from 2 mm to 8 mm, or from 3 mm to 6 mm, or from 4 mm to 5 mm.

The sealing member 504 can have an inner edge 506 coupled the coil 502 and an outer edge 508 that is movable between a folded position and an extended position. When the sealing member 504 is in the delivery configuration (see, e.g., FIG. 26A), the outer edge 508 of the sealing member 504 can be in the folded position such that the outer edge 508 can extend along and adjacent the coil 502. When the sealing member 504 is in the deployed configuration, the outer edge 508 can move to the extended position, e.g., at least a segment of the outer edge 508 can extend radially away or spaced apart from the coil 502 (see, e.g., FIGS. 25A-25C).

In some examples, as depicted in FIGS. 25A-25C, a distal end 518 of the outer edge 508 can be fixedly attached to the coil 502 (and to a distal end 524 of the inner edge 506), e.g., via sutures, glue, and/or any other attachment means, while a proximal end 520 of the outer edge 508 can be radially movable relative to the coil 502. For example, when the sealing member 504 is in the deployed configuration, both the proximal end 520 and a mid-portion (i.e., the portion between 518 and 520) of the outer edge 508 can extend radially away or spaced apart from the coil 502. As a result, the sealing member 504 in the deployed configuration can have a radially tapered or fan-like shape.

The sealing member 504 in the deployed configuration can have a width (W) defined between the inner edge 506 and the outer edge 508 (see, e.g., FIG. 25B). In certain examples, the width of the sealing member 504 can progressively increase (or in a step-wise manner) from the distal end 518 to the proximal end 520 of the outer edge 508. In certain examples, the width of the sealing member 504 can remain substantially constant along one or more segments of the outer edge 508. For example, the proximal portion 504*p* of the sealing member can have a substantially constant width such that the outer edge 508 can be parallel or at least substantially parallel to the sealing segment 512 in the proximal portion 504*p*. In certain examples, the proximal portion 504*p* of the sealing member can have a width ranging from 3 mm to 8 mm, or from 4 mm to 7 mm, or from 5 mm to 6 mm.

In other examples, the distal end 518 of the outer edge 508 can also be movable relative to the coil 502. In such circumstances, when the sealing member 504 is in the deployed configuration, the complete length of the outer edge 508 (including both the distal end 518 and the proximal end 518) can extend radially away or spaced apart from the coil 502. In such circumstances, the sealing member 504 in the deployed configuration can form a curved band, and the width of the sealing member 504 can be constant or can vary from the distal end 518 to the proximal end 520.

As described herein, the outer edge 508 in the extended position can contact native tissue at an implantation site (e.g., a native valve annulus and/or a wall of a chamber of the heart). Specifically, when the sealing member 504 is in the deployed configuration, the outer edge 508 can create a sealed and atraumatic interface between the docking device 500 and the native tissue so as to reduce or eliminate paravalvular leakage.

Figure 28A:
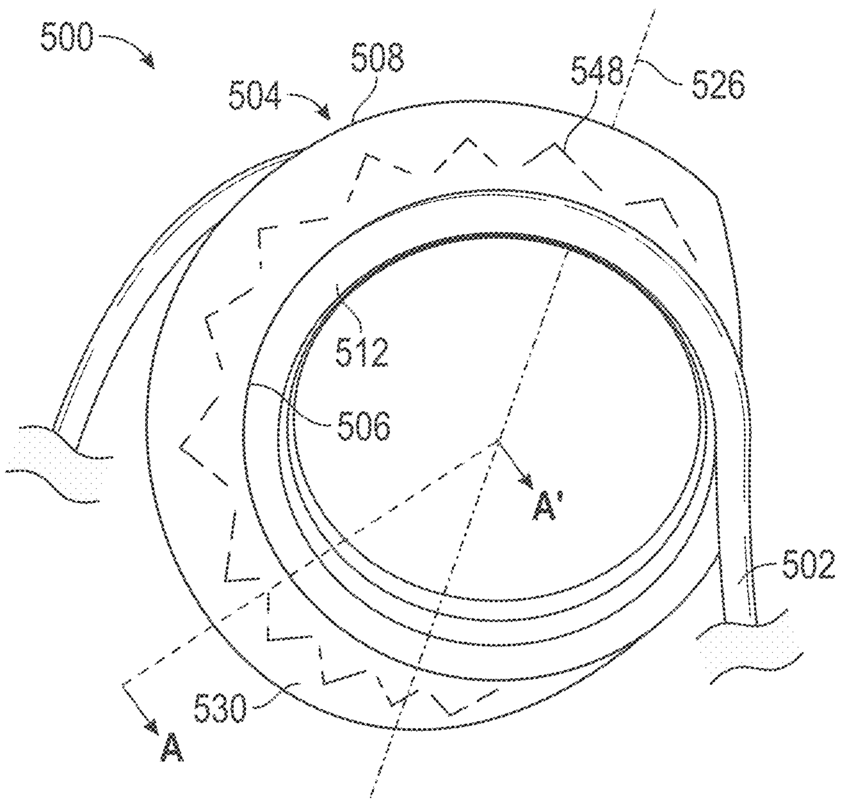
FIG. 28A is a top view of a docking device, according to another example.
Figure 28B:
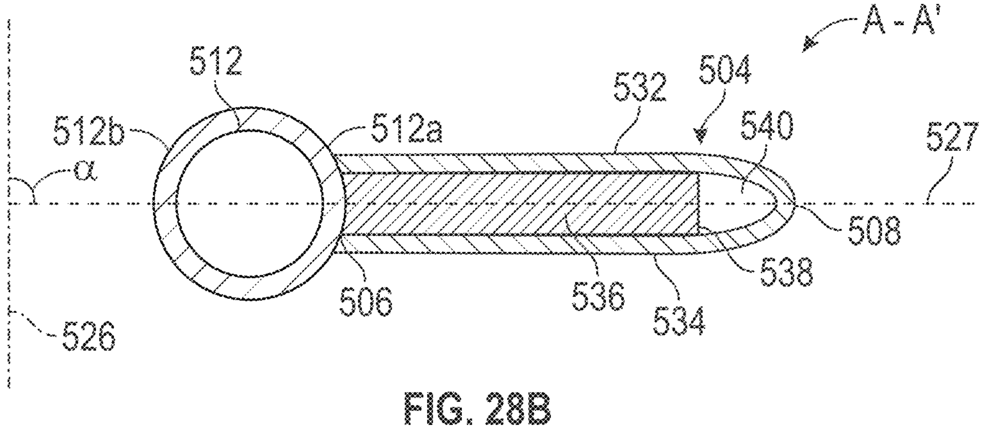
FIG. 28B is a cross-sectional view of the docking device of FIG. 28A.

In any of the examples described herein, the inner edge 506 of the sealing member 504 can be fixedly attached (e.g., via sutures, glues, and/or any other attachment means) to a sealing segment 512 of the coil 502. In certain examples, the inner edge 506 can be stitched to the sealing segment 512 via a plurality of in-and-out sutures. As depicted in FIG. 28B, the outer surface of the sealing segment 512 can have an outer part 512*a* and an inner part 512*b*, where the inner part 512*b* is closer to a central longitudinal axis 526 of the docking device 500 than the outer part 512*a*. In certain examples, a portion of the sealing member 504 adjacent the inner edge 506 can wrap around at least a portion of the sealing segment 512. For example, the sealing member 504 can wrap around the inner part 512*b*. In certain examples, as depicted in FIG. 28B, the inner edge 506 of the sealing member 504 can be attached to and extend from the outer part 512*a* of the sealing segment 512. Because the sealing segment 512 is not wrapped around by the sealing member 504, such a configuration can reduce the overall profile of the sealing member 504 when it is folded within the dock sleeve (e.g., in the delivery configuration).

In certain examples, the axial length of the sealing segment 512 can correspond to about the same segment of the coil 102 covered by the guard member 104 in the deployed configuration. For example, when the coil 502 is in the deployed configuration, the sealing segment 512 can extend from one of the functional turns 514 (e.g., similar to 108*p*) of the coil 502 to a position that is adjacent to (and slightly distal to) an ascending portion 516 (similar to 110*b*) of the coil 502.

When the sealing member 504 is in the deployed configuration, the outer edge 508 can form a helical shape rotating about the central longitudinal axis 526 of the docking device 500 so that the proximal end 520 of the outer edge 508 is offset from the distal end 518 of the outer edge 508 along the central longitudinal axis 526.

In certain examples, when the sealing member 504 is in the deployed configuration, the outer edge 508 can extend circumferentially relative to the central longitudinal axis 526 from 180 degrees to 400 degrees, or from 210 degrees to 330 degrees, or from 250 degrees to 290 degrees, or from 260 degrees to 280 degrees. In one particular example, when the sealing member 504 is in the deployed configuration, the outer edge 508 can extend circumferentially 270 degrees relative to the central longitudinal axis 526. In other words, the sealing member 504 can extend circumferentially from about one half of a revolution (e.g., 180 degrees) around the central longitudinal axis 526 in some examples to more than a full revolution (e.g., 400 degrees) around the central longitudinal axis 526 in other examples, including various ranges in between. As used herein, a range (e.g., 180-400 degrees, from 180 degrees to 400 degrees, and between 180 degrees and 400 degrees) includes the endpoints of the range (e.g., 180 degrees and 400 degrees).

When the coil 502 is in the deployed configuration, similar to the outer edge 508, the sealing segment 512 of the coil can also form a helical shape rotating about the central longitudinal axis 526 of the docking device 500 such that a proximal end of the sealing segment 512 is offset relative to a distal end of the sealing segment 512 along the central longitudinal axis 526.

As described above, the sealing member 504 in the deployed configuration can be flat or substantially flat. Thus, the outer edge 508 of the sealing member 504 can be generally coplanar with the sealing segment 512 of the coil 502. The flat or substantial flat surface of the sealing member 504 in the deployed configuration can form a right angle or an oblique angle relative to the central longitudinal axis 526 of the docking device 500, when viewed from the top of coil 502 in FIG. 25A. To illustrate, FIG. 28B shows a cross-sectional view of the sealing member 504 along a radial axis 527. The radial axis 527 extends through the width of the sealing member 504 and intersects with the central longitudinal axis 526 for form an angle $\alpha$. In certain examples, the sealing member 504 can be angled upwardly relative to the sealing segment 512. In other words, the angle $\alpha$ can be less than 90 degrees. For example, the angle $\alpha$ can be between 0 degree and 90 degrees (e.g., 85 degrees), or between 20 degrees and 80 degrees (e.g., 75 degrees), or between 30 degrees and 70 degrees (e.g., 60 degrees). In certain examples, the sealing member 504 can be perpendicular to the central longitudinal axis 526, i.e., the angle $\alpha$ can be 90 degrees. In other examples, the sealing member 504 can be angled downwardly relative to the sealing segment 512. In other words, the angle $\alpha$ can be greater than 90 degrees. For example, the angle $\alpha$ can be between 90 degree and 180 degrees (e.g., 160 degrees), or between 100 degrees and 150 degrees (e.g., 140 degrees), or between 110 degrees and 130 degrees (e.g., 120 degrees).

In any of the examples described above, example measurements of the sealing member 504 (e.g., the width W in FIG. 25B, the angle $\alpha$ in FIG. 28B, the flatness measure, etc.) in its deployed configuration can be obtained when the docking device 500 is deployed outside a patient's body. For example, the docking device 500 retained in a dock sleeve 222 can be deployed at a testing bench station by removing the dock sleeve 222 from the docking device 500, thereby allowing the sealing member 504 to radially extend to the deployed configuration.

As described more fully below, the sealing member 504 can comprise compliant materials. Thus, when deployed at the implantation site, the orientation (e.g., the radial axis 527) of sealing member 504 can adapt to the anatomy of the native tissue. For example, as noted above, the outer edge 508 in the extended position can contact or press against a native wall of a heart chamber. Thus, depending on the anatomy at the implantation site (e.g., the position and/or slope of the native wall contacting the outer edge 508 relative to the implanted docking device 500), the outer edge 508 can be positioned above or below the inner edge 506. As a result, the angle α measured at the implantation site (e.g., due to adaptation of the native anatomy) can be different from the angle α measured outside patient's body (e.g., in a testing bench station). In certain examples, the docking device 500 can have a tubular member (similar to 112) surrounding at least a portion of the coil 502. For example, the tubular member can surround the sealing segment 512, and a proximal end 522 of the inner edge 506 can be fixedly attached to the tubular member (e.g., via stitching sutures, glues, etc.). In certain examples, the docking device 500 can have a retention element (similar to 114) surrounding at least a portion of the tubular member. For example, the retention element can surround a portion of the tubular member adjacent to a distal end 524 of the inner edge 506. Both the distal end 524 of the inner edge 506 and the distal end 518 of the outer edge 508 can be fixedly attached to the retention element (e.g., via sutures, adhesive, etc.).

Exemplary Structure of the Foldable PVL Guard

In any of the examples described herein, the sealing member 504 can be assembled separately before being attached to the coil 502.

In certain examples, the sealing member 504 can have a spine 528 (also referred to as an "expansion member" or "support frame") extending along at least a portion of the outer edge 508 and a biocompatible cover 530 (also referred to as a "sealing portion" or a "sealing membrane") extending between the inner edge 506 and the outer edge 508. As noted above, the sealing member 504 in the deployed configuration can have a tapered shape. Thus, a proximal end portion of the cover 530 can have a larger radial width than a distal end portion of the cover 530. Generally, the spine 528 can be stiffer than the cover 530.

The spine 528 can be biased to the deployed configuration and can be moved (e.g., elastically deformed) to the delivery configuration. For example, the spine 528 can include a shape memory material, such as nickel titanium alloy (e.g., nitinol). During delivery, the spine 528 can be retained within the dock sleeve (i.e., the sealing member 504 is in the delivery configuration), extending along and adjacent to the sealing segment 512 of the coil. When the dock sleeve is removed (i.e., the sealing member 504 is in the deployed configuration), the spine 528 can return to its shape set position. In lieu of or in addition to biasing the spine, one or more other mechanisms (e.g., spring, etc.) can be used to move the spine 528 from the delivery position to the deployed position. In some examples, the spine 528 can include one or more alloys such as nitinol, cobalt chromium, and/or stainless steel. In some examples, the spine 528 can include one or more polymeric materials such as polyether ether ketone (PEEK) and/or polyethylene terephthalate (PET) and/or ePTFE/PTFE. In some examples, the spine 528 can include a suture (e.g., a braided surgical suture).

In any of the examples described herein, the cover 530 can include at least one layer of material configured to restrict or prevent blood from passing therethrough, thereby preventing or reducing paravalvular leakage when the sealing member 504 is in the deployed configuration. The cover 530 can include one or more of cloth, PEEK, ePTFE, PET, thermoplastic polyurethane (TPU), and foam. In certain examples, the cover 530 can be monolayer. In certain examples, the cover 530 can have a multi-layer structure, as described below.

In certain examples, the cover 530 can include at least two laminated layers (also referred to as "cover layers"), e.g., a top layer 532 and a bottom layer 534 (sec, e.g., FIG. 28B). In certain examples, the cover 530 can include two cloth layers. In certain examples, the cover 530 can include one cloth layer and one layer comprising ePTFE. Respective inner edges of the layers can be fixedly attached to (e.g., via stitches, glue, thermal compression, etc.) to the scaling segment 512 of the coil 502, as noted above. Respective outer edges of the layers can be sealed.

Figure 27:
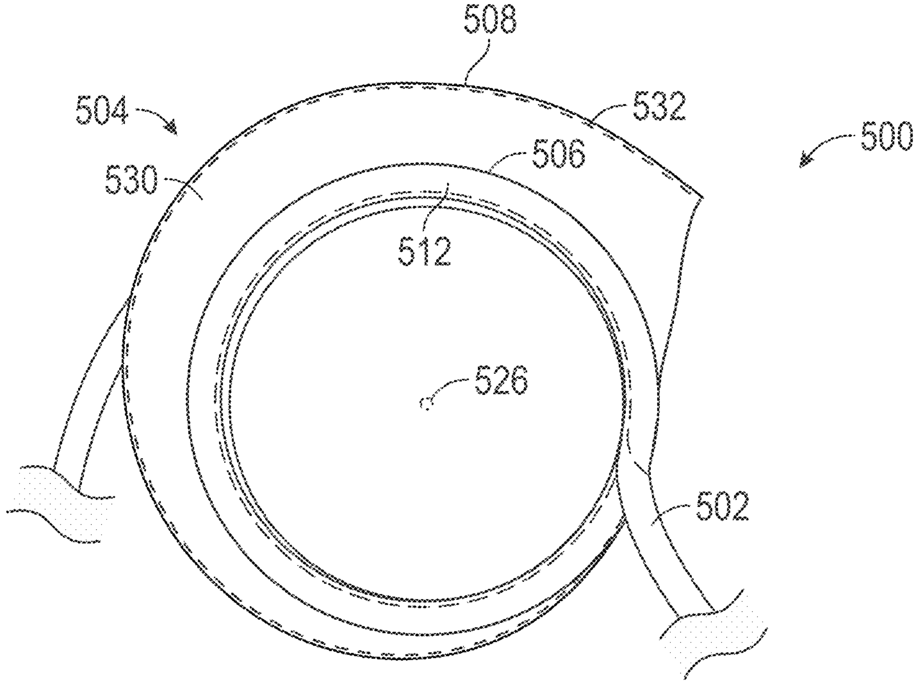
FIG. 27 is a top view of a docking device, according to another example.

In certain examples, a soldering iron can be used to seal the at least two layers at their respective outer edges to form the outer edge 508 of the sealing member 504. In certain examples, the at least two layers can be sealed along their respective outer edges using a plurality of in-and-out stitches 532, as illustrated in FIG. 27. In certain cases, after stitching two layers along a stitching line adjacent to their respective outer edges, the two layers can be flipped inside-out along the stitching line, which can form the outer edge 508 of the sealing member 504. In certain examples, the cover 530 can include a third layer 536 inserted between the top and bottom layers 532, 534, as depicted in FIG. 28B. In certain examples, the third layer 536 can include a foam material. In certain examples, the third layer 536 can include TPU. In certain examples, the cover 530 can have a plurality of in-and-out stitches coupling the third layer 536 to the top and bottom layers 532, 534 along an outer edge 538 of the third layer 536. In certain examples, the cover 530 can have a plurality of stitches 548 running in a zig-zag pattern (see, e.g., FIG. 28A) to couple the third layer 536 to the top and bottom layers 532, 534.

On one hand, the cover 530 described herein is configured to be sufficiently thin so that it can be folded within the dock sleeve. For example, the thickness of the cover can between 0.02 mm and 0.30 mm, or between 0.05 mm and 0.20 mm, or between 0.06 mm and 0.10 mm. On the other hand, the cover 530 is configured to have a sufficient density or weight so that it will remain stable and not dislocated when deployed in the target location. For example, when the sealing member 504 is in the deployed configuration, the outer edge 508 can remain contact with the native wall and the cover 530 is configured to not move up and/or down with the blood flow, thus forming a stable seal between the docking device 500 and the native wall to reduce paravalvular leakage.

In certain examples, the cover 530 can have a pocket 540 extending along the outer edge 508 and configured to receive the spine 528. If the cover 530 has at least two layers, the pocket 540 can be created by stitching the cover 530 along a line 542 (see, e.g., FIG. 29) that is spaced apart from the outer edge 508. In certain cases (e.g., when the cover 530 has a monolayer structure), the cover 530 can be folded along the outer edge 508, and a seam can be added to the folded cover (e.g., via stitches, glue, thermal compression, etc.) to create the pocket 540.

The spine 528 can be inserted into the pocket 540. In certain examples, a distal end 528*d* of the spine 528 can be fixedly attached to a distal end portion (e.g., the distal end 518) of the outer edge 508. Thus, when the distal end 518 of the outer edge 508 is fixedly attached to the coil 502, the distal end 528*d* of the spine 528 can also be fixedly attached to the coil 502.

In certain examples, a proximal end 528*p* of the spine 528 can also be fixedly attached to a proximal end portion (e.g., the proximal end 520) of the outer edge 508 (see, e.g., FIG. 25A). In such circumstances, the spine 528 is not movable within the pocket 540 (since both the proximal end 528*p* and the distal end 528*d* of the spine are fixedly attached to the outer edge 508.

Figure 29:
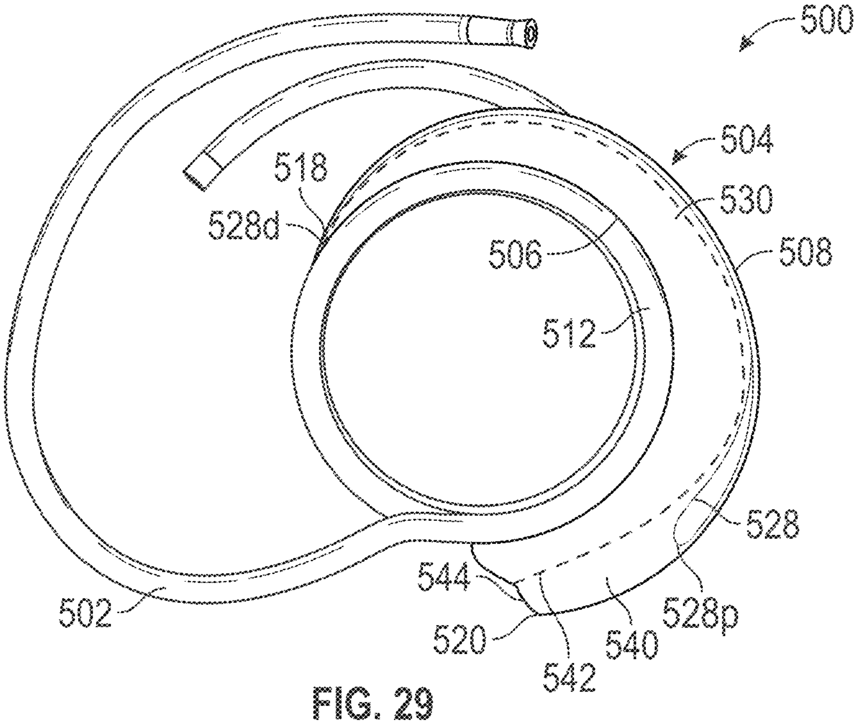
FIG. 29 is a top view of a docking device, according to another example.

In other examples, the proximal end 528*p* of the spine 528 is a free end and can move along the outer edge 508 when the outer edge 508 moves between the folded position and the extended position (see, e.g., FIG. 29). In other words, the proximal end 528*p* of the spine 528 can move or slide within the pocket 540.

In certain examples, the pocket 540 can have a closed proximal end 544. The proximal end 544 of the pocket 540 can be closed or sealed by soldering, stitching, or other means. In certain examples, the proximal end 528*p* of the spine 528 can have an atraumatic shape configured not piercing through the closed proximal end 544 of the pocket 540. For example, as depicted in FIG. 29, the proximal end 528*p* of the spine 528 can form a curved loop. In certain examples, the proximal end 528*p* of the spine 528 can be configured to be retained within and not extend out of the pocket 540. For example, the proximal end 528*p* of the spine 528 can be spaced away from the proximal end 544 of the pocket 540 (whether the sealing member 504 is in the delivery configuration or deployed configuration) so that it does not apply pressure to the closed proximal end 544 of the pocket 540. In one particular example, when the sealing member 504 is in the deployed configuration, a distance between the proximal end 528*p* of the spine 528 and the proximal end 544 of the pocket 540 can range from about 10 mm to about 14 mm (e.g., about 12 mm).

Exemplary Method of Deploying Foldable PVL Guard

The procedure for delivering the docking device 500 to an implantation site and implanting a prosthetic valve (such as the prosthetic valve 10 described above) within the docking device 500 can be generally similar to the procedure described above in reference to FIGS. 11-24, with the exceptions described below.

Figure 30:
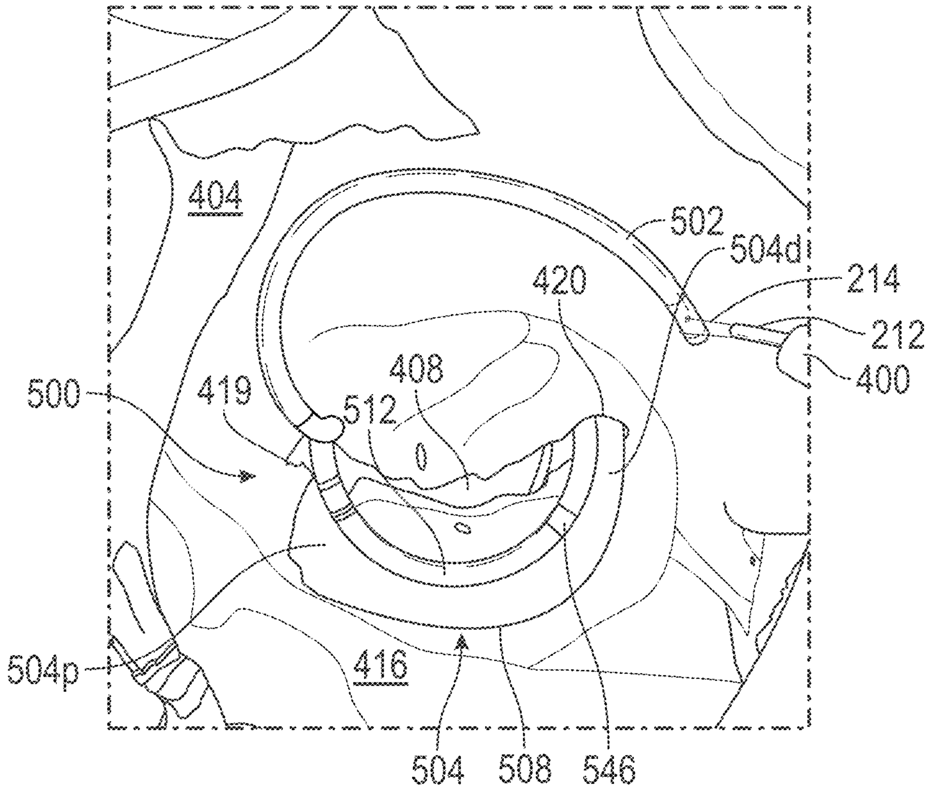
FIG. 30 is an atrial side view of a docking device implanted in the mitral valve, according to one example.

As noted above, after the functional turns of the docking device successfully wraps round the native leaflets and the chordae tendineae (sec, e.g., FIGS. 14-15), the dock sleeve 222 can be retracted in a proximal direction until it is retracted back into the delivery sheath 204. FIG. 30 illustrates the fully deployed docking device 500. As shown, without being constrained by the dock sleeve 222, the sealing member 504 can extend radially outwardly from the coil 502, e.g., as the spine 528 moves from the biased position to the unbiased position. As described above, the release suture 214 can be cut so as to release the docking device 500 from the delivery apparatus 200.

Unlike FIGS. 16A-16C and 17 which show the radially expanded guard member 104 surrounding a portion of the coil 102, FIG. 30 shows that the sealing member 504 in its deployed configuration forms a flat or substantially flat surface extending radially outwardly from the coil 502. In addition, unlike the docking device 100 depicted in FIGS. 16B-16C, where repositioning the proximal end 105 of guard member 104 may be needed (because the proximal end portion 104*p* can axially move relative to the coil 102), no such repositioning step is needed for the docking device 500 (because the inner edge 506 of the sealing member 504 is fixedly attached to the coil 502).

As shown in FIG. 30, the distal portion 504*d* of the sealing member can be configured to extend to a location adjacent to the posteromedial commissure 420. In certain examples, the distal portion 504*d* of the sealing member can be configured to extend through the native mitral valve annulus 408 and into the left ventricle 414. The proximal portion 504*p* of the sealing member can be configured to be positioned adjacent to the anterolateral commissure 419 of the native valve. As described above, the outer edge 508 of the sealing member 504 can be configured to remain contact with the posterior wall 416 of the left atrium 404. Thus, the sealing member 504 can form a stable seal between the docking device 500 and the native wall of the left atrium to reduce paravalvular leakage.

Positioning of the sealing member 504 relative to the anatomy of the native mitral valve annulus 408 can be examined by visualizing the position of at least one radiopaque marker located on the docking device 500 under fluoroscopy. For example, FIG. 30 shows a radiopaque marker 546 located on the sealing segment 512 of the docking device 500. The radiopaque marker 546 can have a predetermined axial distance to the distal end 524 of the inner edge 506 of the sealing member 504. In the example depicted in FIG. 30, the radiopaque marker 546 is located slightly proximal to the posteromedial commissure 420.

After deploying the docking device 500, a prosthetic valve (e.g., 10) can be delivered into the left atrium 404, placed within the docking device 500, and then radially expanded, following similar steps described above in reference to FIGS. 18-23.

Figure 31:
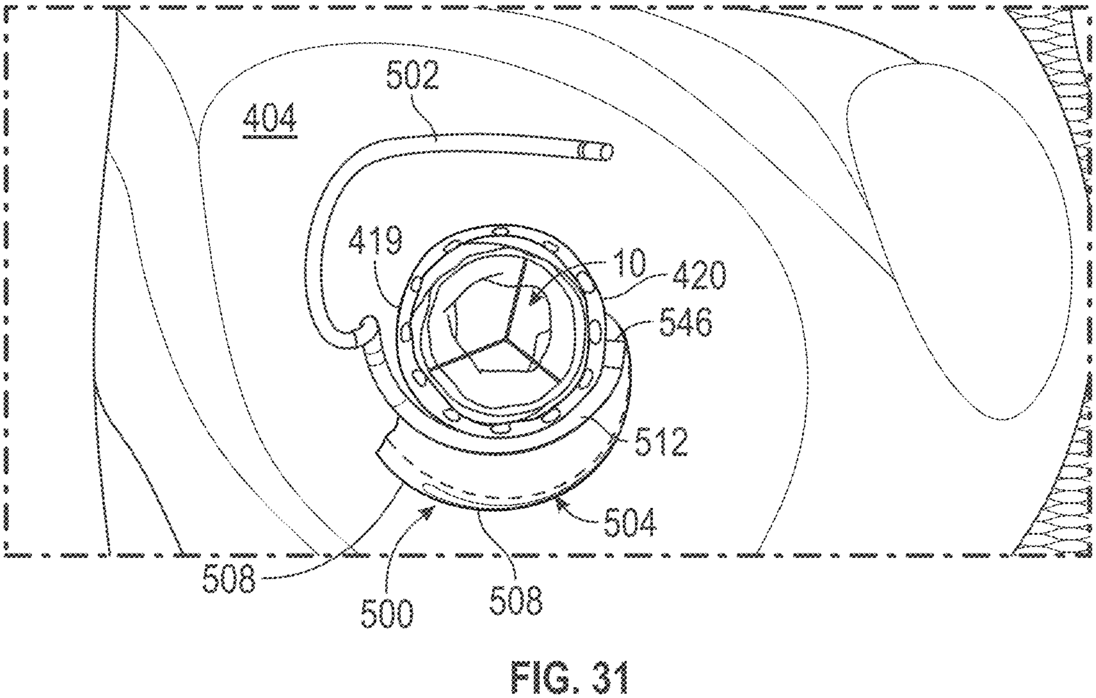
FIG. 31 is an atrial side view of the docking device of FIG. 30 after a prosthetic valve is received within the docking device, according to one example.

FIG. 31 illustrates the final disposition of the docking device 500 at the mitral valve and the prosthetic valve 10 received within the docking device 500. As noted above, radially expanding the prosthetic valve 10 within the docking device 500 can cause further radial expansion of the coil 502 as well as circumferential rotation of the functional turns and slight unwinding of the helical coil 502 (i.e., clocking). As a result, the sealing segment 512 of the coil 502 can rotate slightly. For example, FIG. 31 shows that the radiopaque marker 546 can move slightly distally (compared to FIG. 30) to the location corresponding to the posteromedial commissure 420. Thus, position of the radiopaque marker 546 relative to posteromedial commissure 420 can be used to confirm final disposition of the docking device 500 and proper expansion of the prosthetic valve 10.

As described above, the radial tension between the prosthetic valve 10 and the central region of the docking device 500 can securely hold the prosthetic valve 10 in place. In addition, the sealing member 504 can act as a seal between the docking device 500 and the native wall to prevent or reduce paravalvular leakage around the prosthetic valve 10.

Sterilization

Any of the systems, devices, apparatuses, etc. herein can be sterilized (for example, with heat/thermal, pressure, steam, radiation, and/or chemicals, etc.) to ensure they are safe for use with patients, and any of the methods herein can include sterilization of the associated system, device, apparatus, etc. as one of the steps of the method. Examples of heat/thermal sterilization include steam sterilization and autoclaving. Examples of radiation for use in sterilization include, without limitation, gamma radiation, ultra-violet radiation, and electron beam. Examples of chemicals for use in sterilization include, without limitation, ethylene oxide, hydrogen peroxide, peracetic acid, formaldehyde, and glutaraldehyde. Sterilization with hydrogen peroxide may be accomplished using hydrogen peroxide plasma, for example.

Additional Examples of the Disclosed Technology

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A docking device for securing a prosthetic valve at a native valve, the docking device comprising: a coil; a guard member surrounding at least a portion of the coil, wherein the guard member comprises a first layer and a second layer that are fused with each other at a proximal end and a distal end of the guard member; wherein the distal end of the guard member is fixedly attached to the coil; wherein the proximal end of the guard member is movable relative to the coil; wherein the guard member is movable between a radially compressed state and a radially expanded state.

Example 2. The docking device of any example herein, particularly example 1, wherein in the radially expanded state, at least a portion of the guard member extends radially outwardly relative to the coil such that the guard member can reduce paravalvular leakage around the prosthetic valve when deployed at the native valve.

Example 3. The docking device of any example herein, particularly any one of examples 1-2, wherein the proximal end of the guard member is configured to slide distally over the coil when the guard member moves from the radially compressed state to the radially expanded state.

Example 4. The docking device of any example herein, particularly any one of examples 1-3, wherein in the radially expanded state, the proximal end of the guard member has a smaller diameter than the distal end of the guard member.

Example 5. The docking device of any example herein, particularly any one of examples 1-4, wherein the first layer is an inner layer and the second layer is an outer layer relative to the coil.

Example 6. The docking device of any example herein, particularly any one of examples 1-5, wherein the first layer comprises a thermoplastic material.

Example 7. The docking device of any example herein, particularly example 6, wherein the first layer comprises braided PET.

Example 8. The docking device of any example herein, particularly any one of examples 6-7, wherein the first layer comprises plastic monofilament fibers.

Example 9. The docking device of any example herein, particularly example 8, wherein the plastic monofilament fibers have a diameter ranging between 0.002 inch and 0.004 inch.

Example 10. The docking device of any example herein, particularly any one of examples 1-9, wherein the second layer comprises a thermoplastic polymeric material.

Example 11. The docking device of any example herein, particularly example 10, wherein the second layer comprises braided PET.

Example 12. The docking device of any example herein, particularly any one of examples 10-11, wherein the second layer comprises multifilament fibers.

Example 13. The docking device of any example herein, particularly example 12, wherein the second layer comprises 24-filament fibers.

Example 14. The docking device of any example herein, particularly any one of examples 1-13, wherein the first layer comprises a smaller number of fibers than the second layer.

Example 15. The docking device of any one of 1-14, wherein the first layer comprises between 32 and 64 fibers.

Example 16. The device of any example herein, particularly example 15, wherein the first layer comprises 48 fibers.

Example 17. The docking device of any one of 1-16, wherein the second layer comprises between 80 and 112 fibers.

Example 18. The docking device of any example herein, particularly example 17, wherein the second layer comprises 96 fibers.

Example 19. A method for assembling a docking device configured to receive a prosthetic valve, the method comprising: forming a guard member having a proximal end and a distal end; and attaching the guard member to the docking device; wherein the guard member comprises a first layer and a second layer that are fused together at the proximal end and the distal end; wherein the guard member surrounds at least a portion of a coil of the docking device and is movable between a radially compressed state and a radially expanded state; wherein the distal end of the guard member is fixed relative to the coil and the proximal end of the guard member is movable relative to the coil; wherein in the radially expanded state, the guard member is configured to reduce paravalvular leakage around the prosthetic valve.

Example 20. The method of any example herein, particularly example 19, wherein forming the guard member comprises braiding the first layer over a mandrel.

Example 21. The method of any example herein, particularly example 20, wherein forming the guard member comprises braiding a first portion of the first layer over a cylindrical body portion of the mandrel and braiding a second portion of the first layer over a tapered end portion of the mandrel.

Example 22. The method of any example herein, particularly any one of examples 20-21, wherein forming the guard member comprises braiding the second layer over the first layer. Example 23. The method of any example herein, particularly example 22, wherein forming the guard member further comprises shape-setting the guard member around the mandrel.

Example 24. The method of any example herein, particularly example 23, wherein shape-setting the guard member comprises heating the guard member at a predetermined temperature over a predetermined duration so that the guard member conforms to a shape of the mandrel.

Example 25. The method of any example herein, particularly any one of examples 20-24, wherein forming the guard member further comprises cutting the guard member at the proximal end and the distal end.

Example 26. The method of any example herein, particularly example 25, wherein the cutting comprises applying a laser beam to the proximal end and the distal end of the guard member, wherein the laser beam melts the first layer and the second layer at the proximal end and the distal end.

Example 27. The method of any example herein, particularly any one of examples 19-26, wherein the first layer comprises a thermoplastic material.

Example 28. The method of any example herein, particularly any one of examples 19-27, wherein the first layer comprises braided PET.

Example 29. The method of any example herein, particularly any one of examples 19-28, wherein the second layer comprises a thermoplastic polymeric material.

Example 30. The method of any example herein, particularly any one of examples 19-29, wherein the second layer comprises braided PET.

Example 31. A method for assembling a cover assembly for a docking device configured to receive a prosthetic valve, the method comprising: braiding a first layer over a mandrel; braiding a second layer over the first layer to form a multi-layer structure; shape setting the multi-layer structure so that the multi-layer structure conforms to a shape of the mandrel; laser cutting the multi-layer structure to form a proximal end and a distal end; allowing the proximal end and the distal end to cure such that the second layer and the first layer are fused at the proximal end and the distal end.

Example 32. The method of any example herein, particularly example 31, where braiding the first layer to the mandrel comprises braiding a first portion of the first layer over a cylindrical body portion of the mandrel and braiding a second portion of the first layer over a tapered end portion of the mandrel.

Example 33. The method of any example herein, particularly example 32, wherein braiding the second layer over the first layer comprises braiding a first portion of the second layer over the first portion of the first layer and braiding a second portion of the second layer over the second portion of the first layer.

Example 34. The method of any example herein, particularly example 33, wherein the shape setting comprises heating the multi-layer structure at a predetermined temperature over a predetermined duration so that the first portions of the first and second layers conform to the cylindrical body portion of the mandrel and the second portions of the first and second layers conform to the tapered end portion of the mandrel.

Example 35. The method of any example herein, particularly any one of examples 31-34, wherein the first layer comprises a first thermoplastic material and the second layer comprises a second thermoplastic material.

Example 36. A method for assembling a cover assembly for a docking device configured to receive a prosthetic valve, the method comprising: braiding a first layer over a mandrel, the mandrel having a cylindrical body portion and a tapered end portion; braiding a second layer over the first layer to form a multi-layer structure; shape setting the multi-layer structure so that the multi-layer structure conforms to a shape of the mandrel; and laser cutting the multi-layer structure to form a proximal end and a distal end, wherein the second layer and the first layer are fused at the proximal end and the distal end.

Example 37. The method of any example herein, particularly example 36, wherein the first layer comprising a first plurality of thermoplastic fibers, and the second layer comprising a second plurality of thermoplastic fibers.

Example 38. The method of any example herein, particularly example 37, wherein the first plurality of thermoplastic fibers are monofilament PET fibers and the second plurality of thermoplastic fibers are multifilament PET fibers, wherein the first plurality of thermoplastic fibers have a larger fiber diameter and a smaller braiding density than the second plurality of thermoplastic fibers.

Example 39. A method for implanting a prosthetic valve, the method comprising:

deploying a docking device at a native valve, wherein the docking device comprises a coil and a guard member covering at least a portion of the coil; and deploying the prosthetic valve within the docking device; wherein the guard member comprises a first layer and a second layer that are fused together at a proximal end and a distal end of the guard member; wherein the guard member is movable between a radially compressed state and a radially expanded state; wherein a distal end of the guard member is fixed relative to the coil and a proximal end of the guard member is movable relative to the coil; wherein in the radially expanded state, the guard member is configured to reduce paravalvular leakage around the prosthetic valve.

Example 40. The method of any example herein, particularly example 39, wherein deploying the docking device at the native valve comprises wrapping around leaflets of the native valve with one or more functional turns of the coil and resting a stabilization turn of the coil against a native wall around the native valve.

Example 41. The method of any example herein, particularly example 40, wherein deploying the prosthetic valve comprises placing the prosthetic valve in a radially compressed state within the one or more functional turns of the coil and radially expanding the prosthetic valve to a radially expanded state, wherein radially expanding the prosthetic valve causes radial expansion of the one or more functional turns of the coil.

Example 42. The method of any example herein, particularly any one of examples 39-41, wherein the first layer comprises a first thermoplastic material and the second layer comprises a second thermoplastic polymeric material that is different from the first thermoplastic material.

Example 43. The method of any example herein, particularly any one of examples 39-42, wherein the first layer comprises braided PET and the second layer comprises braided PET.

Example 44. The method of any example herein, particularly any one of examples 39-43, wherein the first layer comprises monofilament fibers and the second layer comprises multifilament PET fibers.

Example 45. The method of any example herein, particularly any one of examples 39-44, wherein fibers in the first layer have a larger diameter than fibers in the second layer.

Example 46. The method of any example herein, particularly any one of examples 39-45, wherein the second layer has a higher braid density than the first layer.

Example 47. A method comprising sterilizing the docking device of any example herein, particularly any one of examples 1-18.

Example 48. A method of implanting a prosthetic valve of any example herein, particularly any one of examples 39-46, wherein the implantation is performed on a human patient, or a non-living simulation.

The features described herein with regard to any example can be combined with other features described in any one or more of the other examples, unless otherwise stated. For example, any one or more of the features of one docking device can be combined with any one or more features of another docking device. As another example, any one or more features of a method for assembling a docking device or a cover assembly can be combined with any one or more features of another method of assembling a docking device or a cover assembly.

In view of the many possible examples to which the principles of the disclosed technology may be applied, it should be recognized that the illustrated examples are only preferred examples of the technology and should not be taken as limiting the scope of the disclosure. Rather, the scope of the claimed subject matter is defined by the following claims and their equivalents.

The invention claimed is:

1. A prosthetic valve docking device for securing a prosthetic heart valve at a native valve, the docking device comprising:

a coil comprising a plurality of helical turns when deployed at the native valve; and a guard member surrounding at least a portion of the coil, wherein the guard member comprises a first layer and a second layer that are fused with each other at a proximal end and a distal end of the guard member, wherein the distal end of the guard member is fixedly attached to the coil, wherein the proximal end of the guard member is movable relative to the coil, wherein the guard member is movable between a radially-compressed/axially-elongated state and a radially-expanded/axially-foreshortened state, wherein the proximal end of the guard member is configured to slide distally over the coil when the guard member moves from the radially-compressed/axially-elongated state to the radially-expanded/axially-foreshortened, wherein in the radially-expanded/axially-foreshortened state, at least a portion of the guard member extends radially outwardly relative to the coil such that the guard member can reduce paravalvular leakage around the prosthetic heart valve when deployed at the native valve.

2. The docking device of claim 1, wherein in the radially-expanded/axially-foreshortened state, the proximal end of the guard member has a smaller diameter than the distal end of the guard member.

3. The docking device of claim 1, wherein the first layer is an inner layer and the second layer is an outer layer relative to the coil.

4. The docking device of claim 1, wherein the first layer comprises a thermoplastic material.

5. The docking device claim 4, wherein the first layer comprises braided PET.

6. The docking device of claim 1, wherein the second layer comprises a thermoplastic polymeric material.

7. The docking device of claim 6, wherein the second layer comprises braided PET.

8. The docking device of claim 1, wherein the first layer comprises a smaller number of fibers than the second layer.

* * * * *